(12) United States Patent
Maciag et al.

(10) Patent No.: US 6,716,974 B1
(45) Date of Patent: Apr. 6, 2004

(54) THERAPEUTIC AND DIAGNOSTIC METHODS AND COMPOSITIONS BASED ON JAGGED/NOTCH PROTEINS AND NUCLEIC ACIDS

(75) Inventors: Thomas Maciag, Freeport, ME (US); Ann B. Zimrin, Baltimore, MD (US); Deena J. Small, Scarborough, ME (US); Igor A. Prudovsky, Old Orchard Beach, ME (US)

(73) Assignee: Maine Medical Center Research Institute, Scarborough, ME (US)

( * ) Notice: Subject to any disclaimer, the term of this patent is extended or adjusted under 35 U.S.C. 154(b) by 0 days.

(21) Appl. No.: 09/579,536

(22) Filed: May 24, 2000

Related U.S. Application Data

(63) Continuation-in-part of application No. 09/199,865, filed on Nov. 25, 1998, now Pat. No. 6,433,138, which is a continuation of application No. PCT/US97/09407, filed on May 30, 1997.
(60) Provisional application No. 60/018,841, filed on May 31, 1996.

(51) Int. Cl.$^7$ ............................................... C07H 21/04
(52) U.S. Cl. ..................... 536/23.5; 435/69.1; 435/99.1; 435/254.2; 435/320.1
(58) Field of Search ............................... 435/69.1, 91.1, 435/254.2, 320.1; 536/23.5

*Primary Examiner*—Patrick J. Nolan
*Assistant Examiner*—Amy DeCloux
(74) *Attorney, Agent, or Firm*—Morgan, Lewis & Bockius, LLP

(57) ABSTRACT

This invention relates to therapeutic and diagnostic methods and compositions based on Jagged/Notch proteins and nucleic acids, and on their role in the signaling pathway relating to endothelial cell migration and/or differentiation. In addition, this invention provides a substantially purified Jagged protein, as well as a substantially purified nucleic acid or segment thereof encoding Jagged protein, or a functionally equivalent derivative, or allelic or species variant thereof. Further, this invention provides a substantially purified soluble Jagged protein and a substantially purified nucleic acid encoding same as well as a recombinant cell comprising a nucleic acid encoding a soluble Jagged protein. Soluble Jagged provides further therapeutic and diagnostic methods relating to diseases, disorders, and conditions involving Jagged/Notch signaling including, inter alia, angiogenesis, differentiation, and control of gene expression.

11 Claims, 18 Drawing Sheets

Domain Structure of the Notch Receptor Family

- ■ Transmembrane Domain (T)
- ▯ Cys-Rich Domain (Notch Lin Glp Repeats, NLG)
- ☐ Ankyrin Repeat Domain
- ▨ Proline Glutamate Serine Threonine (PEST) Domain (A)
- ◩ Polyglutamine-Rich (OPA) Domain (O)
- ▤ Nuclear Localization Signal Domain (N)
- ⊠ Cys-Poor Domain (C)
- ⊞ EGF Repeat Domain
- ▯ Signal Peptide Sequence (S)

| | | | | | |
|---|---|---|---|---|---|
| 1 | MRSPRTRGRS | GRPLSLLLAL | LCALRAKVCG | ASGQFELEIL | SMQNVNGELQ |
| 51 | NGNCCGGARN | PGDRKCTRDE | CDTYFKVCLK | EYQSRVTAGG | PCSFGSGSTP |
| 101 | VIGGNTFNLK | ASRGNDRNRI | VLPFSFAWPR | SYTLLVEAWD | SSNDTVQPDS |
| 151 | IIEKASHSGM | INPSRQWQTL | KQNTGVAHFE | YQIRVTCDDY | YYGFGCNKFC |
| 201 | RPRDDFFGHY | ACDQNGNKTC | MEGWMGPECN | RAICRQGCSP | KHGSCKLPGD |
| 251 | CRCQYGWQGL | YCDKCIPHPG | CVHGICNEPW | QCLCETNWGG | QLCDKDLNYC |
| 301 | GTHQPCLNGG | TCSNTGPDKY | QCSCPEGYSG | PNCEIAEHAC | LSDPCHNRGS |
| 351 | CKETSLGFEC | ECSPGWTGPT | CSTNIDDCSP | NNCSHGGTCQ | DLVNGFKCVC |
| 401 | PPQWTGKTCQ | LDANECEAKP | CVNAKSCKNL | IASYYCDCLP | GWMGQNCDIN |
| 451 | INDCLGQCQN | DASCRDLVNG | YRCICPPGYA | GDHCERDIDE | CASNPCLNGG |
| 501 | HCQNEINRFQ | CLCPTGFSGN | LCQLDIDYCE | PNPCQNGAQC | YNRASDYFCK |
| 551 | CPEDYEGKNC | SHLKDHCRTT | PCEVIDSCTV | AMASNDTPEG | VRYISSNVCG |
| 601 | PHGKCKSQSG | GKFTCDCNKG | FTGTYCHENI | NDCESNPCRN | GGTCIDGVNS |
| 651 | YKCICSDGWE | GAYCETNIND | CSQNPCHNGG | TCRDLVNDFY | CDCKNGWKGK |
| 701 | TCHSRDSQCD | EATCNNGGTC | YDEGDAFKCM | CPGGWEGTTC | NIARNSSCLP |
| 751 | NPCHNGGTCV | VNGESFTCVC | KEGWEGPICA | QNTNDCSPHP | CYNSGTCVDG |
| 801 | DNWYRCECAP | GFAGPDCRIN | INECQSSPCA | FGATCVDEIN | GYRCVCPPGH |
| 851 | SGAKCQEVSG | RPCITMGSVI | PDGAKWDDDC | NTCQCLNGRI | ACSKVWCGPR |
| 901 | PCLLHKGHSE | CPSGQSCIPI | LDDQCFVHPC | TGVGECRSSS | LQPVKTKCTS |
| 951 | DSYYQDNCAN | ITFTFNKEMM | SPGLTTEHIC | SELRNLNILK | NVSAEYSIYI |
| 1001 | ACEPSPSANN | EIHVAISAED | IRDDGNPIKE | ITDKIIDLVS | KRDGNSSLIA |
| 1051 | AVAEVRVQRR | PLKNRTDFLV | PLLSSVLTVA | WICCLVTAFY | WCLRKRRKPG |
| 1101 | SHTHSASEDN | TTNNVREQLN | QIKNPIEKHG | ANTVPIKDYE | NKNSKMSKIR |
| 1151 | THNSEVEEDD | MDKHQQKARF | GKQPAYTLVD | REEKPPNGTP | TKHPNWTNKQ |
| 1201 | DNRDLESAQS | LNRMEYIV | | | |

FIG. 8A

```
   1 ATGCGTTCCC CACGGACRCG CGGCCGGTCC GGGCGCCCCC TAAGCCTCCT
  51 GCTCGCCCTG CTCTGTGCCC TGCGAGCCAA GGTGTGTGGG GCCTCGGGTC
 101 AGTTCGAGTT GGAGATCCTG TCCATGCAGA ACGTAACGG  GGAGCTGCAG
 151 AACGGGAACT GCTGCGGCGG CGCCCGGAAC CCGGGAGACC GCAAGTGCAC
 201 CCGCGACGAG TGTGACACAT ACTTCAAAGT GTGCCTCAAG GAGTATCAGT
 251 CCCGCGTCAC GGCCGGGGGG CCCTGCAGCT TCGGCTCAGG GTCCACGCCT
 301 GTCATCGGGG GCAACACCTT CAACCTCAAG GCCAGCCGCG GCAACGACCG
 351 CAACCGCATC GTGCTGCCTT TCAGTTTCGC CTGGCCGAGG TCCTATACGT
 401 TGCTTGTGGA GGCGTGGGAT TCCAGTAATG ACACCGTTCA ACCTGACAGT
 451 ATTATTGAAA AGGCTTCTCA CTCGGGCATG ATCAACCCCA GCCGGCAGTG
 501 GCAGACGCTG AAGCAGAACA CGGGCGTTGC CCACTTTGAG TATCAGATCC
 551 GCGTGACCTG TGATGACTAC TACTATGGCT TTGGCTGYAA TAAGTTCTGC
 601 CGCCCAGAG  ATGACTTCTT TGGACACTAT GCCTGTGACC AGAATGGCAA
 651 CAAAACTTGC ATGGAAGGCT GGATGGGCCC CGAATGTAAC AGAGCTATTT
 701 GCCGACAAGG CTGCAGTCCT AAGCATGGGT CTTGCAAACT CCCAGGTGAC
 751 TGCAGGTGCC AGTAYGGCTG GCAAGGCCTG TACTGTGATA AGTGCATCCC
 801 ACACCGGGA  TGCGTCCACG GCATCTGTAA TGAGCCCTGG CAGTGCCTCT
 851 GTGAGACCAA CTGGGGCGGC CAGCTCTGTG ACAAAGATCT CAATTACTGT
 901 GGGACTCATC AGCCGTGTCT CAACGGGGA  ACTTGTAGCA ACACAGGCCC
 951 TGACAAATAT CAGTGTTCCT GCCCTGAGGG GTATTCAGGA CCCAACTGTG
1001 AAATTGCTGA GCACGCCTGC CTCTCTGATC CCTGTCACAA CAGAGGCAGC
1051 TGTAAGGAGA CCTCCCTGGG CTTTGAGTGT GAGTGTTCCC CAGGCTGGAC
1101 CGGCCCCACA TGCTCTACAA ACATTGATGA CTGTTCTCCT AATAACTGTT
1151 CCCACGGGGG CACCTGCCAG GACCTGGTTA ACGGATTTAA GTGTGTGTGC
1201 CCCCACAGT  GGACTGGGAA AACGTGCCAG TTAGATGCAA ATGAATGTGA
1251 GGCCAAACCT TGTGTAAACG CCAAATCCTG TAAGAATCTC ATTGCCAGCT
1301 ACTACTGCGA CTGTCTTCCC GGCTGGATGG GTCAGAATTG TGACATAAAT
1351 ATTAATGACT GCCTTGGCCA GTGTCAGAAT GACGCCTCCT GTCGGGATTT
1401 GGTTAATGGT TATCGCTGTA TCTGTCCACC TGGCTATGCA GGCGATCACT
1451 GTGAGAGAGA CATCGATGAA TGTGCCAGCA ACCCCTGTTT GAATGGGGGT
1501 CACTGTCAGA ATGAAATCAA CAGATTCCAG TGTCTGTGTC CCACTGGTTT
1551 CTCTGGAAAC TCTGTCAGC  TGGACATCGA TTATTGTGAG CCTAATCCCT
1601 GCCAGAACGG TGCCCAGTGC TACAACCGTG CCAGTGACTA TTTCTGCAAG
1651 TGCCCCGAGG ACTATGAGGG CAAGAACTGC TCACACCTGA AAGACCACTG
1701 CCGCACGACC CCCTGTGAAG TGATTGACAG CTGCACAGTG GCCATGGCTT
1751 CCAACGACAC ACCTGAAGGG GTGCGGTATA TTTCCTCCAA CGTCTGTGGT
1801 CCTCACGGGA AGTGCAAGAG TCAGTCGGGA GGCAAATTCA CCTGTGACTG
1851 TAACAAAGGC TTCACGGGAA CATACTGCCA TGAAAATATT AATGACTGTG
1901 AGAGCAACCC TTGTAGAAAC GGTGGCACTT GCATCGATGG TGTCAACTCC
1951 TACAAGTGCA TCTGTAGTGA CGGCTGGGAG GGGGCCTACT GTGAAACCAA
2001 TATTAATGAC TGCAGCCAGA ACCCCTGCCA CAATGGGGGC ACGTGTCGCG
```

FIG. 8B

```
2051 ACCTGGTCAA TGACTTCTAC TGTGACTGTA AAAATGGGTG GAAAGGAAAG
2101 ACCTGCCACT CACGTGACAG TCAGTGTGAT GAGGCCACGT GCAACAACGG
2151 TGGCACCTGC TATGATGAGG GGGATGCTTT TAAGTGCATG TGTCCTGGCG
2201 GCTGGGAAGG AACAACCTGT AACATAGCCC GAAACAGTAG CTGCCTGCCC
2251 AACCCCTGCC ATAATGGGGG CACATGTGTG GTCAACGGCG AGTCCTTTAC
2301 GTGCGTCTGC AAGGAAGGCT GGGAGGGGCC CATCTGTGCT CAGAATACCA
2351 ATGACTGCAG CCCTCATCCC TGTTACAACA GCGGCACCTG TGTGGATGGA
2401 GACAACTGGT ACCGGTGCGA ATGTGCCCCG GGTTTTGCTG GGCCCGACTG
2451 CAGAATAAAC ATCAATGAAT GCCAGTCTTC ACCTTGTGCC TTTGGAGCGA
2501 CCTGTGTGGA TGAGATCAAT GGCTACCGGT GTGTCTGCCC TCCAGGGCAC
2551 AGTGGTGCCA AGTGCCAGGA AGTTTCAGGG AGACCTTGCA TCACCATGGG
2601 GAGTGTGATA CCAGATGGGG CCAAATGGGA TGATGACTGT AATACCTGCC
2651 AGTGCCTGAA TGGACGGATC GCCTGCTCAA AGGTCTGGTG TGGCCCTCGA
2701 CCTTGCCTGC TCCACAAAGG GCACAGCGAG TGCCCAGCG GGCAGAGCTG
2751 CATCCCCATC CTGGACGACC AGTGCTTCGT CCACCCCTGC ACTGGTGTGG
2801 GCGAGTGTCG GTCTTCCAGT CTCCAGCCGG TGAAGACAAA GTGCACCTCT
2851 GACTCCTATT ACCAGGATAA CTGTGCGAAC ATCACATTTA CCTTTAACAA
2901 GGAGATGATG TCACCAGGTC TTACTACGGA GCACATTTGC AGTGAATTGA
2951 GGAATTTGAA TATTTTGAAG AATGTTTCCG CTGAATATTC AATCTACATC
3001 GCTTGCGAGC CTTCCCCTTC AGCGAACAAT GAAATACATG TGGCCATTTC
3051 TGCTGAAGAT ATACGGGATG ATGGAACCC GATCAAGGAA ATCACTGACA
3101 AAATAATCGA TCTTGTTAGT AAACGTGATG GAAACAGCTC GCTGATTGCT
3151 GCCGTTGCAG AAGTAAGAGT TCAGAGGCGG CCTCTGAAGA ACAGAACAGA
3201 TTTCCTTGTT CCCTTGCTGA GCTCTGTCTT AACTGTGGCT TGGATCTGTT
3251 GCTTGGTGAC GGCCTTCTAC TGGTGCCTGC GGAAGCGGCG GAAGCCGGGC
3301 AGCCACACAC ACTCAGCCTC TGAGGACAAC ACCACCAACA ACGTGCGGGA
3351 GCAGCTGAAC CAGATCAAAA ACCCCATTGA GAAACATGGG GCCAACACGG
3401 TCCCCATCAA GGATTACGAG AACAAGAACT CCAAAATGTC TAAAATAAGG
3451 ACACACAATT CTGAAGTAGA AGAGGACGAC ATGGACAAAC ACCAGCAGAA
3501 AGCCCGGTTT GGCAAGCAGC CGGCGTATAC GCTGGTAGAC AGAGAAGAGA
3551 AGCCCCCCAA CGGCACGCCG ACAAAACACC CAAACTGGAC AAACAAACAG
3601 GACAACAGAG ACTTGGAAAG TGCCCAGAGC TTAAACCGAA TGGAGTACAT
3651 CGTATAG
```

FIG. 8C

```
   1  MRSPRTRGRS RPLSLLLALL CALRAKVCGA SGQFELEILS MQNVNGELQN
  51  GNCCGGARNP GDRKCTRDEC DTYFKVCLKE YQSRVTAGGP CSFGSGSTPV
 101  IGGNTFNLKA SRGNDRNRIV LPFSFAWPRS YTLLVEAWDS SNDTVQPDSI
 151  IEKASHSGMI NPSRQWQTLK QNTGVAHFEY QIRVTCDDYY YGFGCNKFCR
 201  PRDDFFGHYA CDQNGNKTCM EGWMGPECNR AICRQGCSPK HGSCKLPGDC
 251  RCQYGWQGLY CDKCIPHPGC VHGICNEPWQ CLCETNWGGQ LCDKDLNYCG
 301  THQPCLNGGT CSNTGPDKYQ CSCPEGYSGP NCEIAEHACL SDPCHNRGSC
 351  KETSLGFECE CSPGWTGPTC STNIDDCSPN NCSHGGTCQD LVNGFKCVCP
 401  PQWTGKTCQL DANECEAKPC VNAKSCKNLI ASYYCDCLPG WMGQNCDINI
 451  NDCLGQCQND ASCRDLVNGY RCICPPGYAG DHCERDIDEC ASNPCLNGGH
 501  CQNEINRFQC LCPTGFSGNL CQLDIDYCEP NPCQNGAQCY NRASDYFCKC
 551  PEDYEGKNCS HLKDHCRTTP CEVIDSCTVA MASNDTPEGV RYISSNVCGP
 601  HGKCKSQSGG KFTCDCNKGF TGTYCHENIN DCESNPCRNG GTCIDGVNSY
 651  CICSDGWEGA YCETNINDCS QNPCHNGGTC RDLVNDFYCD CKNGWKGKTC
 701  HSRDSQCDEA TCNNGGTCYD EGDAFKCMCP GGWEGTTCNI ARNSSCLPNP
 751  CHNGGTCVVN GESFTCVCKE GWEGPICAQN TNDCSPHPCY NSGTCVDGDN
 801  WYRCECAPGF AGPDCRININ ECQSSPCAFG ATCVDEINGY RCVCPPGHSG
 851  AKCQEVSGRP CITMGSVIPD GAKWDDDCNT CQCLNGRIAC SKVWCGPRPC
 901  LLHKGHSECP SGQSCIPILD DQCFVHPCTG VGECRSSSLQ PVKTKCTSDS
 951  YYQDNCANIT FTFNKEMMSP GLTTEHICSE LRNLNILKNV SAEYSIYIAC
1001  EPSPSANNEI HVAISAEDIR DDGNPIKEIT DKIIDLVSKR DGNSSLIAAV
1051  AEVRVQRRPL KNRTD
```

FIG. 13A

```
   1 ATGCGTTCCC CACGGACRCG CGGCCGGTCC GGGCGCCCCC TAAGCCTCCT
  51 GCTCGCCCTG CTCTGTGCCC TGCGAGCCAA GGTGTGTGGG GCCTCGGGTC
 101 AGTTCGAGTT GGAGATCCTG TCCATGCAGA ACGTGAACGG GGAGCTGCAG
 151 AACGGGAACT GCTGCGGCGG CGCCCGGAAC CCGGGAGACC GCAAGTGCAC
 201 CCGCGACGAG TGTGACACAT ACTTCAAAGT GTGCCTCAAG GAGTATCAGT
 251 CCCGCGTCAC GGCCGGGGGG CCCTGCAGCT TCGGCTCAGG GTCCACGCCT
 301 GTCATCGGGG GCAACACCTT CAACCTCAAG GCCAGCCGCG GCAACGACCG
 351 CAACCGCATC GTGCTGCCTT TCAGTTTCGC CTGGCCGAGG TCCTATACGT
 401 TGCTTGTGGA GGCGTGGGAT CCAGTAATG ACACCGTTCA ACCTGACAGT
 451 ATTATTGAAA AGGCTTCTCA CTCGGGCATG ATCAACCCCA GCCGGCAGTG
 501 GCAGACGCTG AAGCAGAACA CGGGCGTTGC CCACTTTGAG TATCAGATCC
 551 GCGTGACCTG TGATGACTAC TACTATGGCT TTGGCTGYAA TAAGTTCTGC
 601 CGCCCCAGAG ATGACTTCTT TGGACACTAT GCCTGTGACC AGAATGGCAA
 651 CAAAACTTGC ATGGAAGGCT GGATGGGCCC CGAATGTAAC AGAGCTATTT
 701 GCCGACAAGG CTGCAGTCCT AAGCATGGGT CTTGCAAACT CCCAGGTGAC
 751 TGCAGGTGCC AGTAYGGCTG GCAAGGCCTG TACTGTGATA AGTGCATCCC
 801 ACACCGGGA TGCGTCCACG GCATCTGTAA TGAGCCCTGG CAGTGCCTCT
 851 GTGAGACCAA CTGGGGCGGC CAGCTCTGTG ACAAAGATCT CAATTACTGT
 901 GGGACTCATC AGCCGTGTCT CAACGGGGA ACTTGTAGCA ACACAGGCCC
 951 TGACAAATAT CAGTGTTCCT GCCCTGAGGG GTATTCAGGA CCCAACTGTG
1001 AAATTGCTGA GCACGCCTGC CTCTCTGATC CCTGTCACAA CAGAGGCAGC
1051 TGTAAGGAGA CCTCCCTGGG CTTTGAGTGT GAGTGTTCCC CAGGCTGGAC
1101 CGGCCCCACA TGCTCTACAA ACATTGATGA CTGTTCTCCT AATAACTGTT
1151 CCCACGGGGG CACCTGCCAG GACCTGGTTA ACGGATTTAA GTGTGTGTGC
1201 CCCCCACAGT GGACTGGGAA AACGTGCCAG TTAGATGCAA ATGAATGTGA
1251 GGCCAAACCT TGTGTAAACG CCAAATCCTG TAAGAATCTC ATTGCCAGCT
1301 ACTACTGCGA CTGTCTTCCC GGCTGGATGG GTCAGAATTG TGACATAAAT
1351 ATTAATGACT GCCTTGGCCA GTGTCAGAAT GACGCCTCCT GTCGGGATTT
1401 GGTTAATGGT TATCGCTGTA TCTGTCCACC TGGCTATGCA GGCGATCACT
1451 GTGAGAGAGA CATCGATGAA TGTGCCAGCA ACCCTGTTT GAATGGGGGT
```

FIG. 13B

```
1501 CACTGTCAGA ATGAAATCAA CAGATTCCAG TGTCTGTGTC CCACTGGTTT
1551 CTCTGGAAAC CTCTGTCAGC TGGACATCGA TTATTGTGAG CCTAATCCCT
1601 GCCAGAACGG TGCCCAGTGC TACAACCGTG CCAGTGACTA TTTCTGCAAG
1651 TGCCCCGAGG ACTATGAGGG CAAGAACTGC TCACACCTGA AAGACCACTG
1701 CCGCACGACC CCCTGTGAAG TGATTGACAG CTGCACAGTG GCCATGGCTT
1751 CCAACGACAC ACCTGAAGGG GTGCGGTATA TTTCCTCCAA CGTCTGTGGT
1801 CCTCACGGGA AGTGCAAGAG TCAGTCGGGA GGCAAATTCA CCTGTGACTG
1851 TAACAAAGGC TTCACGGGAA CATACTGCCA TGAAAATATT AATGACTGTG
1901 AGAGCAACCC TTGTAGAAAC GGTGGCACTT GCATCGATGG TGTCAACTCC
1951 TACAAGTGCA TCTGTAGTGA CGGCTGGGAG GGGGCCTACT GTGAAACCAA
2001 TATTAATGAC TGCAGCCAGA ACCCCTGCCA CAATGGGGGC ACGTGTCGCG
2051 ACCTGGTCAA TGACTTCTAC TGTGACTGTA AAAATGGGTG GAAAGGAAAG
2101 ACCTGCCACT CACGTGACAG TCAGTGTGAT GAGGCCACGT GCAACAACGG
2151 TGGCACCTGC TATGATGAGG GGGATGCTTT TAAGTGCATG TGTCCTGGCG
2201 GCTGGGAAGG AACAACCTGT AACATAGCCC GAAACAGTAG CTGCCTGCCC
2251 AACCCCTGCC ATAATGGGGG CACATGTGTG GTCAACGGCG AGTCCTTTAC
2301 GTGCGTCTGC AAGGAAGGCT GGGAGGGGCC CATCTGTGCT CAGAATACCA
2351 ATGACTGCAG CCCTCATCCC TGTTACAACA GCGGCACCTG TGTGGATGGA
2401 GACAACTGGT ACCGGTGCGA ATGTGCCCCG GGTTTTGCTG GGCCCGACTG
2451 CAGAATAAAC ATCAATGAAT GCCAGTCTTC ACCTTGTGCC TTTGGAGCGA
2501 CCTGTGTGGA TGAGATCAAT GGCTACCGGT GTGTCTGCCC TCCAGGGCAC
2551 AGTGGTGCCA AGTGCCAGGA AGTTTCAGGG AGACCTTGCA TCACCATGGG
2601 GAGTGTGATA CCAGATGGGG CCAAATGGGA TGATGACTGT AATACCTGCC
2651 AGTGCCTGAA TGGACGGATC GCCTGCTCAA AGGTCTGGTG TGGCCCTCGA
2701 CCTTGCCTGC TCCACAAAGG GCACAGCGAG TGCCCCAGCG GGCAGAGCTG
2751 CATCCCCATC CTGGACGACC AGTGCTTCGT CCACCCCTGC ACTGGTGTGG
2801 GCGAGTGTCG GTCTTCCAGT CTCCAGCCGG TGAAGACAAA GTGCACCTCT
2851 GACTCCTATT ACCAGGATAA CTGTGCGAAC ATCACATTTA CCTTTAACAA
2901 GGAGATGATG TCACCAGGTC TTACTACGGA GCACATTTGC AGTGAATTGA
2951 GGAATTTGAA TATTTTGAAG AATGTTTCCG CTGAATATTC AATCTACATC
3001 GCTTGCGAGC CTTCCCCTTC AGCGAACAAT GAAATACATG TGGCCATTTC
3051 TGCTGAAGAT ATACGGGATG ATGGGAACCC GATCAAGGAA ATCACTGACA
3101 AATAATCGA TCTTGTTAGT AAACGTGATG GAAACAGCTC GCTGATTGCT
3151 GCCGTTGCAG AAGTAAGAGT TCAGAGGCGG CCTCTGAAGA ACAGAACAGA
3201 T
```

FIG. 13C

SEQUENCE LISTING

<160> NUMBER OF SEQ ID NOS: 56

<210> SEQ ID NO 1
<211> LENGTH: 1218
<212> TYPE: PRT
<213> ORGANISM: Homo sapiens

<400> SEQUENCE: 1

Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser

```
                 100                 105                 110
Arg Gly Asn Asp Arg Asn Arg Ile Val Leu Pro Phe Ser Phe Ala Trp
            115                 120                 125

Pro Arg Ser Tyr Thr Leu Leu Val Glu Ala Trp Asp Ser Ser Asn Asp
        130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Leu Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
    370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Lys Ser Cys Lys Asn Leu Ile Ala
            420                 425                 430

Ser Tyr Tyr Cys Asp Cys Leu Pro Gly Trp Met Gly Gln Asn Cys Asp
        435                 440                 445

Ile Asn Ile Asn Asp Cys Leu Gly Gln Cys Gln Asn Asp Ala Ser Cys
    450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525
```

-continued

Cys Glu Pro Asn Pro Cys Gln Asn Gly Ala Gln Cys Tyr Asn Arg Ala
    530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
        595                 600                 605

Ser Gly Gly Lys Phe Thr Cys Asp Cys Asn Lys Gly Phe Thr Gly Thr
    610                 615                 620

Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala Tyr Cys Glu Thr Asn Ile Asn Asp Cys Ser
            660                 665                 670

Gln Asn Pro Cys His Asn Gly Gly Thr Cys Arg Asp Leu Val Asn Asp
        675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Glu Ser Phe Thr Cys
        755                 760                 765

Val Cys Lys Glu Gly Trp Glu Gly Pro Ile Cys Ala Gln Asn Thr Asn
    770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Arg Cys Val Cys Pro Pro
        835                 840                 845

Gly His Ser Gly Ala Lys Cys Gln Glu Val Ser Gly Arg Pro Cys Ile
    850                 855                 860

Thr Met Gly Ser Val Ile Pro Asp Gly Ala Lys Trp Asp Asp Asp Cys
865                 870                 875                 880

Asn Thr Cys Gln Cys Leu Asn Gly Arg Ile Ala Cys Ser Lys Val Trp
                885                 890                 895

Cys Gly Pro Arg Pro Cys Leu Leu His Lys Gly His Ser Glu Cys Pro
            900                 905                 910

Ser Gly Gln Ser Cys Ile Pro Ile Leu Asp Asp Gln Cys Phe Val His
        915                 920                 925

Pro Cys Thr Gly Val Gly Glu Cys Arg Ser Ser Ser Leu Gln Pro Val
    930                 935                 940

```
Lys Thr Lys Cys Thr Ser Asp Ser Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile Ala Cys Glu Pro Ser Pro Ser Ala
        995                 1000                1005

Asn Asn Glu Ile His Val Ala Ile Ser Ala Glu Asp Ile Arg Asp
    1010                1015                1020

Asp Gly Asn Pro Ile Lys Glu Ile Thr Asp Lys Ile Ile Asp Leu
    1025                1030                1035

Val Ser Lys Arg Asp Gly Asn Ser Ser Leu Ile Ala Ala Val Ala
    1040                1045                1050

Glu Val Arg Val Gln Arg Arg Pro Leu Lys Asn Arg Thr Asp Phe
    1055                1060                1065

Leu Val Pro Leu Leu Ser Ser Val Leu Thr Val Ala Trp Ile Cys
    1070                1075                1080

Cys Leu Val Thr Ala Phe Tyr Trp Cys Leu Arg Lys Arg Arg Lys
    1085                1090                1095

Pro Gly Ser His Thr His Ser Ala Ser Glu Asp Asn Thr Thr Asn
    1100                1105                1110

Asn Val Arg Glu Gln Leu Asn Gln Ile Lys Asn Pro Ile Glu Lys
    1115                1120                1125

His Gly Ala Asn Thr Val Pro Ile Lys Asp Tyr Glu Asn Lys Asn
    1130                1135                1140

Ser Lys Met Ser Lys Ile Arg Thr His Asn Ser Glu Val Glu Glu
    1145                1150                1155

Asp Asp Met Asp Lys His Gln Gln Lys Ala Arg Phe Gly Lys Gln
    1160                1165                1170

Pro Ala Tyr Thr Leu Val Asp Arg Glu Glu Lys Pro Pro Asn Gly
    1175                1180                1185

Thr Pro Thr Lys His Pro Asn Trp Thr Asn Lys Gln Asp Asn Arg
    1190                1195                1200

Asp Leu Glu Ser Ala Gln Ser Leu Asn Arg Met Glu Tyr Ile Val
    1205                1210                1215

<210> SEQ ID NO 2
<211> LENGTH: 3657
<212> TYPE: DNA
<213> ORGANISM: Homo sapiens

<400> SEQUENCE: 2
atgcgttccc cacggacrcg cggccggtcc gggcgccccc taagcctcct gctcgccctg      60
ctctgtgccc tgcgagccaa ggtgtgtggg gcctcgggtc agttcgagtt ggagatcctg     120
tccatgcaga acgtgaacgg ggagctgcag aacgggaact gctgcggcgg cgcccggaac     180
ccgggagacc gcaagtgcac ccgcgacgag tgtgacacat acttcaaagt gtgcctcaag     240
gagtatcagt cccgcgtcac ggccgggggg ccctgcagct tcggctcagg gtccacgcct     300
gtcatcgggg gcaacacctt caacctcaag gccagccgcg gcaacgaccg caaccgcatc     360
gtgctgcctt tcagtttcgc ctggccgagg tcctatacgt tgcttgtgga ggcgtgggat     420
tccagtaatg acaccgttca acctgacagt attattgaaa aggcttctca ctcgggcatg     480
atcaacccca gccggcagtg gcagacgctg aagcagaaca cggggcgttgc ccactttgag     540
```

-continued

```
tatcagatcc gcgtgacctg tgatgactac tactatggct ttggctgyaa taagttctgc      600
cgccccagag atgacttctt tggacactat gcctgtgacc agaatggcaa caaaacttgc      660
atggaaggct ggatgggccc cgaatgtaac agagctattt gccgacaagg ctgcagtcct      720 aagcatggt  cttgcaaact cccaggtgac tgcaggtgcc agtayggctg gcaaggcctg      780
tactgtgata agtgcatccc acacccggga tgcgtccacg gcatctgtaa tgagccctgg      840
cagtgcctct gtgagaccaa ctggggcggc cagctctgtg acaaagatct caattactgt      900
gggactcatc agccgtgtct caacggggga acttgtagca cacaggccc  tgacaaatat      960 cagtgttcct gccctgaggg gtattcagga cccaactgtg aaattgctga gcacgcctgc     1020
ctctctgatc cctgtcacaa cagaggcagc tgtaaggaga cctccctggg ctttgagtgt     1080
gagtgttccc caggctggac cggccccaca tgctctacaa acattgatga ctgttctcct     1140
aataactgtt cccacggggg cacctgccag gacctggtta acggatttaa gtgtgtgtgc     1200
cccccacagt ggactgggaa aacgtgccag ttagatgcaa atgaatgtga ggccaaacct     1260
tgtgtaaacg ccaaatcctg taagaatctc attgccagct actactgcga ctgtcttccc     1320
ggctggatgg gtcagaattg tgacataaat attaatgact gccttggcca gtgtcagaat     1380
gacgcctcct gtcgggattt ggttaatggt tatcgctgta tctgtccacc tggctatgca     1440
ggcgatcact gtgagagaga catcgatgaa tgtgccagca cccctgtttt gaatggggt      1500 cactgtcaga atgaaatcaa cagattccag tgtctgtgtc ccactggttt ctctggaaac     1560
ctctgtcagc tggacatcga ttattgtgag cctaatccct gccagaacgg tgcccagtgc     1620
tacaaccgtg ccagtgacta tttctgcaag tgccccgagg actatgaggg caagaactgc     1680
tcacacctga agaccactg  ccgcacgacc ccctgtgaag tgattgacag ctgcacagtg     1740
gccatggctt ccaacgacac acctgaaggg gtgcggtata tttcctccaa cgtctgtggt     1800
cctcacggga agtgcaagag tcagtcggga ggcaaattca cctgtgactg taacaaaggc     1860
ttcacgggaa catactgcca tgaaaatatt aatgactgtg agagcaaccc ttgtagaaac     1920
ggtggcactt gcatcgatgg tgtcaactcc tacaagtgca tctgtagtga cggctgggag     1980
ggggcctact gtgaaaccaa tattaatgac tgcagccaga acccctgcca caatgggggc     2040
acgtgtcgcg acctggtcaa tgacttctac tgtgactgta aaaatgggtg gaaaggaaag     2100
acctgccact cacgtgacag tcagtgtgat gaggccacgt gcaacaacgg tggcacctgc     2160
tatgatgagg gggatgcttt taagtgcatg tgtcctggcg gctgggaagg aacaacctgt     2220
aacatagccc gaaacagtag ctgcctgccc aaccctgcc  ataatggggg cacatgtgtg     2280
gtcaacggcg agtcctttac gtgcgtctgc aaggaaggct gggagggcc  catctgtgct     2340 cagaatacca atgactgcag ccctcatccc tgttacaaca gcggcacctg tgtggatgga     2400
gacaactggt accggtgcga atgtgccccg gttttgctg  gcccgactg  cagaataaac     2460 atcaatgaat gccagtcttc accttgtgcc tttggagcga cctgtgtgga tgagatcaat     2520
ggctaccggt gtgtctgccc tccagggcac agtggtgcca agtgccagga gtttcaggg      2580 agaccttgca tcaccatggg gagtgtgata ccagatgggg ccaaatggga tgatgactgt     2640
aatacctgcc agtgcctgaa tggacggatc gcctgctcaa aggtctggtg tggccctcga     2700
ccttgcctgc tccacaaagg gcacagcgag tgccccagcg gcagagctg  catccccatc     2760 ctggacgacc agtgcttcgt ccaccctgc  actggtgtgg gcgagtgtcg gtcttccagt     2820
ctccagccgg tgaagacaaa gtgcacctct gactcctatt accaggataa ctgtgcgaac     2880
```

```
atcacattta cctttaacaa ggagatgatg tcaccaggtc ttactacgga gcacatttgc    2940
agtgaattga ggaatttgaa tattttgaag aatgtttccg ctgaatattc aatctacatc    3000
gcttgcgagc cttccccttc agcgaacaat gaaatacatg tggccatttc tgctgaagat    3060
atacgggatg atgggaaccc gatcaaggaa atcactgaca aaataatcga tcttgttagt    3120
aaacgtgatg gaaacagctc gctgattgct gccgttgcag aagtaagagt tcagaggcgg    3180
cctctgaaga acagaacaga tttccttgtt cccttgctga gctctgtctt aactgtggct    3240
tggatctgtt gcttggtgac ggccttctac tggtgcctgc ggaagcggcg gaagccgggc    3300
agccacacac actcagcctc tgaggacaac accaccaaca acgtgcggga gcagctgaac    3360
cagatcaaaa accccattga gaaacatggg gccaacacgg tccccatcaa ggattacgag    3420
aacaagaact ccaaaatgtc taaataagg acacacaatt ctgaagtaga agaggacgac    3480
atggacaaac accagcagaa agcccggttt ggcaagcagc cggcgtatac gctggtagac    3540
agagaagaga agcccccccaa cggcacgccg acaaaacacc caaactggac aaacaaacag    3600
gacaacagag acttggaaag tgcccagagc ttaaaccgaa tggagtacat cgtatag       3657
```

<210> SEQ ID NO 3  
<211> LENGTH: 22  
<212> TYPE: DNA  
<213> ORGANISM: Artificial Sequence  
<220> FEATURE:  
<223> OTHER INFORMATION: PCR primer

<400> SEQUENCE: 3
gcgcaagctt tttttttttt cg                                              22

<210> SEQ ID NO 4  
<211> LENGTH: 18  
<212> TYPE: DNA  
<213> ORGANISM: Artificial Sequence  
<220> FEATURE:  
<223> OTHER INFORMATION: PCR primer

<400> SEQUENCE: 4
gagaccgtga agatactt                                                   18

<210> SEQ ID NO 5  
<211> LENGTH: 20  
<212> TYPE: DNA  
<213> ORGANISM: Artificial Sequence  
<220> FEATURE:  
<223> OTHER INFORMATION: PCR primer

<400> SEQUENCE: 5
ccgactgcag aataaacatc                                                 20

<210> SEQ ID NO 6  
<211> LENGTH: 20  
<212> TYPE: DNA  
<213> ORGANISM: Artificial Sequence  
<220> FEATURE:  
<223> OTHER INFORMATION: PCR primer

<400> SEQUENCE: 6
ttggatctgg ttcagctgct                                                 20

<210> SEQ ID NO 7  
<211> LENGTH: 20  
<212> TYPE: DNA  
<213> ORGANISM: Artificial Sequence

```
<220> FEATURE:
<223> OTHER INFORMATION: PCR primer

<400> SEQUENCE: 7
ttcagtgacg gccactgtga                                                   20

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
cacgtacatg aagtgcagct                                                   20

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
tgagtaggct ccatccagtc                                                   20

<210> SEQ ID NO 10
<211> LENGTH: 20
<212> TYPE: DNA
<213> ORGANISM: Artificial Sequence
<220> FEATURE:
<223> OTHER INFORMATION: PCR primer

<400> SEQUENCE: 10
tggtgtcagg tagggatgct                                                   20

<210> SEQ ID NO 11
<211> LENGTH: 24
<212> TYPE: DNA
<213> ORGANISM: Artificial Sequence
<220> FEATURE:
<223> OTHER INFORMATION: PCR primer

<400> SEQUENCE: 11
ccacccatgg caaattccat ggca                                              24

<210> SEQ ID NO 12
<211> LENGTH: 24
<212> TYPE: DNA
<213> ORGANISM: Artificial Sequence
<220> FEATURE:
<223> OTHER INFORMATION: PCR primer

<400> SEQUENCE: 12
tctagacggc aggtcaggtc cacc                                              24

<210> SEQ ID NO 13
<211> LENGTH: 36
<212> TYPE: DNA
<213> ORGANISM: Artificial Sequence
<220> FEATURE:
<223> OTHER INFORMATION: PCR primer

<400> SEQUENCE: 13
gactatgcga attcggatcc gtcgacgcca ccatgg                                 36
```

<210> SEQ ID NO 14
<211> LENGTH: 20
<212> TYPE: DNA
<213> ORGANISM: Artificial Sequence
<220> FEATURE:
<223> OTHER INFORMATION: PCR primer

<400> SEQUENCE: 14
caagttcccc cgttgagaca                                          20

<210> SEQ ID NO 15
<211> LENGTH: 65
<212> TYPE: DNA
<213> ORGANISM: Artificial Sequence
<220> FEATURE:
<223> OTHER INFORMATION: PCR primer

<400> SEQUENCE: 15
gcatagtcct cgagttacaa gtcttcttca gaaataagct tttgttctac gatgtactcc    60
attcg                                                          65

<210> SEQ ID NO 16
<211> LENGTH: 20
<212> TYPE: DNA
<213> ORGANISM: Artificial Sequence
<220> FEATURE:
<223> OTHER INFORMATION: PCR primer

<400> SEQUENCE: 16
atggacaaac accagcagaa                                          20

<210> SEQ ID NO 17
<211> LENGTH: 3201
<212> TYPE: DNA
<213> ORGANISM: Homo sapiens

<400> SEQUENCE: 17
atgcgttccc cacggacrcg cggccggtcc gggcgccccc taagcctcct gctcgccctg    60
ctctgtgccc tgcgagccaa ggtgtgtggg gcctcgggtc agttcgagtt ggagatcctg   120
tccatgcaga acgtgaacgg ggagctgcag aacgggaact gctgcggcgg cgcccggaac   180
ccgggagacc gcaagtgcac ccgcgacgag tgtgacacat acttcaaagt gtgcctcaag   240
gagtatcagt cccgcgtcac ggccgggggg ccctgcagct tcggctcagg gtccacgcct   300
gtcatcgggg gcaacacctt caacctcaag gccagccgcg gcaacgaccg caaccgcatc   360
gtgctgcctt tcagtttcgc ctggccgagg tcctatacgt tgcttgtgga ggcgtgggat   420
tccagtaatg acaccgttca acctgacagt attattgaaa aggcttctca ctcgggcatg   480
atcaaccccg gccggcagtg gcagacgctg aagcagaaca cgggcgttgc ccactttgag   540
tatcagatcc gcgtgaccctg tgatgactac tactatggct ttggctgyaa taagttctgc   600
cgccccagag atgacttctt tggacactat gcctgtgacc agaatggcaa caaaacttgc   660
atggaaggct ggatgggccc cgaatgtaac agagctattt gccgacaagg ctgcagtcct   720
aagcatgggt cttgcaaact cccaggtgac tgcaggtgcc agtayggctg gcaaggcctg   780
tactgtgata agtgcatccc acacccggga tgcgtccacg gcatctgtaa tgagccctgg   840
cagtgcctct gtgagaccaa ctggggcggc cagctctgtg acaaagatct caattactgt   900
gggactcatc agccgtgtct caacgggggga acttgtagca acacaggccc tgacaaatat   960
cagtgttcct gccctgaggg gtattcagga cccaactgtg aaattgctga gcacgcctgc  1020

-continued

```
ctctctgatc cctgtcacaa cagaggcagc tgtaaggaga cctccctggg ctttgagtgt    1080
gagtgttccc caggctggac cggccccaca tgctctacaa acattgatga ctgttctcct    1140
aataactgtt cccacggggg cacctgccag gacctggtta acggatttaa gtgtgtgtgc    1200
cccccacagt ggactgggaa aacgtgccag ttagatgcaa atgaatgtga ggccaaacct    1260
tgtgtaaacg ccaaatcctg taagaatctc attgccagct actactgcga ctgtcttccc    1320
ggctggatgg gtcagaattg tgacataaat attaatgact gccttggcca gtgtcagaat    1380
gacgcctcct gtcgggattt ggttaatggt tatcgctgta tctgtccacc tggctatgca    1440
ggcgatcact gtgagagaga catcgatgaa tgtgccagca cccctgtttt gaatgggggt    1500
cactgtcaga atgaaatcaa cagattccag tgtctgtgtc ccactggttt ctctggaaac    1560
ctctgtcagc tggacatcga ttattgtgag cctaatccct gccagaacgg tgcccagtgc    1620
tacaaccgtg ccagtgacta tttctgcaag tgccccgagg actatgaggg caagaactgc    1680
tcacacctga agaccactg ccgcacgacc cctgtgaag tgattgacag ctgcacagtg    1740
gccatggctt ccaacgacac acctgaaggg gtgcggtata tttcctccaa cgtctgtggt    1800
cctcacggga agtgcaagag tcagtcggga ggcaaattca cctgtgactg taacaaaggc    1860
ttcacgggaa catactgcca tgaaaatatt aatgactgtg agagcaaccc ttgtagaaac    1920
ggtggcactt gcatcgatgg tgtcaactcc tacaagtgca tctgtagtga cggctgggag    1980
ggggcctact gtgaaaccaa tattaatgac tgcagccaga cccctgcca caatgggggc    2040 acgtgtcgcg acctggtcaa tgacttctac tgtgactgta aaaatgggtg gaaaggaaag    2100
acctgccact cacgtgacag tcagtgtgat gaggccacgt gcaacaacgg tggcacctgc    2160
tatgatgagg gggatgcttt taagtgcatg tgtcctggcg gctgggaagg aacaacctgt    2220
aacatagccc gaaacagtag ctgcctgccc aaccccctgcc ataatggggg cacatgtgtg    2280
gtcaacggcg agtcctttac gtgcgtctgc aaggaaggct gggagggggcc catctgtgct    2340 cagaatacca atgactgcag ccctcatccc tgttacaaca gcggcacctg tgtggatgga    2400
gacaactggt accggtgcga atgtgccccg ggttttgctg ggcccgactg cagaataaac    2460
atcaatgaat gccagtcttc accttgtgcc tttggagcga cctgtgtgga tgagatcaat    2520
ggctaccggt gtgtctgccc tccagggcac agtggtgcca agtgccagga gtttcaggg    2580 agaccttgca tcaccatggg gagtgtgata ccagatgggg ccaaatggga tgatgactgt    2640
aatacctgcc agtgcctgaa tggacggatc gcctgctcaa aggtctggtg tggccctcga    2700
ccttgcctgc tccacaaagg gcacagcgag tgccccagcg ggcagagctg catccccatc    2760
ctggacgacc agtgcttcgt ccaccccctgc actggtgtgg gcgagtgtcg gtcttccagt    2820
ctccagccgg tgaagacaaa gtgcacctct gactcctatt accaggataa ctgtgcgaac    2880
atcacattta cctttaacaa ggagatgatg tcaccaggtc ttactacgga gcacatttgc    2940
agtgaattga ggaatttgaa tattttgaag aatgtttccg ctgaatattc aatctacatc    3000
gcttgcgagc cttcccttc agcgaacaat gaaatacatg tggccatttc tgctgaagat    3060
atacgggatg atgggaaccc gatcaaggaa atcactgaca aaataatcga tcttgttagt    3120
aaacgtgatg gaaacagctc gctgattgct gccgttgcag aagtaagagt tcagaggcgg    3180
cctctgaaga acagaacaga t                                              3201
```

<210> SEQ ID NO 18
<211> LENGTH: 1067
<212> TYPE: PRT

<213> ORGANISM: Homo sapiens

<400> SEQUENCE: 18

```
Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Leu Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
    370                 375                 380

His Gly Gly Thr Cys Gln Asp Leu Val Asn Gly Phe Lys Cys Val Cys
385                 390                 395                 400
```

-continued

```
Pro Pro Gln Trp Thr Gly Lys Thr Cys Gln Leu Asp Ala Asn Glu Cys
                405                 410                 415
Glu Ala Lys Pro Cys Val Asn Ala Lys Ser Cys Lys Asn Leu Ile Ala
            420                 425                 430
Ser Tyr Tyr Cys Asp Cys Leu Pro Gly Trp Met Gly Gln Asn Cys Asp
        435                 440                 445
Ile Asn Ile Asn Asp Cys Leu Gly Gln Cys Gln Asn Asp Ala Ser Cys
    450                 455                 460
Arg Asp Leu Val Asn Gly Tyr Arg Cys Ile Cys Pro Pro Gly Tyr Ala
465                 470                 475                 480
Gly Asp His Cys Glu Arg Asp Ile Asp Glu Cys Ala Ser Asn Pro Cys
                485                 490                 495
Leu Asn Gly Gly His Cys Gln Asn Glu Ile Asn Arg Phe Gln Cys Leu
            500                 505                 510
Cys Pro Thr Gly Phe Ser Gly Asn Leu Cys Gln Leu Asp Ile Asp Tyr
        515                 520                 525
Cys Glu Pro Asn Pro Cys Gln Asn Gly Ala Gln Cys Tyr Asn Arg Ala
    530                 535                 540
Ser Asp Tyr Phe Cys Lys Cys Pro Glu Asp Tyr Glu Gly Lys Asn Cys
545                 550                 555                 560
Ser His Leu Lys Asp His Cys Arg Thr Thr Pro Cys Glu Val Ile Asp
                565                 570                 575
Ser Cys Thr Val Ala Met Ala Ser Asn Asp Thr Pro Glu Gly Val Arg
            580                 585                 590
Tyr Ile Ser Ser Asn Val Cys Gly Pro His Gly Lys Cys Lys Ser Gln
        595                 600                 605
Ser Gly Gly Lys Phe Thr Cys Asp Cys Asn Lys Gly Phe Thr Gly Thr
    610                 615                 620
Tyr Cys His Glu Asn Ile Asn Asp Cys Glu Ser Asn Pro Cys Arg Asn
625                 630                 635                 640
Gly Gly Thr Cys Ile Asp Gly Val Asn Ser Tyr Lys Cys Ile Cys Ser
                645                 650                 655
Asp Gly Trp Glu Gly Ala Tyr Cys Glu Thr Asn Ile Asn Asp Cys Ser
            660                 665                 670
Gln Asn Pro Cys His Asn Gly Gly Thr Cys Arg Asp Leu Val Asn Asp
        675                 680                 685
Phe Tyr Cys Asp Cys Lys Asn Gly Trp Lys Gly Lys Thr Cys His Ser
    690                 695                 700
Arg Asp Ser Gln Cys Asp Glu Ala Thr Cys Asn Asn Gly Gly Thr Cys
705                 710                 715                 720
Tyr Asp Glu Gly Asp Ala Phe Lys Cys Met Cys Pro Gly Gly Trp Glu
                725                 730                 735
Gly Thr Thr Cys Asn Ile Ala Arg Asn Ser Ser Cys Leu Pro Asn Pro
            740                 745                 750
Cys His Asn Gly Gly Thr Cys Val Val Asn Gly Glu Ser Phe Thr Cys
        755                 760                 765
Val Cys Lys Glu Gly Trp Glu Gly Pro Ile Cys Ala Gln Asn Thr Asn
    770                 775                 780
Asp Cys Ser Pro His Pro Cys Tyr Asn Ser Gly Thr Cys Val Asp Gly
785                 790                 795                 800
Asp Asn Trp Tyr Arg Cys Glu Cys Ala Pro Gly Phe Ala Gly Pro Asp
                805                 810                 815
Cys Arg Ile Asn Ile Asn Glu Cys Gln Ser Ser Pro Cys Ala Phe Gly
```

-continued

```
                   820                 825                 830
Ala Thr Cys Val Asp Glu Ile Asn Gly Tyr Arg Cys Val Cys Pro Pro
            835                 840                 845

Gly His Ser Gly Ala Lys Cys Gln Glu Val Ser Gly Arg Pro Cys Ile
    850                 855                 860

Thr Met Gly Ser Val Ile Pro Asp Gly Ala Lys Trp Asp Asp Cys
865                 870                 875                 880

Asn Thr Cys Gln Cys Leu Asn Gly Arg Ile Ala Cys Ser Lys Val Trp
                885                 890                 895

Cys Gly Pro Arg Pro Cys Leu Leu His Lys Gly His Ser Glu Cys Pro
            900                 905                 910

Ser Gly Gln Ser Cys Ile Pro Ile Leu Asp Asp Gln Cys Phe Val His
        915                 920                 925

Pro Cys Thr Gly Val Gly Glu Cys Arg Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile Ala Cys Glu Pro Ser  Pro Ser Ala
        995                 1000                 1005

Asn Asn  Glu Ile His Val Ala  Ile Ser Ala Glu Asp  Ile Arg Asp
    1010                 1015                 1020

Asp Gly  Asn Pro Ile Lys Glu  Ile Thr Asp Lys Ile  Ile Asp Leu
    1025                 1030                 1035

Val Ser  Lys Arg Asp Gly Asn  Ser Ser Leu Ile Ala  Ala Val Ala
    1040                 1045                 1050

Glu Val  Arg Val Gln Arg Arg  Pro Leu Lys Asn Arg  Thr Asp
    1055                 1060                 1065
```

<210> SEQ ID NO 19
<211> LENGTH: 54
<212> TYPE: DNA
<213> ORGANISM: Artificial Sequence
<220> FEATURE:
<223> OTHER INFORMATION: PCR primer

<400> SEQUENCE: 19
gactatgcga attcggatcc gtcgacgcca ccatgggttc cccacggaca cgcg    54

<210> SEQ ID NO 20
<211> LENGTH: 20
<212> TYPE: DNA
<213> ORGANISM: Artificial Sequence
<220> FEATURE:
<223> OTHER INFORMATION: PCR primer

<400> SEQUENCE: 20
caagttcccc cgttgagaca    20

<210> SEQ ID NO 21
<211> LENGTH: 20
<212> TYPE: DNA
<213> ORGANISM: Artificial Sequence
<220> FEATURE:
<223> OTHER INFORMATION: PCR primer

```
<400> SEQUENCE: 21
atggacaaac accagcagaa                                              20

<210> SEQ ID NO 22
<211> LENGTH: 65
<212> TYPE: DNA
<213> ORGANISM: Artificial Sequence
<220> FEATURE:
<223> OTHER INFORMATION: PCR primer

<400> SEQUENCE: 22
tagtgctcga gctattacaa gtcttcttca gaaataagct tttgttcatc tgttctgttc    60
ttcag                                                              65

<210> SEQ ID NO 23
<211> LENGTH: 44
<212> TYPE: DNA
<213> ORGANISM: Artificial Sequence
<220> FEATURE:
<223> OTHER INFORMATION: PCR primer

<400> SEQUENCE: 23
tttggatttg ctggtgcagt acaactaggc ttaataggga catg                    44

<210> SEQ ID NO 24
<211> LENGTH: 37
<212> TYPE: DNA
<213> ORGANISM: Artificial Sequence
<220> FEATURE:
<223> OTHER INFORMATION: PCR primer

<400> SEQUENCE: 24
tccctattaa gcctagttgt actgcaccag caaatcc                            37

<210> SEQ ID NO 25
<211> LENGTH: 42
<212> TYPE: DNA
<213> ORGANISM: Artificial Sequence
<220> FEATURE:
<223> OTHER INFORMATION: PCR primer

<400> SEQUENCE: 25
tttctgctcg aattcaagct tctaacgatg tacggggaca tg                      42

<210> SEQ ID NO 26
<211> LENGTH: 35
<212> TYPE: DNA
<213> ORGANISM: Artificial Sequence
<220> FEATURE:
<223> OTHER INFORMATION: PCR primer

<400> SEQUENCE: 26
tccccgtaca tcgttagaag cttgaattcg agcag                              35

<210> SEQ ID NO 27
<211> LENGTH: 23
<212> TYPE: DNA
<213> ORGANISM: Artificial Sequence
<220> FEATURE:
<223> OTHER INFORMATION: PCR primer

<400> SEQUENCE: 27
ggatttgctg gtgcagtaca act                                           23
```

```
<210> SEQ ID NO 28
<211> LENGTH: 23
<212> TYPE: DNA
<213> ORGANISM: Artificial Sequence
<220> FEATURE:
<223> OTHER INFORMATION: PCR primer

<400> SEQUENCE: 28
ctgctcgaat tcaagcttct aac                                              23

<210> SEQ ID NO 29
<211> LENGTH: 18
<212> TYPE: DNA
<213> ORGANISM: Artificial Sequence
<220> FEATURE:
<223> OTHER INFORMATION: Jagged antisense oligomer

<400> SEQUENCE: 29
tggggaccgc atcgctgc                                                    18

<210> SEQ ID NO 30
<211> LENGTH: 18
<212> TYPE: DNA
<213> ORGANISM: Artificial Sequence
<220> FEATURE:
<223> OTHER INFORMATION: Jagged sense oligomer

<400> SEQUENCE: 30
gcagcgatgc ggtcccca                                                    18

<210> SEQ ID NO 31
<211> LENGTH: 18
<212> TYPE: DNA
<213> ORGANISM: Artificial Sequence
<220> FEATURE:
<223> OTHER INFORMATION: 3' Jagged antisense oligomer

<400> SEQUENCE: 31
gaatcaaggc tcccctag                                                    18

<210> SEQ ID NO 32
<211> LENGTH: 18
<212> TYPE: DNA
<213> ORGANISM: Artificial Sequence
<220> FEATURE:
<223> OTHER INFORMATION: Mutated 5' Jagged antisense oligomer

<400> SEQUENCE: 32
tgcggtcccc aacggtgg                                                    18

<210> SEQ ID NO 33
<211> LENGTH: 4
<212> TYPE: PRT
<213> ORGANISM: Homo sapiens

<400> SEQUENCE: 33

Pro Glu Ser Thr
1

<210> SEQ ID NO 34
<211> LENGTH: 10
<212> TYPE: DNA
<213> ORGANISM: Mus musculus

<400> SEQUENCE: 34
tggatcagtc                                                             10
```

<210> SEQ ID NO 35
<211> LENGTH: 10
<212> TYPE: DNA
<213> ORGANISM: Mus musculus

<400> SEQUENCE: 35
taaagaggcc                                                              10

<210> SEQ ID NO 36
<211> LENGTH: 10
<212> TYPE: DNA
<213> ORGANISM: Mus musculus

<400> SEQUENCE: 36
cctgatcttt                                                              10

<210> SEQ ID NO 37
<211> LENGTH: 10
<212> TYPE: DNA
<213> ORGANISM: Mus musculus

<400> SEQUENCE: 37
tgtaacagga                                                              10

<210> SEQ ID NO 38
<211> LENGTH: 10
<212> TYPE: DNA
<213> ORGANISM: Mus musculus

<400> SEQUENCE: 38
tctgtgcacc                                                              10

<210> SEQ ID NO 39
<211> LENGTH: 10
<212> TYPE: DNA
<213> ORGANISM: Mus musculus

<400> SEQUENCE: 39
ccaaataaaa                                                              10

<210> SEQ ID NO 40
<211> LENGTH: 10
<212> TYPE: DNA
<213> ORGANISM: Mus musculus

<400> SEQUENCE: 40
ctaataaaag                                                              10

<210> SEQ ID NO 41
<211> LENGTH: 10
<212> TYPE: DNA
<213> ORGANISM: Mus musculus

<400> SEQUENCE: 41
gccaagggtc                                                              10

<210> SEQ ID NO 42
<211> LENGTH: 10
<212> TYPE: DNA
<213> ORGANISM: Mus musculus

<400> SEQUENCE: 42

-continued gtctgctgat 10

<210> SEQ ID NO 43
<211> LENGTH: 10
<212> TYPE: DNA
<213> ORGANISM: Mus musculus

<400> SEQUENCE: 43
aaggaagaga 10

<210> SEQ ID NO 44
<211> LENGTH: 10
<212> TYPE: DNA
<213> ORGANISM: Mus musculus

<400> SEQUENCE: 44
tgaaataaac 10

<210> SEQ ID NO 45
<211> LENGTH: 10
<212> TYPE: DNA
<213> ORGANISM: Mus musculus

<400> SEQUENCE: 45
caccaccaca 10

<210> SEQ ID NO 46
<211> LENGTH: 10
<212> TYPE: DNA
<213> ORGANISM: Mus musculus

<400> SEQUENCE: 46
cctcagcctg 10

<210> SEQ ID NO 47
<211> LENGTH: 10
<212> TYPE: DNA
<213> ORGANISM: Mus musculus

<400> SEQUENCE: 47
ctctgactta 10

<210> SEQ ID NO 48
<211> LENGTH: 10
<212> TYPE: DNA
<213> ORGANISM: Mus musculus

<400> SEQUENCE: 48
gtgggcgtgt 10

<210> SEQ ID NO 49
<211> LENGTH: 10
<212> TYPE: DNA
<213> ORGANISM: Mus musculus

<400> SEQUENCE: 49
tccttggggg 10

<210> SEQ ID NO 50
<211> LENGTH: 10
<212> TYPE: DNA
<213> ORGANISM: Mus musculus

<400> SEQUENCE: 50

-continued

```
cgcctgctag                                                          10

<210> SEQ ID NO 51
<211> LENGTH: 10
<212> TYPE: DNA
<213> ORGANISM: Mus musculus

<400> SEQUENCE: 51
aaaaaaaaaa                                                          10

<210> SEQ ID NO 52
<211> LENGTH: 10
<212> TYPE: DNA
<213> ORGANISM: Mus musculus

<400> SEQUENCE: 52
aagcagaagg                                                          10

<210> SEQ ID NO 53
<211> LENGTH: 10
<212> TYPE: DNA
<213> ORGANISM: Mus musculus

<400> SEQUENCE: 53
caggactccg                                                          10

<210> SEQ ID NO 54
<211> LENGTH: 10
<212> TYPE: DNA
<213> ORGANISM: Mus musculus

<400> SEQUENCE: 54
gaagcaggac                                                          10

<210> SEQ ID NO 55
<211> LENGTH: 10
<212> TYPE: DNA
<213> ORGANISM: Mus musculus

<400> SEQUENCE: 55
ggatatgtgg                                                          10

<210> SEQ ID NO 56
<211> LENGTH: 10
<212> TYPE: DNA
<213> ORGANISM: Mus musculus

<400> SEQUENCE: 56
gttctgattg                                                          10
```

THERAPEUTIC AND DIAGNOSTIC METHODS AND COMPOSITIONS BASED ON JAGGED/NOTCH PROTEINS AND NUCLEIC ACIDS

CROSS-REFERENCE TO RELATED APPLICATIONS

The present application is a continuation-in-part of U.S. application Ser. No. 09/199,865, now U.S. Pat. No. 6,433,138 filed on Nov. 25, 1998, which is a continuation of PCT Application No. US/PCT97/09407, filed on May 30, 1997, all of which are entitled to priority under 35 U.S.C. §119(e), to U.S. Provisional Application No. 60/018,841, filed on May 31, 1996, and all of which are hereby incorporated herein by reference in their entirety.

STATEMENT REGARDING FEDERALLY SPONSORED RESEARCH OR DEVELOPMENT

This invention was supported in part by funds from the U.S. Government (National Institutes of Health Grant Nos. AG07450-12, HL32348-18, HL54710-04, and HL35627-16) and the U.S. Government may therefore have certain rights in the invention.

BACKGROUND OF THE INVENTION

The present invention relates to therapeutic and diagnostic methods and compositions based on Jagged/Notch proteins and nucleic acids, and on the role of their signaling pathway in endothelial cell migration, angiogenesis, and/or differentiation.

The functional integrity of the human vascular system is maintained by the endothelial cell which monitors the non-thrombogenic interface between blood and tissue in vivo. Thus, factors that influence human endothelial cell function may contribute significantly to the regulation and maintenance of homeostasis (see Maciag, 1984, In: Progress in Hemostasis and Thrombosis, pp. 167–182, Spaet, ed., A. R. Liss, New York; Folkman and Klagsbum, 1987, Science 235:442–447; Burgess and Maciag, 1989, Annu. Rev. Biochem. 58:575–606). Likewise, events that perturb this complex equilibrium are relevant to the pathophysiology of human disease states in which cellular components of the vascular tree are active participants including, e.g., atherogenesis, coronary insufficiency, hypertension, rheumatoid arthritis, solid tumor growth and metastasis, and wound repair.

Since the endothelium is present in all organs and tissues, endothelial cell function is also fundamental to the physiology and integration of these multicellular systems. This includes the ability to monitor and interface with repair systems that employ the tightly regulated inflammatory, angiogenic and neurotropic responses. Indeed, biochemical signals that are responsible for the modification of these responses have been well characterized as polypeptide growth factors and cytokines; however, their mechanisms of operation have, prior to the present invention, been poorly understood, impeding their acceptance as valuable tools in clinical management.

A major accomplishment of modern biology has been the recognition that structural elements responsible for physiologic functions are conserved throughout the animal kingdom. Genetic analysis of yeast, C. elegans, Xenopus, Zebra fish, and Drosophila, among others, has provided new insight into the regulation of the cell cycle, organelle biosynthesis and trafficking, cell fate and lineage decisions during development, as well as providing the fundamental principles for transcriptional/translational/post-translational regulation. Indeed, the conservation of structure-function principles exhibited by such systems has generated new insight into these and other regulatory systems utilized by mammalian cells. Moreover, a resolution of the genetic structure of the mammalian homologs for such genes in non-mammalian species has often led to a discernment of their function in mammals, even though the delineation of the function of a particular homologous mammalian gene or gene fragment may well be serendipitous. In many cases, it is the result produced by expression and differential cDNA cloning strategies that manifest mammalian DNA sequences with homology to genes previously identified in more primitive species.

During the past decade, differential cDNA cloning methods, including e.g., conventional subtractive hybridization (Hla and Maciag, 1990, Biochem. Biophys. Res. Commun. 167:637–643), differential polymerase chain reaction (PCR)-oriented hybridization (Hla and Maciag, 1990, J. Biol. Chem. 265:9308–9313), and more recently, a modification of the differential display (Zimrin et al., 1995, Biochem. Biophys. Res. Commun. 213:630–638) were used to identify genes induced during the process of human umbilical vein endothelial cell (HUVEC) differentiation in vitro. Very early studies disclosed that HUVEC populations are able to generate capillary-like, lumen-containing structures when introduced into a growth-limited environment in vitro (Maciag et al., 1982, J. Cell Biol. 94:511–520). These studies permitted the identification and characterization of protein components of the extracellular matrix as inducers of this differentiation process, while at the same time defining the capillary-like structures as non-terminally differentiated (Maciag, 1984, In: Progress in Hemostasis and Thrombosis, pp. 167–182, Spaet, ed., A. R. Liss, New York). Additional experiments have elucidated the importance of polypeptide cytokines, such as IL-1 (Maier et al., 1990, J. Biol. Chem. 265:10805–10808) and IFNγ (Friesel et al., 1987, J. Cell Biol. 104:689–696), as inducers of HUVEC differentiation in vitro, and ultimately lead to an understanding that the precursor form of IL-1α was responsible for the induction of HUVEC senescence in vitro (Maciag et al., 1981, J. Cell Biol. 91:420–426; Maier et al., 1990, Science 249:1570–1574)—the only truly terminal HUVEC phenotype identified to date as summarized in FIG. 1.

Recent research has employed differential cDNA cloning methods, which permits the identification of new and very interesting genes. However, until very recently, establishing their identity did not provide insight into the mechanism of HUVEC differentiation. Current research has focused upon the fibroblast growth factor (FGF) and interleukin (IL)-1 gene families as regulators of the angiogenesis process, both in vitro and in vivo (Friesel et al., 1995, FASEB J. 9:919–925; Zimrin et al., 1996, J. Clin. Invest. 97:1359). The human umbilical vein endothelial cell (HUVEC) has proven to be an effective model for studying the signal pathways utilized by FGF-1 to initiate HUVEC migration and growth, the role of IL-1α as an intracellular inhibitor of FGF-1 function and modifier of HUVEC senescence, and the interplay between the FGF and the IL-1 gene families as key effectors of HUVEC differentiation in vitro. Such insight has enabled the present inventors to use modem molecular methods to identify a key regulatory ligand-receptor signaling system, which is able to both induce capillary endothelial cell migration and repress large vessel endothelial cell migration.

The Jagged/Serrate/Delta-Notch/Lin/Glp signaling system, originally described during the development of C.

*elegans* and Drosophila as an essential system instrumental in cell fate decisions, has been found to be highly conserved in mammalian cells (Nye and Kopan, 1995, Curr. Biol. 5:966–969). Notch proteins comprise a family of closely-related transmembrane receptors initially identified in embryologic studies in Drosophila (Fortini and Artavanis-Tsakonas, 1993, Cell 75:1245–1247). The genes encoding the Notch receptor show a high degree of structural conservation, and contain multiple EGF repeats in their extracellular domains (Coffman et al., 1990, Science 249:1438–1441; Ellisen et al., 1991, Cell 66:649–661; Weinmaster et al., 1991, Development 113:199–205; Weinmaster et al., 1992, Development 116:931–941; Franco del Amo et al., 1992, Development 115:737–744; Reaume et al., 1992, Dev. Biol. 154:377–387; Lardelli and Lendahi, 1993, Mech. Dev. 46:123–136; Bierkamp and Campos-Ortega, 1993, Mech. Dev. 43:87–100; Lardelli et al., 1994, Exp. Cell Res. 204:364–372). In addition to the thirty-six EGF repeats within the extracellular domain of Notch 1, there is a cys-rich domain composed of three Notch Lin Glp (NLG) repeats, which is important for ligand function, followed by a cys-poor region between the transmembrane and NLG domain.

The intracellular domain of Notch 1 contains six ankyrin/Cdc 10 repeats positioned between two nuclear localization sequences (NLS) (Artavanis-Tsakonas et al., 1995, Science 268:225–232). This motif is found in many functionally diverse proteins (see, e.g., Bork, 1993, Proteins 17:363–374), including members of the Rel/NF-κB family (Blank et al., 1992, TIBS 17:135–140), and is thought to be responsible for protein-protein interactions. Notch has been shown to interact with a novel ubiquitously distributed cytoplasmic protein deltex through its ankyrin repeats, a domain shown by deletion analysis to be necessary for activity (Matsuno et al., 1995, Development 121:2633–2644).

Carboxy terminal to this region is a polyglutamine-rich domain (OPA) and a pro-glu-ser-thr (PEST) domain (SEQ ID NO:33) which may be involved in signaling protein degradation. There are numerous Notch homologs, including three Notch genes. (The corresponding structures for Lin-12 and Glp-1 are shown in FIG. 4.)

Several Notch ligands have been identified in vertebrates, including Delta, Serrate and Jagged. The Notch ligands are also transmembrane proteins, having highly conserved structures. These ligands are known to signal cell fate and pattern formation decisions through the binding to the Lin-12/Notch family of transmembrane receptors (Muskavitch and Hoffmann, 1990, Curr. Top. Dev. Biol. 24:289–328; Artavanis-Tsakonas and Simpson, 1991, Trends Genet. 7:403–408; Greenwald and Rubin, 1992, Cell 68:271–281; Gurdon, 1992, Cell 68:185–199; Fortini and Artavanis-Tsakonas, 1993, Cell 75:1245–1247; and Weintraub, 1993, Cell 75:1241–1244). A related protein, the Suppressor of hairless (Su(H)), when co-expressed with Notch in Drosophila cells, is sequestered in the cytosol, but is translocated to the nucleus when Notch binds to its ligand Delta (Fortini and Artavanis-Tsakonas, 1993, Cell 75:1245 –1247). Studies with constitutively activated Notch proteins missing their extracellular domains have shown that activated Notch suppresses neurogenic and mesodermal differentiation (Coffinan et al., 1993, Cell 73:659–671; Nye et al., 1994, Development 120:2421–2430).

The Notch signaling pathway (FIG. 3), which is apparently activated by Jagged in the endothelial cell, involves cleavage of the intracellular domain by a protease, followed by nuclear trafficking of the Notch fragment and the interaction of this fragment with the $KBF_2/RBP-J_k$ transcription factor (Jarriault et al., 1995, Nature 377:355–358; Kopan et al., 1996, Proc. Natl. Acad. Sci. USA 93:1683–1688), a homolog of the Drosophila Suppressor of hairless gene (Schweisguth et al., 1992, Cell 69:1199–1212), a basic helix-loop-helix transcription factor involved in Notch signaling in insects (Jennings et al., 1994, Development 120:3537–3548) and in the mouse (Sasai et al., 1992, Genes Dev. 6:2620–2634). This effector is able to repress the transcriptional activity of other genes encoding transcription factors responsible for entry into the terminal differentiation program (Nye et al., 1994; Kopan et al., 1994, J. Cell. Physiol. 125:1–9).

The Jagged gene encodes a transmembrane protein which is directed to the cell surface by the presence of a signal peptide sequence (Lindsell et al., 1995, Cell 80:909–917). While the intracellular domain contains a sequence with no known homology to intracellular regions of other transmembrane structures, the extracellular region of the ligand contains a cys-rich region, 16 epidermal growth factor (EGF) repeats, and a DSL (Delta Serrate Lag) domain. As shown in FIG. 2, the DSL domain as well as the EGF repeats, are found in other genes including the Drosophila ligands, Serrate (Baker et al., 1990, Science 250:1370–1377; Thomas et al., 1991, Development 111:749–761) and Delta (Kopczynski et al., 1988, Genes Dev. 2:1723 –1735), and *C. elegans* genes Apx-1 (Henderson et al., 1994, Development 120:2913–2924; Mello et al., 1994, Cell 77:95–106) and Lag-2 (Tax et al., 1994, Nature 368:150–154).

Nevertheless, until the discovery of the presently disclosed invention, human Jagged remained undefined and the function and relationship, if any, of the human ligand to Notch remained unknown in the art. However, there was a recognized need in the art for a complete understanding of the protein's role in the regulation of cell differentiation and regulation. The present invention provides this understanding and in addition, provides compositions and methods useful for treatment of Jagged-related diseases in mammals.

BRIEF SUMMARY OF THE INVENTION

The invention includes an isolated nucleic acid encoding a soluble Jagged protein. The invention also includes a vector and a recombinant cell comprising the isolated nucleic acid. Further, the invention includes an isolated polypeptide encoded by isolated nucleic acid.

In one aspect, the nucleic acid comprises a portion of sequence of SEQ ID NO:2, where the portion comprises the soluble Jagged.

The invention also includes an isolated nucleic acid having at least 30% identity with from about nucleotide number I to about nucleotide 3201 of SEQ ID NO:2.

The invention includes an isolated nucleic acid encoding a soluble Jagged protein, the nucleic acid having at least about 20% identity with SEQ ID NO:17. In one aspect, the nucleic acid has the sequence of SEQ ID NO:17.

The invention includes an isolated nucleic acid encoding a soluble Jagged protein, the soluble Jagged protein having at least about 40% identity with SEQ ID NO:18. The invention further includes a vector and a recombinant cell comprising this isolated nucleic acid. The invention also includes an isolated polypeptide encoded by the nucleic acid.

In one aspect, the nucleic acid encoding a soluble Jagged protein has the sequence of SEQ ID NO:18.

The invention includes an isolated nucleic acid encoding a soluble Jagged protein, where the nucleic acid further comprises a nucleic acid encoding a tag polypeptide covalently linked thereto.

In one aspect, the tag polypeptide is selected from the group consisting of a myc tag polypeptide, a myc-pyruvate kinase tag polypeptide, a glutathione-S-transferase tag polypeptide, a maltose binding tag polypeptide, green fluorescence protein tag polypeptide, an alkaline phosphatase tag polypeptide, a His6 tag polypeptide, an influenza virus hemagglutinin tag polypeptide, and a maltose binding protein tag polypeptide.

In another aspect, the tag polypeptide is a myc tag polypeptide.

The invention includes an isolated nucleic acid encoding a soluble Jagged protein, where the nucleic acid further comprises a promoter/regulatory sequence operably linked thereto.

The invention includes an isolated soluble Jagged polypeptide. In one aspect, the isolated polypeptide shares at least about 20% identity with a polypeptide having the amino acid sequence of SEQ ID NO:18. In a further aspect, the polypeptide is SEQ ID NO:18.

The invention includes an isolated polypeptide encoded by an isolated nucleic acid encoding a soluble Jagged, where the polypeptide has at least about 20% identity with from about amino acid residue 1 to about amino acid residue 1067 of the sequence of SEQ ID NO:1.

In one aspect, the polypeptide further comprises a tag polypeptide. In a further aspect, the tag polypeptide is selected from the group consisting of a myc tag polypeptide, a myc-pyruvate kinase tag polypeptide, a glutathione-S-transferase tag polypeptide, a maltose binding tag polypeptide, green fluorescence protein tag polypeptide, an alkaline phosphatase tag polypeptide, a His6 tag polypeptide, an influenza virus hemagglutinin tag polypeptide, and a maltose binding protein tag polypeptide. In yet a further aspect, the tag epitope is a myc tag epitope.

The invention includes a recombinant cell comprising an isolated polypeptide encoded by an isolated nucleic acid encoding a soluble Jagged protein.

The invention includes a composition comprising an isolated soluble Jagged polypeptide in a pharmaceutically acceptable carrier.

The invention also includes a composition comprising a nucleic acid encoding a soluble Jagged protein in a pharmaceutically acceptable carrier.

The invention includes a pharmaceutical composition comprising a therapeutically effective amount of an isolated nucleic acid encoding a soluble Jagged polypeptide, or a functionally equivalent derivative, or an allelic or species variant thereof, in a pharmaceutically acceptable carrier.

The invention further includes a pharmaceutical composition comprising a therapeutically effective amount of an isolated soluble Jagged polypeptide, or a functionally equivalent derivative, or an allelic or species variant thereof, in a pharmaceutically acceptable carrier.

The invention includes a pharmaceutical composition comprising a recombinant cell comprising an isolated nucleic acid encoding a soluble Jagged polypeptide in a pharmaceutically acceptable carrier.

The invention also includes a pharmaceutical composition comprising a recombinant cell comprising an isolated soluble Jagged polypeptide.

The invention includes a method of affecting angiogenesis in a system capable of angiogenesis. The method comprises contacting a cell with an angiogenic effective amount of an isolated soluble Jagged polypeptide, thereby affecting angiogenesis in a system capable of angiogenesis.

The invention includes a method of affecting angiogenesis in a mammal. The method comprises administering to a mammal an angiogenic effective amount of an isolated soluble Jagged polypeptide, thereby affecting angiogenesis in a mammal. In one aspect, the isolated soluble Jagged polypeptide is administered by administering to the mammal at least one molecule selected from the group consisting of an isolated soluble Jagged polypeptide, an isolated nucleic acid encoding a soluble Jagged polypeptide, and a recombinant cell comprising an isolated nucleic acid encoding a soluble Jagged polypeptide.

The invention also includes a method of affecting differentiation of a cell. The method comprises contacting a cell with a differentiation effective amount of an isolated soluble Jagged polypeptide, thereby affecting differentiation of said cell. In one aspect, the cell is selected from the group consisting of a mesodermal-derived cell, an endodermal-derived cell, an ectodermal-derived cell, and a neurodermal-derived cell.

The invention includes a method of identifying a compound capable of affecting differentiation of a cell. The method comprises contacting a recombinant cell comprising an isolated nucleic acid encoding a soluble Jagged protein expressed therefrom with a test compound and comparing the growth characteristics of the cell contacted with the compound with the growth characteristics of an otherwise identical cell not contacted with the compound, wherein a difference in the growth characteristics of the cell contacted with the compound compared with the growth characteristics of the otherwise identical cell not contacted with the compound is an indication that the compound is capable of affecting differentiation of the cell.

The invention includes a method of identifying a compound capable of affecting the binding of Jagged ligand to a Notch receptor. The method comprises contacting a recombinant cell comprising a nucleic acid encoding a soluble Jagged protein with a test compound and comparing the growth characteristics of the cell contacted with the compound with the growth characteristics of an otherwise identical cell not contacted with the compound, wherein a difference in the growth characteristics of the cell contacted with the compound compared with the growth characteristics of the otherwise identical cell not contacted with the compound is an indication that the compound is capable of affecting the binding of Jagged ligand to a Notch receptor.

The invention includes a method of identifying a compound capable of affecting angiogenesis. The method comprises contacting a recombinant cell comprising a nucleic acid encoding a soluble Jagged protein expressed therefrom with a test compound and comparing the growth characteristics of the cell contacted with the compound with the growth characteristics of an otherwise identical cell not contacted with the compound, wherein a difference in the growth characteristics of the cell contacted with the compound compared with the growth characteristics of the otherwise identical cell not contacted with the compound is an indication that the compound is capable of affecting angiogenesis.

The invention further includes a method of inhibiting expression of type I collagen in a cell. The method comprises administering an expression inhibiting amount of soluble Jagged to a cell, thereby inhibiting expression of type I collagen.

In one aspect, the soluble Jagged is administered as a substance selected from the group consisting of an isolated nucleic acid encoding soluble Jagged, a vector expressing soluble Jagged, and an isolated soluble Jagged polypeptide.

The invention includes a kit for affecting angiogenesis in a mammal. The kit comprises an angiogenic effective amount of an isolated soluble Jagged polypeptide, an applicator, and an instructional material for the use of the kit.

The invention includes a kit for affecting differentiation of a cell. The kit comprises a differentiation effective amount of an isolated soluble Jagged polypeptide, an applicator, and an instructional material for the use of the kit.

The invention includes a kit for inhibiting expression of type I collagen in a cell. The kit comprises an expression inhibiting amount of soluble Jagged, an applicator, and an instructional material for the use of the kit.

Additional objects, advantages and novel features of the invention will be set forth in part in the description which follows, and in part will become apparent to those skilled in the art on examination of the following, or may be learned by practice of the invention.

BRIEF DESCRIPTION OF THE SEVERAL VIEWS OF THE DRAWINGS

FIG. 8A is a diagram depicting the amino acid sequence of human Jagged (GenBank Accession No. U77720 [SEQ ID NO:1]). The amino acid sequence, which is depicted using the standard one-letter amino acid residue code, is provided. The amino acid sequence comprises various domains including, but not limited to, a signal peptide (from about amino acid residue 1 to about amino acid residue 21); a DSL domain (from about amino acid residue 185 to about amino acid residue 229); EGF repeats (from about amino acid residue 234 to about amino acid residue 862); a cysteine-rich region (from about amino acid residue 863 to about amino acid residue 1002); a transmembrane domain (from about amino acid residue 1068 to about amino acid residue 1093); and a cytoplasmic region (from about amino acid residue 1094 to about amino acid residue 1218).

FIGS. 8B–C is a diagram depicting the nucleic acid sequence of human Jagged (GenBank Acc. No. U77720 [SEQ ID NO:2]). Nucleotides designated by "Y" indicates C or T at that position, and nucleotides designated by "R" indicates G or A.

FIG. 13A is an image depicting the amino acid sequence of soluble-Jagged (SEQ ID NO:18).

FIGS. 13B–C is an image depicting the nucleic acid sequence of soluble-Jagged (SEQ ID NO:17). Nucleotides designated by "Y" indicates C or T at that position, and nucleotides designated by "R" indicates G or A.

DETAILED DESCRIPTION OF THE INVENTION

Figure 1:
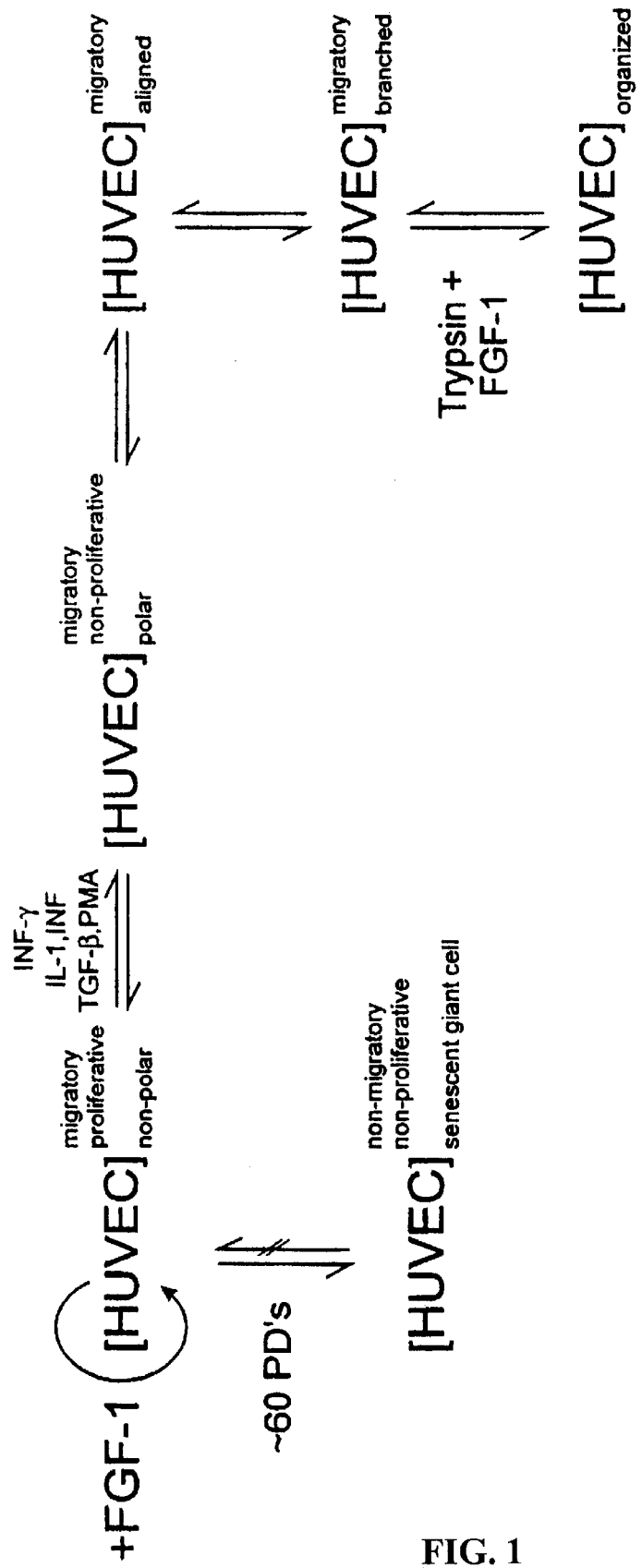
FIG. 1 is a diagram illustrating the phenotypic alterations of HUVEC by cytokines. Early studies demonstrated that HUVEC populations are able to generate capillary-like, lumen-containing structures when introduced into a growth-limited environment in vitro. However, exposure of an HUVEC population to polypeptide cytokines, such as IL-1 and IFNγ, as inducers of HUVEC differentiation in vitro, led to an understanding that the precursor form of IL-1α was responsible for the induction of HUVEC senescence in vitro, the only truly terminal HUVEC phenotype identified to date. (PD=population doubling).

As disclosed in the present invention, the human Jagged gene (and soluble forms thereof) has now been cloned, isolated and defined, and the Jagged-Notch role in endothelial cell differentiation and/or migration has been elucidated. In addition, it is presently disclosed that the novel signaling pathway produces disparate effects on the migration of large and small vessel endothelial cells, providing what appears to be the first demonstration of a signaling difference between large and small vessel endothelial cells both in degree and direction. This highlights the potential function of a previously unknown ligand-receptor signaling pathway in the endothelial cell which is modulated during the migratory phase of angiogenesis. Moreover, the present invention provides an explanation of the previously unresolved phenomenon in which endothelial cells have been shown to reproducibly differentiate into a non-terminal and completely reversible tubular-like cell phenotype in vitro (Maciag et al., 1982, J. Cell Biol. 94:511–520). Thus, the present invention significantly advances the art, providing not only methods of regulating cell differentiation and angiogenesis, but also teaching a method for preventing the undesirable migration of specific cell types into large blood vessels following angioplastic surgery to control restenosis.

Definitions

As used herein, each of the following terms has following meaning.

The articles "a" and "an" are used herein to refer to one or to more than one (i.e., to at least one) of the grammatical object of the article. By way of example, "an element" means one element or more than one element.

As used herein, the term "adjacent" is used to refer to nucleotide sequences which are directly attached to one another, having no intervening nucleotides. By way of example, the pentanucleotide 5'-AAAAA-3' is adjacent the trinucleotide 5'-TTT-3' when the two are connected thus: 5'-AAAAATTT-3' or 5'-TTTAAAAA-3', but not when the two are connected thus: 5'-AAAAACTTT-3'.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

By the term "angiogenic effective amount," as the term is used herein, is meant an amount of soluble Jagged, or a mutant, derivative, variant, or fragment thereof, which when administered to a cell, tissue, or organism, induces a detectable increase in the level of angiogenesis in the cell, tissue, or organism, compared with the level of angiogenesis prior to or on the absence of the administration of the soluble Jagged.

"Angiogenesis," as used herein, means the formation of new blood vessels and encompasses the development of angiogenic tissue and/or altered cell or tissue morphology typical of angiogenic tissue development. One skilled in the art would appreciate, based upon the disclosure provided herein, that the level of angiogenesis can be assessed using, for example but not limited to, a CAM assay, a nude mouse in vivo assay, an endothelial cell migration assay to assess sprout formation, the development of chord-like structures, and the like.

By the term "angiogenesis effective amount," as used herein, is meant an amount of soluble Jagged that mediates a detectable increase or decrease in the level of angiogenesis in a cell, tissue, or organism. One skilled in the art would appreciate, based upon the disclosure provided herein, that such amount depends on the nature of the cell, tissue or organism to which the soluble Jagged is administered. The skilled artisan would further appreciate, based upon the disclosure provided herein, that there are a number of assays, several of which are disclosed elsewhere herein, useful for assessing the level of angiogenesis in a cell, a tissue, and/or an organism, and such assays, as well as those developed in the future, are contemplated in the present invention.

By the term "applicator" as the term is used herein, is meant any device including, but not limited to, a hypodermic syringe, a pipette, and the like, for administering the soluble Jagged nucleic acid, protein, and/or composition of the invention to a mammal.

"Antisense nucleic acid sequence," "antisense sequence," "antisense DNA molecule" or "antisense gene" refer to pseudogenes which are constructed by reversing the orientation of the gene with regard to its promoter, so that the antisense strand is transcribed. The term also refers to the antisense strand of RNA or of cDNA which compliments the strand of DNA encoding the protein or peptide of interest. In either case, when introduced into a cell under the control of a promoter, the anti-sense nucleic acid sequence inhibits the synthesis of the protein of interest from the endogenous gene. The inhibition appears to depend on the formation of an RNA-RNA or cDNA-RNA duplex in the nucleus or in the cytoplasm. Thus, if the antisense gene is stably introduced into a cultured cell, the normal processing and/or transport is affected if a sense-antisense duplex forms in the nucleus; or if antisense RNA is introduced into the cytoplasm of the cell, the expression or translation of the endogenous product is inhibited.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

Antisense nucleic acid sequences can further include modifications which can affect the biological activity of the antisense molecule, or its manner or rate of expression. Such modifications can also include, e.g., mutations, insertions, deletions, or substitutions of one or more nucleotides that do not affect the function of the antisense molecule, but which may affect intracellular localization. Modifications include, but are not limited to, 5-fluorouracil, 5-bromouracil, 5-chlorouracil, 5-iodouracil, hypoxanthine, xanthine, 4-acetylcytosine, 5-(carboxyhydroxymethyl uracil, 5-carboxyhydroxymethyl-2-thiouridine, 5-carboxymethylaminomethyl uracil, dihydrouracil, beta-D-galactosylqueosine, inosine, N6-isopentyladenine, 1-methylguanine, 1-methylinosine, 2,2 dimethylguanine, 2-methyladenine, 2-methylguanine, 3-methylcytosine, 5-methylcytosine, N6-adenine, 7-methylguanine, 5-methylaminomethyluracil, 5-methylaminomethyl-2-thioracil, beta-D-mannosylqueosine, 5'-methoxycarboxymethyluracil, 5-methyluracil, 2-methylthio-N6-isopentenyladenine, uracil-5 oxyacetic acid, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methy-2-thiouracil, 3-(3-amino-3-N-2-carboxypropyl) uracil, and 2,6-diaminopurine.

The antisense nucleic acid sequence can determine an uninterrupted antisense RNA sequence or it can include one or more introns. The antisense Jagged molecule(s) of the present invention are referred to as "γ-Jagged."

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand. "Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (ie., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The use of the term "DNA encoding" should be construed to include the DNA sequence which encodes the desired protein and any necessary 5' or 3' untranslated regions accompanying the actual coding sequence.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A "differentiation effective amount," as the term is used herein, means an amount of soluble Jagged that mediates a detectable increase or decrease in the level of behavior associated with endothelial cell differentiation. One skilled in the art would appreciate, based upon the disclosure provided herein, that such amount depends on the nature of the cell, tissue, or organism to which the soluble Jagged is administered. The skilled artisan would further appreciate, based upon the disclosure provided herein, that there are a number of assays, several of which are disclosed elsewhere herein, useful for assessing the level of differentiation, such as a modified differential display method, endothelial cell (e.g., HUVEC) organization, endothelial cell migration, sprout formation, as well as assays to be developed in the future, contemplated in the present invention.

By the term "expression inhibiting amount", as the term is used herein, is meant an amount of soluble Jagged that mediates a detectable decrease in the level of type I collagen expression in a cell when the level of type I collagen expression in the cell is compared to the level of type I collagen expression in the same cell prior to administration of soluble Jagged or to the level of type I collagen in an otherwise identical cell to which soluble Jagged is not administered.

One skilled in the art would appreciate, based upon the disclosure provided herein, that such amount depends on the nature of the cell or tissue from which the cell is obtained, and the amount of endogenous type I collagen expression in the cell prior to or in the absence of administration of soluble Jagged.

The skilled artisan would further appreciate, based upon the disclosure provided herein, that there are a number of assays, several of which are disclosed elsewhere herein, useful for assessing the level of type I collagen expression in a cell such as a differential display method (e.g., SAGE analysis), antibody-based detection of type I collagen gene translation product in a cell (e.g., immunoblotting, ELISA, immunoprecipitation, and the like), and detection of nucleic acid encoding type I collagen (e.g., Southern blotting, Northern blotting, PCR-based assays, and the like), as well as assays to be developed in the future.

A first region of an oligonucleotide "flanks" a second region of the oligonucleotide if the two regions are adjacent to one another or if the two regions are separated by no more than about 1000 nucleotide residues, and preferably no more than about 100 nucleotide residues.

By the term "DNA segment" is meant a molecule comprising a linear stretch of nucleotides wherein the nucleotides are present in a sequence that encodes, through the genetic code, a molecule comprising a linear sequence of amino acid residues that is referred to as a protein, a protein fragment, or a polypeptide.

"Gene," as used herein, refers to a single polypeptide chain or protein, and as used herein includes the 5' and 3' ends. The polypeptide can be encoded by a full-length sequence or any portion of the coding sequence, so long as the functional activity of the protein is retained.

A "complementary DNA" or "cDNA" gene includes recombinant genes synthesized by reverse transcription of messenger RNA ("mRNA") lacking intervening sequences (introns).

"Structural gene" means a DNA sequence that is transcribed into mRNA that is then translated into a sequence of amino acids characteristic of a specific polypeptide. According to art-recognized convention, the first nucleotide of the first translated codon is numbered +1, and the nucleotides are numbered consecutively with positive integers through the translated region of the structural gene and into the 3' untranslated region. The numbering of the nucleotides in the promoter and/or regulatory region 5' to the translated region proceeds consecutively with negative integers with the 5' nucleotide next to the first translated nucleotide being numbered −1.

By the term "gel electrophoresis," is meant assay to assess the size of particular DNA fragments. More specifically, the most common technique (although not the only one) to determine the size of a nucleic acid fragment, is agarose gel electrophoresis, which is based on the principle that DNA molecules migrate through the gel as though it were a sieve that retards the movement of the largest molecules to the greatest extent, and the movement of the smallest molecules to the least extent. The fractionated molecules can be visualized by staining, permitting the DNA fragments of a genome to be visualized. Such techniques are well-known in the art and the gel matrix can be comprised of a variety of substances including, but not limited to, agarose, acrylamide, and the like, as described in, e.g., Sambrook et al. (1989, Molecular Cloning: A Laboratory Manual, Cold Spring Harbor Laboratory Press, New York), Ausubel et al. (1997, Current Protocols in Molecular Biology, Green & Wiley, New York), and other standard treatises.

Most genomes, including the human genome, contain too many DNA sequences to produce an easily visualized pattern. Thus, a methodology referred as "Southern hybridization" (or "blotting") is used to visualize small subsets of fragments. By this procedure the fractionated DNA is physically transferred onto nitrocellulose filter paper or another appropriate surface using recognized methods. Note that RNA fragments can be similarly visualized by the "northern blot" process.

By the term "nucleic acid hybridization," is meant a process by which two single-stranded nucleic acid molecules will bind with each other. The process depends on the principle that two single-stranded molecules that have complementary base sequences will reform into the thermodynamically favored double-stranded configuration ("reanneal") if they are mixed in solution under the proper conditions. The reannealling process can occur even if one of the single strands is immobilized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3' TATGGC share 50% homology.

As used herein, "homology" is used synonymously with "identity."

In addition, when the term "homology" is used herein to refer to the nucleic acids and proteins, it should be construed to be applied to homology at both the nucleic acid and the amino acid levels.

A first oligonucleotide anneals with a second oligonucleotide with "high stringency" if the two oligonucleotides anneal under conditions whereby only oligonucleotides which are at least about 60%, more preferably at least about 65%, even more preferably at least about 70%, yet more preferably at least about 80%, and preferably at least about 90% or, more preferably, at least about 95% complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, *Molecular Cloning: A Laboratory Manual*, Cold Spring Harbor Laboratory, New York).

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264–2268), modified as in Karlin and Altschul (1993, Proc. Natl. Acad. Sci. USA 90:5873–5877). This algorithm is incorporated into the NBLAST and XBLAST programs of Altschul, et al. (1990, J. Mol. Biol. 215:403–410), and can be accessed, for example, at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein.

To obtain gapped alignments for comparison purposes, Gapped BLAST can be utilized as described in Altschul et al. (1997, Nucleic Acids Res. 25:3389–3402). Alternatively, PSI-Blast or PHI-Blast can be used to perform an iterated search which detects distant relationships between molecules (id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See National Center for Biotechnology Information world wide web site.

The percent identity between two sequences can be determined using techniques similar to those described above, with or without allowing gaps. In calculating percent identity, typically exact matches are counted.

As used herein, the terms "gene" and "recombinant gene" refer to nucleic acid molecules comprising an open reading frame encoding a polypeptide of the invention. Such natural allelic variations can typically result in 1–5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

Moreover, nucleic acid molecules encoding proteins of the invention from other species (homologs), which have a nucleotide sequence which differs from that of the human proteins described herein are within the scope of the invention. Nucleic acid molecules corresponding to natural allelic variants and homologs of a cDNA of the invention can be isolated based on their identity to human nucleic acid molecules using the human cDNAs, or a portion thereof, as a hybridization probe according to standard hybridization techniques under stringent hybridization conditions. For example, a cDNA encoding a soluble form of a membrane-bound protein of the invention, Jagged-1, can be isolated based on its hybridization with a nucleic acid molecule encoding all or part of the membrane-bound form. Likewise, a cDNA encoding a membrane-bound form can be isolated based on its hybridization with a nucleic acid molecule encoding all or part of the soluble form.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

The term "ligand," as used herein, refers to any protein or proteins that can interact with a receptor binding domain, thus having a "binding affinity" for such domain. Ligands can be soluble or membrane bound, and they can be a naturally occurring protein, or synthetically or recombinantly produced. The ligand can also be a nonprotein molecule that acts as ligand when it interacts with the receptor binding domain. Interactions between the ligand and receptor binding domain include, but are not limited to, any covalent or non-covalent interactions. The receptor binding domain is any region of the receptor molecule, e.g., Notch, that interacts directly or indirectly with the ligand, e.g., Jagged. If the Notch-Jagged interaction acts as an on-off switch, Jagged can provide the receptor binding domain, and Notch or a component produced as a result of the Notch-Jagged interaction can act as the ligand.

"Mutants," "derivatives," and "variants" of the peptides of the invention (or of the DNA encoding the same) are peptides which may be altered in one or more amino acids (or in one or more base pairs) such that the peptide (or nucleic acid) is not identical to the sequences recited herein, but has the same property as the soluble Jagged peptides disclosed herein, in that the peptide has the property of inducing expression of certain genes as assessed using SAGE analysis (e.g., enhancer of split groucho, type IV collagenase, connexin 32, cathepsin D, and vimentin; mediating reduced level of expression of certain genes (e.g., pro-α-2(I) collagen, FGFR-1, and IkB-β), affecting endothelial sprout formation, affecting angiogenesis, the ability to develop angiogenic tissue masses in nude mice, the ability to induce angiogenesis in a CAM angiogenesis model, and the like.

A "functional derivative" of a sequence, either protein or nucleic acid, is a molecule that possesses a biological activity (either functional or structural) that is substantially similar to a biological activity of Jagged protein or a nucleic acid sequence encoding Jagged, or a portion thereof. A functional derivative of a protein may or may not contain post-translational modifications such as covalently linked carbohydrate, depending on the necessity of such modifications for the performance of a specific function. The term "functional derivative" is intended to include the "fragments," "segments," "variants," "analogs," or "chemical derivatives" of a molecule.

As used herein, a molecule is said to be a "chemical derivative" of another molecule when it contains additional chemical moieties not normally a part of the molecule. Such moieties can improve the molecule's solubility, absorption, biological half life, and the like. The moieties can alternatively decrease the toxicity of the molecule, eliminate or attenuate any undesirable side effect of the molecule, and the like. Moieties capable of mediating such effects are disclosed in, for example, *Remington's Pharmaceutical Sciences* (1980, Mack Publishing Co., Easton, Pa.). Procedures for coupling such moieties to a molecule are well known in the art.

A "variant" or "allelic or species variant" of a protein or nucleic acid is meant to refer to a molecule substantially similar in structure and biological activity to either the protein or nucleic acid. Thus, provided that two molecules possess a common activity and may substitute for each other, they are considered variants as that term is used herein even if the composition or secondary, tertiary, or quaternary structure of one of the molecules is not identical to that found in the other, or if the amino acid or nucleotide sequence is not identical.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

Preferably, when the nucleic acid encoding the desired protein further comprises a promoter/regulatory sequence, the promoter/regulatory sequence is positioned at the 5' end of the desired protein coding sequence such that it drives expression of the desired protein in a cell.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a cell substantially only if the cell is a cell of the tissue type corresponding to the promoter.

By the term "exogenous nucleic acid" is meant that the nucleic acid has been introduced into a cell or an animal using technology which has been developed for the purpose of facilitating the introduction of a nucleic acid into a cell or an animal.

The term "expression of a nucleic acid "as used herein means the synthesis of the protein product encoded by the nucleic acid. More specifically, expression is the process by which a structural gene produces a polypeptide. It involves transcription of the gene into mRNA, and the translation of such mRNA into a polypeptide.

By the term "positioned at the 5' end" as used herein, is meant that the promoter/regulatory sequence is covalently bound to the 5' end of the nucleic acid whose expression it regulates, at a position sufficiently close to the 5' start site of transcription of the nucleic acid so as to drive expression thereof.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least about twenty sequential nucleotide residues of the polynucleotide. It is understood that a portion of a polynucleotide may include every nucleotide residue of the polynucleotide.

A "polyadenylation sequence" is a polynucleotide sequence which directs the addition of a poly A tail onto a transcribed messenger RNA sequence.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

The term "oligonucleotide or oligomer", as used herein, refers to a molecule comprised of two or more deoxyribonucleotides or ribonucleotides, preferably more than three. Its exact size will depend on many factors, which in turn depend on the ultimate function or use of the oligonucleotide. An oligonucleotide may be derived synthetically or by cloning.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

By the term "amplification primer", as used herein, is meant an oligonucleotide which is capable of annealing adjacent to a target sequence and serving as an initiation point for DNA synthesis when placed under conditions in which synthesis of a primer extension product which is complementary to a nucleic acid strand is initiated.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

One skilled in the art would appreciate, based upon the disclosure provided herein, that to visualize a particular DNA sequence in a hybridization procedure, a labeled DNA molecule or "hybridization probe" can be reacted to a fractionated nucleic acid bound to a nitrocellulose filter. The areas on the filter that carry nucleic acid sequences complementary to the labeled DNA probe become labeled themselves as a consequence of the reannealing reaction. The areas of the filter that exhibit such labeling are visualized. The hybridization probe is generally produced by molecular cloning of a specific DNA sequence.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

A cell that comprises an exogenous nucleic acid is referred to as a "recombinant cell." Such a cell may be a eukaryotic cell or a prokaryotic cell. A gene which is expressed in a recombinant cell wherein the gene comprises a recombinant polynucleotide, produces a "recombinant polypeptide."

"Sequence amplification," as the term is used herein, means a method for generating large amounts of a target sequence. In general, one or more amplification primers are annealed to a nucleic acid sequence. Using appropriate enzymes, sequences found adjacent to, or in between the primers are amplified.

By the term "specifically binds," as used herein, is meant a compound, e.g., a protein, a nucleic acid, an antibody, and the like, which recognizes and binds a specific molecule, but does not substantially recognize or bind other molecules in a sample.

"Steady-state level" refers to a stable condition that does not change over time, or the state in which change in one direction or production of a component is continually balanced by a compensatory change in another.

A "substantially pure" protein or nucleic acid is a protein or nucleic acid preparation that is generally lacking in other cellular components with which it is normally associated in vivo. That is, as used herein, the term "substantially pure" describes a compound, e.g., a nucleic acid, protein or polypeptide, which has been separated from components which naturally accompany it. Typically, a compound is substantially pure when at least about 10%, preferably at least about 20%, more preferably at least about 50%, still more preferably at least about 75%, even more preferably at least about 90%, and most preferably at least about 99% of the total material (by volume, by wet or dry weight, or by mole percent or mole fraction) in a sample is the compound of interest. Purity can be measured by any appropriate method, e.g., by column chromatography, gel electrophoresis or HPLC analysis.

A compound, e.g., a nucleic acid, a protein or polypeptide is also "substantially purified" when it is essentially free of naturally associated components or when it is separated from the native contaminants which accompany it in its natural state. Thus, a "substantially pure" preparation of a nucleic acid, as used herein, refers to a nucleic acid sequence which has been purified from the sequences which flank it in a naturally occurring state, e.g., a DNA fragment which has been removed from the sequences which are normally adjacent to the fragment in a genome in which it naturally occurs.

Similarly, a "substantially pure" preparation of a protein or a polypeptide, as used herein, refers to a protein or polypeptide which has been purified from components with which it is normally associated in its naturally occurring state. A substantially pure peptide can be purified by following known procedures for protein purification, wherein an immunological, enzymatic or other assay is used to monitor purification at each stage in the procedure. Protein purification methods are well known in the art, and are described, for example in Deutscher et al. (1990, In: *Guide to Protein Purification*, Harcourt Brace Jovanovich, San Diego).

By "tag" polypeptide is meant any protein which, when linked by a peptide bond to a protein of interest, may be used to localize the protein, to purify it from a cell extract, to immobilize it for use in binding assays, or to otherwise study its biological properties and/or function. A chimeric (i.e., fusion) protein containing a "tag" epitope can be immobilized on a resin which binds the tag. Such tag epitopes and resins which specifically bind them are well known in the art and include, for example, tag epitopes comprising a plurality of sequential histidine residues (His6), which allows isolation of a chimeric protein comprising such an epitope on nickel-nitrilotriacetic acid-agarose, a hemagglutinin (HA) tag epitope allowing a chimeric protein comprising such an epitope to bind with an anti-HA-monoclonal antibody affinity matrix, a myc tag epitope allowing a chimeric protein comprising such an epitope to bind with an anti-myc-monoclonal antibody affinity matrix, a glutathione-S-transferase tag epitope, and a maltose binding protein (MBP) tag epitope, which can induce binding between a protein comprising such an epitope and a glutathione- or maltose-Sepharose column, respectively. Production of proteins comprising such tag epitopes is well known in the art and is described in standard treatises such as Sambrook et al., 1989, supra, and Ausubel et al., supra. Likewise, antibodies to the tag epitope (e.g., anti-HA, anti-myc antibody 9E10, and the like) allow detection and localization of the fusion protein in, for example, Western blots, ELISA assays, and immunostaining of cells.

By the term "type I collagen," as used herein, is meant any collagen known to be a type I collagen, e.g., pro-α1(I) collagen, pro-α2(I) collagen, and the like, as well as other collagens identified as type I collagen in the future according to criteria that are well-known in the art.

A "vector," as used herein, refers to a plasmid or phage DNA or other DNA sequence into which DNA may be inserted to be cloned. The vector can replicate autonomously in a host cell, and can be further characterized by one or a small number of endonuclease recognition sites at which such DNA sequences can be cut in a determinable fashion and into which DNA may be inserted. The vector can further contain a marker suitable for use in the identification of cells transformed with the vector. The words "cloning vehicle" are sometimes used for "vector."

Additionally, the term "vector" encompasses any plasmid, phage and virus encoding an exogenous nucleic acid. The term also includes non-plasmid and non-viral compounds which facilitate transfer of nucleic acid into virions or cells, such as, for example, polylysine compounds and the like. The vector can be a viral vector which is suitable as a delivery vehicle for delivery of the nucleic acid encoding, e.g., Jagged, soluble Jagged, γ-Jaggged, and/or or a portion thereof, to a cell and/or a patient, or the vector can be a non-viral vector which is suitable for the same purpose.

Examples of viral and non-viral vectors for delivery of DNA to cells and tissues are well-known in the art and are described, for example, in Ma et al. (1997, Proc. Natl. Acad. Sci. U.S.A. 94:12744–12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057–3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

"Expression vector," as the term is used herein, means a vector or vehicle similar to a cloning vector but which is capable of expressing a gene which has been cloned into it, after transformation into a host. The cloned gene is usually placed under the control of (i.e., operably linked thereto) certain regulatory/control sequences such as, e.g., promoter sequences. Expression control sequences will vary depending on whether the vector is designed to express the operably linked gene in a prokaryotic or eukaryotic host and can additionally contain transcriptional elements such as enhancer elements, termination sequences, tissue-specificity elements, and/or translational initiation and termination sites. One skilled in the art would appreciate, based upon the disclosure provided herein and methods well-known in the art, that not all regulatory/control elements need be present in all constructs; rather, the present invention encompasses an expression vector comprising any combination of elements known in the art such that a nucleic acid of interest is expressed as desired.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., retroviruses, adenoviruses, and adeno-associated viruses) that incorporate the recombinant polynucleotide.

Description

Angiogenesis, or the formation of new blood vessels, plays a central role in a number of physiologic and pathologic conditions, including placental development, wound healing, rheumatoid arthritis, diabetic retinopathy and solid tumor growth and metastasis. Endothelial cells comprise a monolayer lining the luminal surface of all blood vessels, thereby playing a central role in this process. In vitro populations of endothelial cells isolated from both large vessels and microvessels can be induced to mimic this differentiation process by forming a capillary-like network. Three-dimensional fibrin gels have been used to mimic angiogenesis, as an in vitro corollary of the in vivo phenomenon since endothelial cells invade blood clots in the process of wound repair.

Cellular differentiation is a well documented process in vitro, generally requiring a transcriptional component for induction. However, in contrast to most cell types, endothelial cell differentiation has been shown to be reversible. Digestion of the endothelial cellular networks formed in vitro, and subsequent culture of the cells in the presence of FGF-1 causes them to revert to an undifferentiated phenotype (see, e.g., Maciag et al., 1982, J. Cell Biol. 94:511–520). However, endothelial cell differentiation has also been shown to have a transcriptional basis. Endothelial cell (HUVEC) organization into a cellular network has been shown to be associated with an increase in the transcript encoding fibronectin, and a decrease in the transcript encoding sis, which reverses when the cellular network is digested with proteases and the cells revert to the proliferative phenotype (see, e.g., Jaye et al., 1985, Science 228:882–885).

HUVEC are capable of two different behaviors, both of which are termed "differentiation." The first is the formation of a two dimensional network involving cell elongation, anastomosis and branching that does not require transcription and translation, but requires post-translational modification. The second is a more complex three-dimensional process resulting in a capillary network containing lumens, which Zimrin et al. (1995), have shown requires both transcriptional and post-translational events. In addition, Zimrin et al. (1995), has defined the modified differential display technique as applied to endothelial cells and demonstrated that it is a very useful method of isolating transcripts which are differentially expressed as endothelial cells differentiate.

Thus, in the present invention, using a modification of the differential display method, the human homolog of the Jagged ligand for the Notch receptor has been isolated from human umbilical vein endothelial cells (HUVEC) invading a fibrin gel. The addition of an antisense Jagged oligonucleotide to bovine microvascular endothelial cells on collagen resulted in a marked increase in their invasion into the collagen gel in response to FGF-2. However, while the antisense Jagged oligonucleotide of the present invention was also able to increase the migration of bovine microvascular endothelial cells on fibronectin, the oligonucleotide significantly decreased the migration of bovine endothelial cells derived from the aorta, suggesting a divergence in the mechanism utilized by two different endothelial cell populations to respond to the Notch signaling system.

The distinction between microvascular and large vessel endothelium is well recognized as a part of the heterogeneity of the vascular endothelium in general and this is reflected in the properties of endothelial cells from different sources in cell culture (Carson and Haudenschild, 1986, In Vitro 22:344–354), and in organ-specific expression of different adhesion molecules, cell surface glycoproteins and lectin-binding sites (Gumkowski et al., 1987, Blood Vessels 24:11).

Briefly, to identify the molecular events necessary in the process of angiogenesis, a modified differential display procedure was used to isolate messages that were differentially expressed in HUVEC plated on fibrin in the presence of FGF-1 over the course of 24 hours. As described in Example 2, infra, one of the cDNAs that was amplified at 2 hours, and which was found to be highly homologous to the rat Jagged transcript was identified as an isolate of the human Jagged homolog. The putative protein sequence of the present invention includes a signal peptide, a DSL domain shared by the Notch ligands Delta, Serrate, Lag-2 and Apx-1, sixteen tandem epidermal growth factor-like repeats, a cysteine-rich region, a transmembrane domain and a cytoplasmic tail. The 5' end of the sequence of the human Jagged isolate corresponds to position 417 of the rat sequence, at the eleventh codon of the predicted 21 residue signal peptide.

Figure 5:
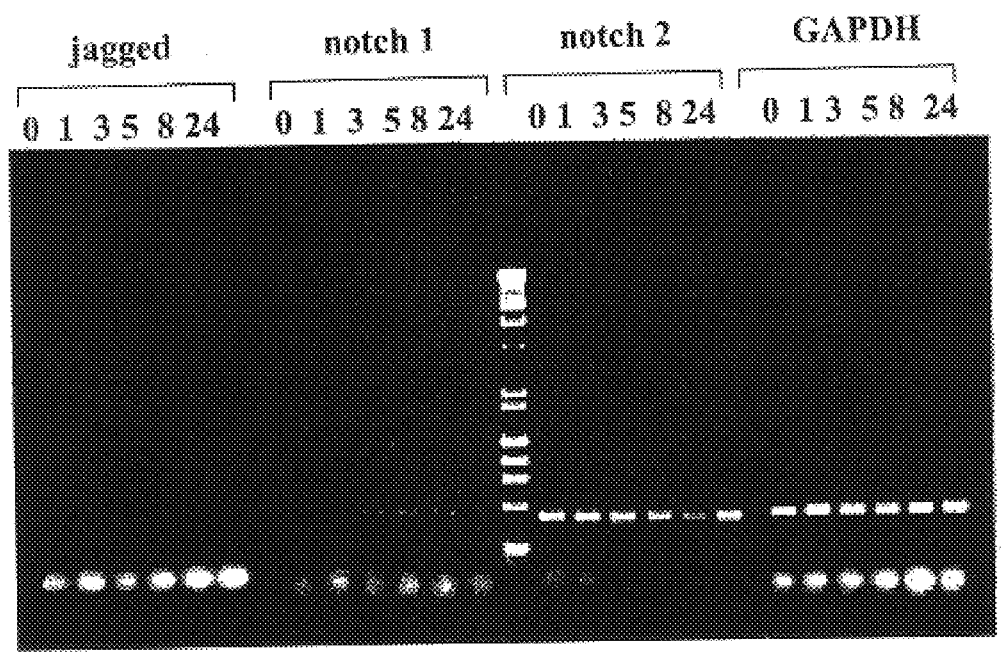
FIG. 5 is an image of a gel depicting the RT-PCR analysis of steady-state levels of Jagged, Notch I and Notch 2 transcripts in HUVEC. Glyceraldehyde-3-phosphate dehydrogenase (GAPDH) was used as a positive control.

To investigate the role of Jagged and Notch in endothelial cell behavior, reverse transcription and polymerase chain reaction amplification (RT-PCR) was used to evaluate the steady-state message levels of Jagged and two related Notch proteins, human TAN-1 and human Notch group protein, in human endothelial cells on fibrin (FIG. 5). Although the Jagged message was found to be up-regulated in populations of HUVEC exposed to fibrin at the 3 hour timepoint, the message levels of the two Notch proteins was not changed over the course of 24 hours. Thus, it is shown in the present invention that the human endothelial cell population is capable of expressing both the Jagged ligand and the Notch receptor, indicating that the human endothelial cell is completing an autocrine signal using the Notch signal transduction pathway. The data do not distinguish, however, between a homogeneous population expressing both Notch and Jagged proteins, or heterogeneous subpopulations of endothelial cells that display Notch, Jagged, both or neither protein.

Therefore, to delineate a functional role for Jagged, an antisense Jagged oligonucleotide was designed in the present invention, which encompassed the Kozak consensus region, the ATG start codon and the next three codons of the rat Jagged cDNA sequence. Similar strategies have previously proved useful as a means of repressing the translational efficiency of a wide variety of transcripts in vitro (see Scanlon et al., 1995, FASEB J. 9:1288–1296; Maier et al., 1990, J. Biol. Chem. 265:10805–10808).

Figure 6:
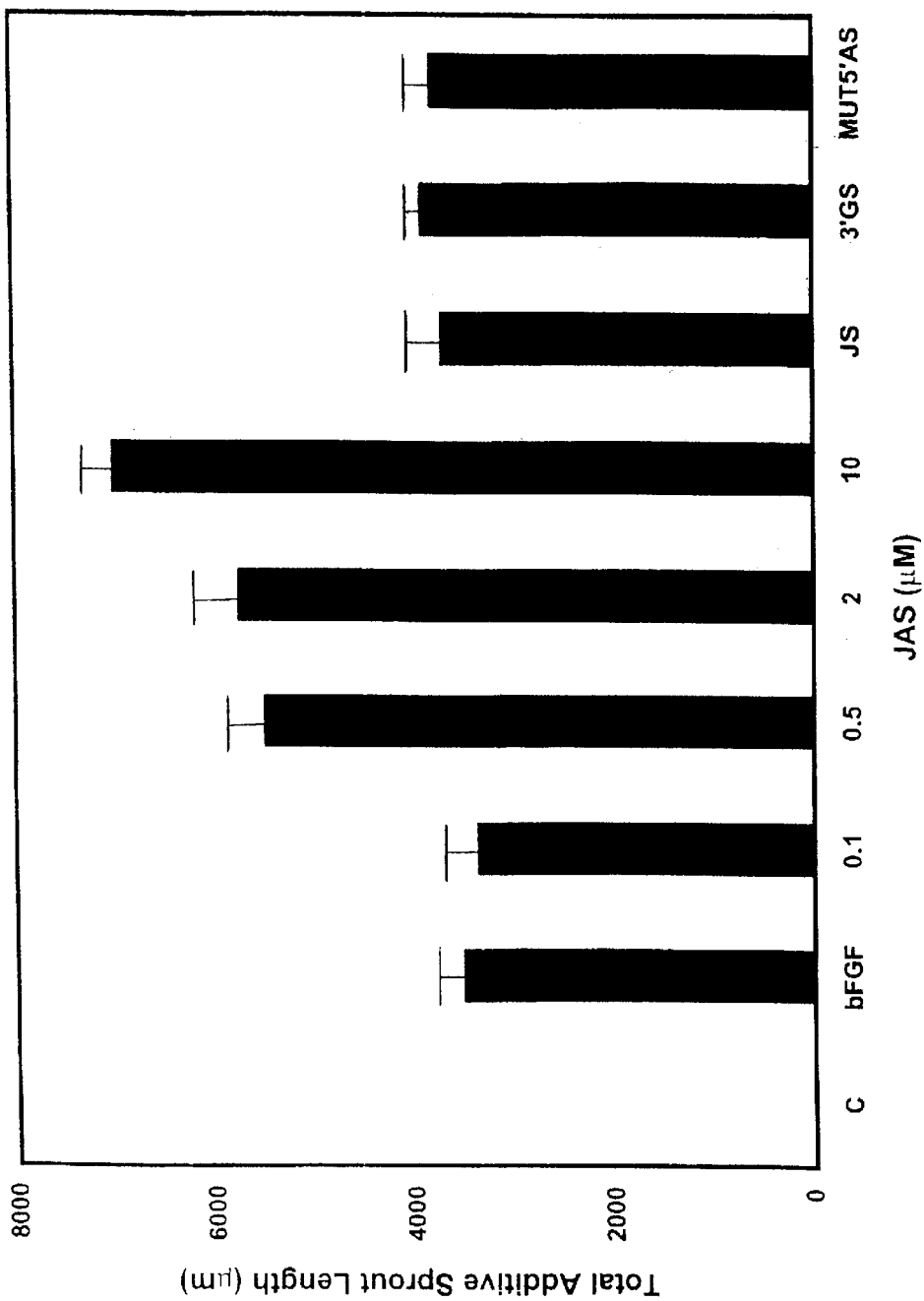
FIG. 6 is a graph depicting the effect of the Jagged antisense oligonucleotide (JAS) (5'-TGGGGACCGCATCGCTGC-3' [SEQ ID NO:29]) on BMEC sprout formation, as compared with the effect on three control oligomers, a Jagged sense oligonucleotide (JS) (5'-GCAGCGATGCGGTCCCCA-3' [SEQ ID NO:30]), a 3' antisense Jagged oligomer (3' AS) (5'-GAATCAAGGCTCCCCTAG-3' [SEQ ID NO:31]), and a mutated 5' antisense Jagged (MUT5' AS) oligomer (5'-TGCGGTCCCCAACGGTGG-3' [SEQ ID NO:32]).

Because endothelial cell migration is an important component of angiogenesis, endothelial cell behavior was evaluated under conditions of sprout formation (Montesano and Orci, 1985, Cell 42:469–477) and migration (Sato and Rifkin, 1988, J. Cell Biol. 107:1199–1205). The addition of the oligonucleotide to bovine microvascular endothelial cells plated on collagen at varying concentrations resulted in an oligonucleotide-induced dose-dependent increase in the total length of sprout formation observed in response to the addition of FGF-2 (FIG. 6). The addition of several control oligonucleotides, including a sense oligonucleotide covering the same sequence, a 5' antisense oligonucleotide with every third base mutated, and a random oligonucleotide, had no effect on the total length of sprout formation (FIG. 6). Thus, the addition of the antisense Jagged oligonucleotide significantly enhanced endothelial cell sprout formation beyond the level achieved by FGF-2.

These data were unusual since endothelial cell sprout formation requires cell migration as a component, and the Jagged cDNA had been isolated from a human endothelial cell system where migration into the fibrin clot also occurs. Consequently, the effect of the antisense Jagged oligonucleotide was studied on capillary and large vessel endothelial cell migration, respectively. It was found that while a bovine microvascular endothelial cell population exhibited a significant dose-dependent increase in their migration in the presence of the Jagged antisense oligonucleotide (FIG. 7A), the migration of bovine aorta endothelial cells was significantly attenuated in a dose-dependent fashion by the antisense Jagged oligonucleotide (FIG. 7B). Thus, the ability of Jagged-Notch signaling to modify endothelial cells was dependent upon the anatomic source of the endothelial cells.

Since the endothelial cells studied were from both large and small vessels responded to the antisense Jagged oligonucleotide in a disparate manner, and both cellular populations are likely to express the Notch receptor, the difference in their response to the Jagged antisense oligonucleotide indicates for the first time that there are differences between large and small vessels in the Notch signaling pathway. Although it has been documented that cells isolated from small vessels are able to undergo the phenotypic changes characteristic of capillary formation more readily than endothelial cells isolated from large vessels (Ingber and Folkman, 1989, J. Cell Biol. 109:317–330), the novel response to the Jagged antisense oligonucleotide disclosed in the present invention represents the first demonstration of an effect not only different in degree but also in direction.

The present embodiments further demonstrate that the addition of exogenous Jagged (or enhanced expression of Jagged) produces an effect opposite to that seen in Examples 5–7. In other words, the addition or increased expression of Jagged decreases the migration and invasion of microvascular cells from the vaso vasorum, and increases or stimulates the migration of large vessel endothelial cells.

The clinical importance of the disparate effect of the Jagged-Notch signaling pathway on the macro- and micro-diameter blood vessels is significant, offering a solution to many aspects of vascular pathophysiology. For example, the morbidity and mortality from hypertension is clearly based on the disease of the large vessels (atherosclerosis and stroke), but in the major forms of hypertension, the actual cause for elevated blood pressure lies in the peripheral vascular beds (arterioles and microvasculature) (Chobanian et al., 1986, Hypertension 8:15–21). The presently defined compositions and methods may resolve the previously unanswered question of how hypertension could be directly related to the aortic intima and atherosclerosis, and vice versa, how known atherogenic risk factors could affect the microvascular endothelium (Chan et al., 1979, Microvasc. Res. 18:353–369).

Moreover, the presently embodied compositions and methods are useful for the modification of a post-angioplastic situation, when one or more large coronary vessel have been stripped of their endothelial cell lining. One of the most serious complications limiting the value of the angioplastic procedure is the occurrence of restenosis or the rapid migration and proliferation of smooth muscle cells, monocytes/macrophages, platelets, and endothelium at the wound site resulting in a reocclusion of the vessel that may be more extensive than before treatment (see numerous review articles on the subject, e.g., Schwartz et al., 1981, Atherosclerosis 1:107–161). However, treating the wounded or injured area with a therapeutic amount of additional recombinant Jagged protein, or a functionally equivalent drug or protein having the ability to signal Notch, will prevent or inhibit reocclusion by increasing the migration of the large vessel endothelial cells on the borders of the lesion into the denuded area to cover the lesion, while also decreasing emergence of the micro-vascular cells (smooth muscle, endothelial, macrophage, etc.) from the vaso vasorum and providing the nutrient microvessels or sprouts to supply the proliferating smooth muscle cells.

In a preferred embodiment, the present invention provides highly purified Jagged protein. As used herein, a protein is said to be highly purified if the protein possesses a specific activity that is greater than that found in whole cell extracts containing the protein.

Any eukaryotic organism can be used as a source of Jagged, or the genes encoding the same, as long as the source organism naturally contains the ligand or its equivalent. As used herein, "source organism" refers to the original organism from which the amino acid or DNA sequence is derived, regardless of the organism the ligand is expressed in or ultimately isolated from. For example, a human is said to be the "source organism" of Jagged expressed by an insect expression system as long as the amino acid sequence is that of human Jagged. The most preferred source organism is human.

A variety of methodologies known in the art can be utilized to obtain the Jagged proteins of the present invention. In one embodiment, the Jagged is purified from tissues or cells which naturally produce it, such as HUVEC. One skilled in the art can readily follow known methods for isolating proteins in order to obtain the Jagged protein. These include, but are not limited to, immunochromatography, size-exclusion chromatography, ion-exchange chromatography, affinity chromatography, HPLC, and the methods set forth by example in the present disclosure. One skilled in the art can readily adapt known purification schemes to delete certain steps or to incorporate additional purification procedures.

In another embodiment, the ligand is purified from cells which have been altered to express the desired protein. As used herein, a cell is said to be "altered to express a desired protein" when the cell, through genetic manipulation, is made to produce a protein which it normally does not produce, or which the cell normally produces at low levels. One skilled in the art can readily adapt procedures for introducing and expressing either genomic or cDNA sequences into either eukaryotic or prokaryotic cells, in order to generate a cell which produces the desired protein.

There are a variety of source organisms for DNA encoding the desired protein. The more preferred source is the endothelial cell. The most preferred source is the human endothelial cell. The embodied methods are readily adapted to use of an HUVEC population as a model to be evaluated in comparison with HU artery (A) EC and human cells obtained from other anatomic sites. These include human adipose-derived microvascular endothelial cells (HMEC), human dermis-derived capillary endothelial cells (HCEC) and human saphenous vein (HSVEC) and artery (HSAEC). Many human endothelial cell populations are readily available from commercial (HMEC and HCEC) and academic sources (HSVEC and HSAEC were provided by Dr. Michael Watkins, Dept. of Surgery, Boston University; and HUAEC were provided by Dr. Victor van Hinsbergh, Gabius Institute, Netherlands).

In yet another embodiment, since probes are available which are capable of hybridizing to Jagged, DNA sequences encoding the desired nucleic acid sequence encoding the protein of interest can be obtained by routine hybridization and selection from any host which possesses these receptors. A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the gene sequence encoding Jagged may be obtained by the above-described methods. This region may be retained for its transcriptional termination regulatory sequences, such as termination and polyadenylation. Thus, by retaining the 3'-region naturally contiguous to the DNA sequence encoding Jagged, the transcriptional termination signals may be provided. Where the transcriptional termination signals are not satisfactorily functional in the expression host cell, then a 3' region functional in the host cell may be substituted.

Two DNA sequences (such as a promoter region sequence and the Jagged encoding sequence) are said to be operably linked if the nature of the linkage between the two DNA sequences does not (1) result in the introduction of a frame-shift mutation, (2) interfere with the ability of the promoter region sequence to direct the transcription of the Jagged gene sequence, or (3) interfere with the ability of the Jagged gene sequence to be transcribed by the promoter region sequence. Thus, a promoter region would be operably linked to a DNA sequence if the promoter were capable of effecting transcription of that DNA sequence. To express Jagged, transcriptional and translational signals recognized by an appropriate host are necessary.

In another embodiment, the nucleic acid sequences of the present invention are under controlled expression by the animal or human patient. In the alternative, the nucleic acids sequences are administered to the patient in need of gene therapy, intravenously, intramuscularly, subcutaneously, enterally, topically, parenterally or surgically. When administering the nucleic acids by injection, the administration may be by continuous administration, or by single or multiple administrations. The gene therapy is intended to be provided to the recipient mammal in a "pharmacologically or pharmaceutically acceptable form" in an amount sufficient to be "therapeutically effective." The nucleic acid is said to be in "pharmaceutically or pharmacologically acceptable form" if its administration can be tolerated by a recipient patient. An amount is said to be "therapeutically effective" (also referred to here and elsewhere as "an effective amount") if the dosage, route of administration, etc., of the agent are sufficient to affect a response to Jagged. The nucleic acid is considered to be in "pharmaceutically or pharmacologically acceptable form" if its administration can be tolerated by a recipient patient.

The present invention further encompasses the expression of the Jagged protein (or a functional derivative thereof) in either prokaryotic or eukaryotic cells. Preferred prokaryotic hosts include bacteria such as *E. coli*, Bacillus, Streptomyces, Pseudomonas, Salmonella, Serratia, etc. Under such conditions, the Jagged will not be glycosylated. The prokaryotic host must be compatible with the replicon and control sequences in the expression plasmid.

However, prokaryotic systems may not prove efficacious for the expression of a soluble Jagged ligand, since the protein of interest contains 1045 residues encompassing residue 22 (after the signal sequence) to residue 1067 (prior to the transmembrane domain). While prokaryotic expression systems, e.g., pET3c, have been used to express high molecular weight proteins, such as a biologically active (molecular weight ($M_r$) approximately 118 kDa) FGF-1:β-galactosidase chimera (Shi et al., 1997, J. Biol. Chem. 272:1142–1147), successful folding and disulfide bond formation for the multiple EGF repeats (three disulfide bonds per EGF repeat) in the Jagged sequence may be difficult to accomplish in bacteria.

Nevertheless, to express Jagged (or a functional derivative thereof) in a prokaryotic cell, it is necessary to operably link the Jagged coding sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, etc. Examples of inducible prokaryotic promoters include the major right and left promoters of bacteriophage λ ($P_L$ and $P_R$), the trp, reca, lacZ, lacI, and gal promoters of *E. coli*, the α-amylase (Ulmanen et al., 1985, J. Bacteriol. 162:176–182) and the ζ-28-specific promoters of *B. subtilis* (Gilman et al., 1984, Gene Sequence 32:11–20), the promoters of the bacteriophages of Bacillus (Gryczan, 1982, In: The Molecular Biology of the Bacilli, Academic Press, Inc., NY), and Streptomyces promoters (Ward et al., 1986, Mol. Gen. Genet. 203:468–478). See also reviews by Glick (1987, J. Ind. Microbiol. 1:277–282), Cenatiempo (1986, Biochimie 68:505–516), and Gottesman (1984, Ann. Rev. Genet. 18:415–442).

Proper expression in a prokaryotic cell also requires the presence of a ribosome binding site upstream of the gene sequence-encoding sequence. Such ribosome binding sites are disclosed, for example, by Gold et al. (1981, Ann. Rev. Microbiol. 35:365–404).

Preferred eukaryotic hosts include yeast, fungi, insect cells, mammalian cells, either in vivo or in tissue culture. Mammalian cells which may be useful as hosts include HeLa cells, cells of fibroblast origin such as VERO or CHO-K1, or cells of lymphoid origin, such as the hybridoma SP2/O-AG14 or the myeloma P3x63Sg8, and their derivatives. Preferred mammalian host cells include SP2/0 and J558L, as well as neuroblastoma cell lines such as IMR 332 that may provide better capacities for correct post-translational processing.

For a mammalian host, several possible vector systems are available for the expression of Jagged. A wide variety of transcriptional and translational regulatory sequences may be employed, depending upon the nature of the host. The transcriptional and translational regulatory signals may be derived from viral sources, such as adenovirus, bovine papilloma virus, Simian virus, or the like, where the regulatory signals are associated with a particular gene sequence which has a high level of expression. Alternatively, promoters from mammalian expression products, such as actin, collagen, myosin, etc., may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Yeast expression systems can also carry out posttranslational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). Any of a series of yeast gene sequence expression systems incorporating promoter and termination elements from the actively expressed gene sequences coding for glycolytic enzymes produced in large quantities when yeast are grown in mediums rich in glucose can be utilized. Known glycolytic gene sequences can also provide very efficient transcriptional control signals. For example, the promoter and terminator signals of the phosphoglycerate kinase gene sequence can be utilized.

The more preferred host for a protein the size of Jagged is insect cells, for example the Drosophila larvae. Using insect cells as hosts, the Drosophila alcohol dehydrogenase promoter can be used (see, e.g., Rubin, 1988, Science 240:1453–1459).

The baculovirus insect cell expression system is the most preferred system for expressing the soluble Jagged construct (residues 1–1069) as a carboxy-terminal triple tandem myc-epitope repeat:glutathione-S-transferase (GST) fusion protein chimera, using conventional PCR methods (Zhan et al., 1994, J. Biol. Chem. 269:20221–20224). These include the use of recombinant circle PCR to synthesize the soluble Jagged-Myc-GST construct (sJMG), the preparation and expression of the recombinant virus, AcNPV-GsJ in Sf9 cells (Summers and Smith, 1988, In: A Manual of Methods for Baculovirus Vectors and Insect Culture Procedures, Texas Experimental Station Bulletin #1555), the use of GST affinity chromatography (Zhan et al., 1994) and reversed phase or ion exchange HPLC to purify the recombinant protein from Sf9 cell lysates and Myc immunoblot analysis to monitor the purification and assess the purity of the sJMG protein.

As more fully set forth elsewhere herein, the sJMG construct may not only prove to be valuable for the baculovirus expression system, but it is a useful construct for the expression of a secreted and soluble extracellular Jagged ligand in mammalian cells for implantation in vivo. Thus, the sJM construct—lacking the GST fusion domain—was inserted into the pMEXneo vector and stable NIH 3T3 cell transfectants were obtained following selection with G418 as described (Zhan et al., 1992, Biochem. Biophys. Res. Commun. 188:982–991).

Indeed, in one embodiment, a nucleic acid encoding a soluble Jagged was inserted into the pMEXneo vector and was used to successfully transfect NIH 3T3 cells. When injected into athymic nude mice, the transfectants formed tissue masses demonstrating prominent angiogenesis. Further, the soluble Jagged transfectants demonstrated altered growth morphology in vitro forming chord-like structures when plated in plastic dishes in the presence or absence of a collagen matrix. Further, soluble Jagged transfectants demonstrated a prominent angiogenic response on chorioallantoic membrane angiogenic (CAM) assays.

The soluble Jagged construct disclosed herein is missing both the intracellular and transmembrane domains of the full-length Jagged protein. However, the present invention should not be construed to be limited to constructs wherein both the transmembrane and intracellular domains are not present in the protein molecule. Rather, the present invention encompasses constructs wherein a certain portion of the Jagged protein is absent whereby the truncated Jagged protein is bound to the cell membrane to a lesser extent than the full-length protein such that a greater amount of the truncated molecule in present in the extracellular milieu than the full-length protein.

Therefore, although the present invention discloses a truncated soluble Jagged protein comprising from about amino acid residue 10 to about residue 1180 of the full length protein, the invention is not limited solely to soluble Jagged containing these amino acid residues. Instead, Jagged protein comprising fewer or greater amino acid residues are encompassed in the soluble Jagged proteins of the invention.

Further, the present invention includes a soluble Jagged protein comprising a tag epitope such as a myc tag epitope. By "tag epitope" is meant any amino acid sequence, or nucleic acid encoding same, which, when linked by a peptide bond to a protein of interest, may be used to localize the protein, to purify it from a cell extract, to immobilize it for use in binding assays, or to otherwise study its biological properties and/or function.

One skilled in the art would appreciate, based upon the disclosure provided herein, that the particular tag epitope which may form part of the soluble Jagged, is not limited to any particular tag epitope. That is, although the present invention includes covalently linking a nucleic acid encoding a myc epitope tag at the 3' end of the nucleic acid encoding the truncated soluble Jagged protein, other tag epitopes such as hemagglutinin, glutathione-S-transferase, myc-pyruvate kinase (myc-PK), His6, maltose biding protein (MBP), and the like, are included in the invention. Thus, any nucleic acid sequence encoding a polypeptide which may function in a manner substantially similar to these tag polypeptides should be included in the present invention.

Moreover, baculovirus vectors can be engineered to express large amounts of Jagged in insect cells (Jasny, 1987, Science 238:1653; Miller et al., 1986, In: Genetic Engineering, vol. 8, pp. 277–297, Setlow et al., eds., Plenum Press).

As discussed above, expression of Jagged in eukaryotic hosts requires the use of eukaryotic regulatory regions. Such regions will, in general, include a promoter region sufficient to direct the initiation of RNA synthesis. Preferred eukaryotic promoters include: the promoter of the mouse metallothionein I gene sequence (Hamer et al., 1982, J. Mol. Appl. Gen. 1:273–288); the TK promoter of Herpes virus (McKnight, 1982, Cell 31:355–365); the SV40 early promoter (Benoist et al., 1981, Nature 290:304–310); the yeast gal4 gene sequence promoter (Johnston et al., 1982, Proc. Natl. Acad. Sci. USA 79:6971–6975; Silver et al., 1984, Proc. Natl. Acad. Sci. USA 81:5951–5955).

As is widely known, translation of eukaryotic mRNA is initiated at the codon which encodes the first methionine. For this reason, it is preferable to ensure that the linkage between a eukaryotic promoter and a DNA sequence which encodes Jagged (or a functional derivative thereof) does not contain any intervening codons which are capable of encoding a methionine (i.e., AUG). The presence of such codons results either in a formation of a fusion protein (if the AUG codon is in the same reading frame as the Jagged coding sequence) or a frame-shift mutation (if the AUG codon is not in the same reading frame as the Jagged coding sequence).

The Jagged coding sequence and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the Jagged may occur through the transient expression of the introduced sequence. Alternatively, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama (1983, Molec. Cell. Biol. 3:280–291).

In a preferred embodiment, the introduced sequence is incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids, such as those capable of replication in *E. coli* (such as, for example, pBR322, ColE1, pSC101, pACYC 184, πVX. Such plasmids are, for example, disclosed by Maniatis et al. (1982, In: Molecular Cloning, A Laboratory Manual, Cold Spring Harbor Press, Cold Spring Harbor, N.Y.). Bacillus plasmids include pC194, pC221, pT127, etc. Such plasmids are disclosed by Gryczan (1982, In: The Molecular Biology of the Bacilli, pp. 307–329, Academic Press, NY). Suitable Streptomyces plasmids include pIJ101 (Kendall et al., 1987, J. Bacteriol. 169:4177–4183), and streptomyces bacteriophages such as φC31 (Chater et al., 1986, In: Sixth International Symposium on Actinomycetales Biology, pp. 45–54, Akademiai Kaido, Budapest, Hungary). Pseudomonas plasmids are reviewed by John et al. (1986, Rev. Infect. Dis. 8:693–704), and Izaki (1978, Jpn. J. Bacteriol. 33:729–742).

Preferred eukaryotic plasmids include BPV, vaccinia, SV40, 2-micron circle, etc., or their derivatives. Such plasmids are well known in the art (Botstein et al., 1982, Miami Wntr. Symp. 19:265–274; Broach, 1981, In: The Molecular Biology of the Yeast Saccharomyces: Life Cycle and Inheritance, pp. 445–470, Cold Spring Harbor Laboratory, Cold Spring Harbor, N.Y.; Broach, 1982, Cell 28:203–204; Bollon et al., 1980, J. Clin. Hematol. Oncol. 10:39–48; Maniatis, 1980, "Gene Sequence Expression," In: Cell Biology: A Comprehensive Treatise, vol. 3, pp. 563–608, Academic Press, NY).

Once the vector or DNA sequence containing the construct(s) has been prepared for expression, the DNA construct(s) may be introduced into an appropriate host cell by any of a variety of suitable means: transformation, transfection, conjugation, protoplast fusion, electroporation, calcium phosphaie-precipitation, direct microinjection, etc. After the introduction of the vector, recipient cells are grown in a selective medium, which selects for the growth of vector-containing cells. Expression of the cloned gene sequence(s) results in the production of Jagged, or fragments thereof. This can take place in the transformed cells as such, or following the induction of these cells to differentiate (for example, by administration of bromodeoxyuracil to neuroblastoma cells or the like).

The Jagged proteins (or a functional derivatives thereof) of the present invention can be used in a variety of procedures and methods, such as for the generation of antibodies, for use in identifying pharmaceutical compositions, and for studying DNA/protein interaction.

The peptides of the present invention may also be administered to a mammal intravenously, intramuscularly, subcutaneously, enterally, topically or parenterally. When administering peptides by injection, the administration may be by continuous injections, or by single or multiple injections. The peptides are intended to be provided to a recipient mammal in a "pharmacologically or pharmaceutically acceptable form" in an amount sufficient to "therapeutically effective." A peptide is considered to be in "pharmaceutically or pharmacologically acceptable form" if its administration can be tolerated by a recipient patient. An amount is said to be "therapeutically effective" (an "effective amount") if the dosage, route of administration, etc., of the agent are sufficient to affect a response to Jagged. Thus, the present peptides can be used to increase or enhance the effect of the Jagged protein.

In another embodiment of the present invention, methods for inhibiting, decreasing or preventing the activity of the Jagged peptide can be achieved by providing an agent capable of binding to the ligand (or a functional derivative thereof). Such agents include, but are not limited to: anti-sense Jagged, the antibodies to Jagged (anti-Jagged), and the secondary or anti-peptide peptides of the present invention. By decreasing the activity of Jagged, the affects which the expression of the peptide has on angiogenesis or restenosis can be modified.

In one example of the present invention, methods are presented for decreasing the expression of Jagged (or a functional derivative thereof) by means of an anti-sense strand of cDNA to disrupt the translation of the Jagged message. Specifically, a cell is modified using routine procedures such that it expresses an antisense message, a message which is complementary to the pseudogene message. By constitutively or inducibly expressing the antisense RNA, the translation of the Jagged mRNA can be regulated. Such antisense technology has been successfully applied to regulate the expression of poly(ADP-ribose) polymerase (see Ding et al., 1992, J. Biol. Chem. 267:12804–12812).

On the other hand, methods for stimulating, increasing or enhancing the activity of the Jagged peptide can be achieved by providing an agent capable of enhancing the binding capability or capacity of the ligand (or a functional derivative thereof), or by inhibiting or preventing a signal which would diminish or stop the expression of Jagged in the system. Such agents include, but are not limited to, the anti-antisense Jagged peptides of the present invention. By enhancing the activity of Jagged, the effect which the expression of the peptide has on angiogenesis or restenosis can also be modified.

In yet another embodiment, Jagged (or a functional derivative or variant thereof) can be used to produce antibodies or hybridomas. One skilled in the art will recognize that if an antibody is desired that will bind to Jagged, such a ligand would be generated as described above and used as an immunogen. The resulting antibodies are then screened for the ability to bind Jagged. Additionally, the antibody can be screened for its inability to bind Notch.

The antibodies utilized in the above methods can be monoclonal or polyclonal antibodies, as well fragments of these antibodies and humanized forms. Humanized forms of the antibodies of the present invention may be generated using one of the procedures known in the art such as chimerization or CDR grafting.

In general, techniques for preparing monoclonal antibodies are well known in the art (Campbell, 1984, In: Monoclonal Antibody Technology: Laboratory Techniques in Biochemistry and Molecular Biology, Elsevier Science Publishers, Amsterdam, The Netherlands; St. Groth et al., 1980, J. Immunol. Methods 35:1–21). For example, in one embodiment an antibody capable of binding Jagged is generated by immunizing an animal with a synthetic polypeptide whose sequence is obtained from a region of the Jagged protein.

Any animal (mouse, rabbit, etc.) which is known to produce antibodies can be utilized to produce antibodies with the desired specificity, although because of the large size of the Jagged molecule, the rabbit is more preferred. Methods for immunization are well known in the art. Such methods include subcutaneous or interperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. A hybridoma is an immortalized cell line which is capable of secreting a specific monoclonal antibody.

Any one of a number of methods well known in the art can be used to identify the hybridoma cell which produces an antibody with the desired characteristics. These include screening the hybridomas with an ELISA assay, western blot analysis, or radioimmunoassay (Lutz et al., 1988, Exp. Cell Res. 175:109–124).

Hybridomas secreting the desired antibodies are cloned and the class and subclass are determined using procedures known in the art (Campbell, 1984, In: Monoclonal Antibody Technology: Laboratory Techniques in Biochemistry and Molecular Biology, Elsevier Science Publishers, Amsterdam, The Netherlands).

For polyclonal antibodies, antibody containing antisera is isolated from the immunized animal and is screened for the presence of antibodies with the desired specificity using one of the above-described procedures.

Conditions for incubating an antibody with a test sample vary. Incubating conditions depend on the format employed in the assay, the detection methods employed, the nature of the test sample, and the type and nature of the antibody used in the assay. One skilled in the art will recognize that any one of the commonly available immunological assay formats (such as, radioimmunoassays, enzyme-linked immunosorbent assays, diffusion based Ouchterlony, or rocket immunofluorescent assays, or the like) can readily be adapted to employ the antibodies of the present invention. Examples of such assays can be found in Chard (1986, In: An Introduction to Radioimmunoassay and Related Techniques, Elsevier Science Publishers, Amsterdam, The Netherlands; Bullock et al., In: Techniques in Immunocytochemistry, Academic Press, Orlando, Fla., vol. 1 (1982), vol. 2 (1983), vol. 3 (1985); Tijssen, 1985, In: Practice and Theory of Enzyme Immunoassays: Laboratory Techniques in Biochemistry and Molecular Biology, Elsevier Science Publishers, Amsterdam, The Netherlands).

The anti-Jagged antibody is also effective when immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling antibodies to such solid supports are well known in the art (Weir et al., 1986, In: Handbook of Experimental Immunology, chapter 10, 4th ed., Blackwell Scientific Publications, Oxford, England; Jacoby et al., 1974, In: Methods in Enzymology, vol. 34 Academic Press, N.Y.).

Additionally, one or more of the antibodies used in the above described methods can be detectably labeled prior to use. Antibodies can be detectably labeled through the use of radioisotopes, affinity labels (such as, biotin, avidin, etc.), enzymatic labels (such as, horse radish peroxidase, alkaline phosphatase, etc.) fluorescent labels (such as, FITC or rhodamine, etc.), paramagnetic atoms, etc. Procedures for accomplishing such labelling are well-known in the art (see, e.g., Sternberger et al., 1970, J. Histochem. Cytochem. 18:315–333; Bayer et al., 1979, Meth. Enzym. 62:308–315; Engval et al., 1972, Immunol. 109:129–; Goding, 1976, J. Immunol. Meth. 13:215–226). The labeled antibodies of the present invention can be used for, among other things, in vitro, in vivo, and in situ assays to identify cells or tissues which express a specific protein or ligand.

In an embodiment of the above methods, the antibodies are labeled, such that a signal is produced when the antibody (s) bind to the same molecule. One such system is described in U.S. Pat. No. 4,663,278.

The antibodies or antisense peptides of the present invention may be administered to a mammal intravenously, intramuscularly, subcutaneously, enterally, topically or parenterally. When administering antibodies or peptides by injection, the administration may be by continuous injections, or by single or multiple injections.

The antibodies or antisense peptides of the present invention are intended to be provided to a recipient mammal in a "pharmaceutically acceptable form" in an amount sufficient to be "therapeutically effective" or an "effective amount". As above, an amount is said to be therapeutically effective (an effective amount), if the dosage, route of administration, etc. of the agent are sufficient to affect the response to Jagged. Thus, the present antibodies may either stimulate or enhance the effect of the Jagged protein, or they may inhibit or prevent the effect of the Jagged protein. Or, secondary antibody(s) may be designed to affect the response to the Jagged antibody(s) per se, i.e., an anti-antibody to Jagged. In the alternative, either an antibody or an anti-antibody may be designed to affect only the anti-sense strand of the ligand.

One skilled in the art can readily adapt currently available procedures to generate secondary antibody peptides capable of binding to a specific peptide sequence in order to generate rationally designed antipeptide peptides, for example see Hurby et al., 1992, "Application of Synthetic Peptides: Antisense Peptides", In: Synthetic Peptides, A User's Guide, pp. 289–307, W.H. Freeman, NY; Kaspczak et al., 1989, Biochemistry 28:9230–9238). As used herein, an agent is said to be "rationally selected or designed" when the agent is chosen based on the configuration of the Jagged peptide.

Anti-peptide peptides can be generated in one of two fashions. First, the anti-peptide peptides can be generated by replacing the basic amino acid residues found in the pseudogene peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine. Alternatively, the anti-peptide peptides of the present invention can be generated by synthesizing and expressing a peptide encoded by the antisense strand of the DNA which encodes the pseudogene peptide. Peptides produced in this fashion are, in general, similar to those described above since codons complementary to those coding for basic residues generally code for acidic residues.

To detect secondary antibodies, or in the alternative, the labeled primary antibody, labelling reagents may include, e.g., chromophobic, enzymatic, or antibody binding reagents which are capable of reacting with the labelled antibody. One skilled in the art will readily recognize that the disclosed antibodies of the present invention can readily be incorporated into one of the established kit formats which are well known in the art.

An antibody is said to be in "pharmaceutically or pharmacologically acceptable form" if its administration can be tolerated by a recipient patient. The antibodies of the present invention can be formulated according to known methods of preparing pharmaceutically useful compositions, whereby these materials, or their functional derivatives, are combined with a pharmaceutically acceptable carrier vehicle. Suitable vehicles and their formulation, inclusive of other human proteins, e.g., human serum albumin, are described, for example, in Remington's Pharmaceutical Sciences, 1980.

In order to form a pharmaceutically acceptable composition which is suitable for effective administration, such compositions will contain an effective amount of an antibody of the present invention together with a suitable amount of carrier. Such carriers include, but are not limited to saline, buffered saline, dextrose, water, glycerol, ethanol, and a combination thereof. The carrier composition may be sterile. The formulation should suit the mode of administration. In addition to carriers, the antibodies of the present invention may be supplied in humanized form.

Humanized antibodies may be produced, for example by replacing an immunogenic portion of an antibody with a corresponding, but non-immunogenic portion (i.e., chimeric antibodies) (Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., European Patent Application 125,023; Better et al., 1988, Science 240:1041–1043; Liu et al., 1987, Proc. Natl. Acad. Sci. USA 84:3439–3443; Liu et al., 1987, J. Immunol. 139:3521–3526; Sun et al., 1987, Proc. Natl. Acad. Sci. USA 84:214–218; Nishimura et al., 1987, Canc. Res. 47:999–1005; Wood et al., 1985, Nature 314:446–449; Shaw et al., 1988, J. Natl. Cancer Inst. 80:1553–1559).

The compositions of the present invention can also include minor amounts of wetting or emulsifying agents, or pH buffering agents. The composition can be a liquid solution, suspension, emulsion, tablet, pill, capsule, sustained release formulation or powder. The composition can be formulated as a suppository with traditional binders and carriers such as triglycerides. Oral formulations can include standard carriers such as pharmaceutically acceptable mannitol, lactose, starch, magnesium stearate, sodium saccharine, cellulose, magnesium carbonate, etc.

In a preferred embodiment of the present invention, the compositions are formulated in accordance with routine procedures for intravenous administration to a subject. Typically, such compositions are carried in a sterile isotonic aqueous buffer. As needed, a composition may include a solubilizing agent and a local anesthetic. Generally, the components are supplied separately or as a mixture in unit dosage form, such as a dry lyophilized powder in a sealed container with an indication of active agent. Where the composition is administered by infusion, it may be provided with an infusion container with a sterile pharmaceutically acceptable carrier. When the composition is administered by injection, an ampoule of sterile water or buffer may be included to be mixed prior to injection.

The therapeutic compositions may also be formulated in salt form. Pharmaceutically acceptable salts include those formed with free amino groups, such as those derived from hydrochloric, phosphoric, acetic, oxalic and tartaric acids, or formed with free carboxyl groups such as those derived from sodium, potassium, ammonium, calcium, ferric hydroxides, isopropylamine, triethylamine, 2-ethylamino ethanol, histidine, procaine, etc.

The dosage of the administered agent will vary depending upon such factors as the patient's age, weight, height, sex, general medical condition, previous medical history, etc. In general, it is desirable to provide the recipient with a dosage of the antibody which is in the range of from about 1 pg/kg to 10 mg/kg (body weight of patient), although a lower or higher dosage may be administered. Suitable ranges for intravenous administration is typically about 20–500 µg of active compound per kilogram body weight. Effective doses may be extrapolated from dose-response curves derived from in vitro and in vivo animal model test systems.

Since highly purified proteins are now available, X-ray crystallography and NMR-imaging techniques can be used to identify the structure of the ligand binding site. Utilizing such information, computer modeling systems are now available that allow one to "rationally design" an agent capable of binding to a defined structure (Hodgson, 1990, Biotechnology 8:1245–1247; Hodgson, 1991, Biotechnology 9:609–613). As used herein, an agent is said to be "rationally designed" if it is selected based on a computer model of the ligand or Notch binding site, or in the alternative, of the ligand binding site on Jagged if activation of the Notch binding site is found to act as an on/off switch affecting the continued expression of Jagged.

In another embodiment of the present invention, methods are provided for modulating the translation of RNA encoding Jagged protein in the cell. Specifically, said method comprises introducing into a cell a DNA sequence which is capable of transcribing RNA which is complimentary to the RNA encoding the Jagged protein. By introducing such a DNA sequence into a cell, antisense RNA will be produced which will hybridize and block the translation of the Jagged protein. Antisense cloning has been described by Rosenberg et al. (1985, Nature 313:703–706), Preiss et al. (1985, Nature 313:27–32), Melton (1985, Proc. Natl. Acad. Sci. USA 82:144–148), and Kim et al. (1985, Cell 42:129–138).

Transcription of the introduced DNA will result in multiple copies of antisense RNA which will be complementary to the Jagged. By controlling the level of transcription of antisense RNA, and the tissue specificity of expression, one skilled in the art can regulate the level of translation of Jagged protein in specific cells within a patient.

In one aspect of the above-described invention, DNA response elements (RE) can be identified which are capable of either stimulating or inhibiting the binding of Jagged. In this manner, assays may be performed to determine binding agents by using any length of DNA so long as it contains at least one RE sequence. In another embodiment, the above such assays are performed in the absence of a RE. In this fashion, agents can be identified which bind to or affect the binding capacity of Jagged independently of DNA binding. Moreover, the above assay can be modified so that it is capable of identifying agents which activate transcription of DNA sequences controlled by a RE.

In the present invention, a cell or organism is altered using routine methods such that it expresses Jagged, or a functional derivative thereof. Moreover, the cell or organism may be further altered to contain a RE operably linked to a reporter sequence, such as luciferase, beta galactosidase, or chloramphenicol acyltransferase. Agents are then incubated with the cell or organism and the expression of the reporter sequence is assayed.

In an alternative usage, nuclear and/or cytosolic extracts from the altered cell containing Jagged or a functional derivative thereof are mixed with an expression module containing an RE operably linked to a reporter sequence. The extract/expression module is incubated with an agent and the expression of the reporter sequence is assayed.

Isolated Nucleic Acid Encoding Soluble Jagged

The invention includes an isolated nucleic acid encoding a soluble Jagged protein. Preferably, the nucleic acid encoding a soluble Jagged is at least about 20% homologous to a nucleic acid having the nucleic acid sequence of SEQ ID NO:17 which is depicted in FIGS. 13B and 13C. The nucleic acid encoding soluble Jagged (SEQ ID NO:17) comprises from about nucleotide 1 to about nucleotide 3201 of full-length Jagged sequence (GenBank Acc. No. U77720, [SEQ ID NO:2]), which sequence is depicted in FIGS. 8B and 8C.

More preferably, the isolated nucleic acid encoding a soluble Jagged is at least about 20% homologous, more preferably, at least about 30%, homologous, preferably, at least about 40%, more preferably, at least about 50%, even more preferably, at least about 60%, more preferably, at least about 70%, even more preferably, at least about 80%, yet more preferably, at least about 90% homologous, more preferably, at least about 95% and even more preferably, at least about 99% homologous to (SEQ ID NO:17). More preferably, the isolated nucleic acid encoding a soluble Jagged is soluble Jagged-1. Most preferably, the isolated nucleic acid encoding a soluble Jagged is SEQ ID NO:17.

The invention also includes a nucleic acid encoding a soluble Jagged, or a fragment or portion thereof. That is, the invention encompasses a nucleic acid encoding less than the full-length soluble Jagged disclosed herein. This is because one skilled in the art would appreciate, based upon the disclosure provided herein, that a nucleic acid encoding less than the full-length soluble Jagged can be useful for a variety of purposes included providing portions of the protein for use in antibody production, treatments related to inhibiting Jagged/Notch interactions, repressing expression of type I collagen (which is extremely important in the regulation of fibrotic diseases), and the like.

As used herein, the term "fragment" as applied to a nucleic acid encoding a soluble Jagged, may ordinarily be at least about 30 nucleotides in length, typically, at least about 50 nucleotides, more typically, from about 50 to about 100 nucleotides, preferably, at least about 100 to about 500 nucleotides, even more preferably, at least about 500 nucleotides to about 1000 nucleotides, yet even more preferably at least about 1000 to about 1500, more preferably, at least about 1500 to about 2500 nucleotides, even more preferably, at least about 2500 nucleotides to about 3000 nucleotides, yet even more preferably, at least about 3000 to about 3100, more preferably, at least about 3100 to about 3160, yet more preferably, at least about 3160 to about 3200, and most preferably, the nucleic acid fragment will be greater than about 3200 nucleotides in length.

As applied to a protein, a soluble Jagged "fragment" is about 30 amino acids in length. More preferably, the fragment is about 40 amino acids, even more preferably, at least about 100, yet more preferably, at least about 200, even more preferably, at least about 500, yet more preferably, at least about 750, even more preferably, at least about 800, yet more preferably, at least about 850, more preferably, at least about 900, yet more preferably, at least about 950, even more preferably, at least about 1000, yet more preferably, at least about 1050, yet more preferably, at least about 1060, and more preferably, at least about 1060 amino acids in length.

The invention includes a nucleic acid encoding a soluble Jagged wherein optimally a nucleic acid encoding a tag polypeptide is covalently linked thereto. That is, the invention encompasses a chimeric nucleic acid wherein a nucleic acid sequence encoding a tag polypeptide is covalently linked to a nucleic acid encoding soluble Jagged. Such chimeric (i.e., fusion) tag polypeptides are well known in the art and include, for instance, myc, myc-pyruvate kinase (myc-PK), His$_6$, maltose biding protein (MBP), glutathione-S-transferase (GST), and green fluorescence protein (GFP). However, the invention is not limited to the nucleic acids encoding the above-listed tag polypeptides. Rather, any nucleic acid sequence encoding a polypeptide which can function in a manner substantially similar to these tag polypeptides should be construed to be included in the present invention. Further, more than one tag polypeptide can be expressed along with a nucleic acid encoding a protein of interest. That is, one skilled in the art would understand, based upon the disclosure provided herein, that more than one tag polypeptide can be covalently linked with a soluble Jagged protein.

A nucleic acid encoding a protein of interest (e.g., soluble Jagged, and any mutant, derivative, variant, or fragment thereof) comprising a nucleic acid encoding a tag polypeptide and a fusion protein produced therefrom can be used to, among other things, localize soluble Jagged within a cell and to study expression, localization, and role(s) of the tagged protein in a cell before, during, and/or after exposing the cell to a test compound. Further, addition of a tag to a protein of interest facilitates isolation and purification of the "tagged" protein such that the protein of interest can be easily produced and purified.

In other related aspects, the invention includes a nucleic acid encoding a soluble Jagged operably linked to a nucleic acid comprising a promoter/regulatory sequence such that the nucleic acid is preferably capable of directing expression of the protein encoded by the nucleic acid.

Expression of soluble Jagged, either alone or fused to a detectable tag polypeptide, in cells which either do not normally express soluble Jagged or which do not express soluble Jagged comprising a tag polypeptide, can be accomplished by operably linking the nucleic acid encoding soluble Jagged to a promoter/regulatory sequence which serves to drive expression of the protein, with or without a tag polypeptide, in a cell into which the exogenous nucleic acid is introduced.

As disclosed previously elsewhere herein, many promoter/regulatory sequences useful for driving constitutive expression of a gene are available in the art and include, but are not limited to, for example, the cytomegalovirus immediate early promoter enhancer sequence, the SV40 early promoter, both of which were used in the experiments disclosed herein, as well as the Rous sarcoma virus promoter, and the like. Moreover, inducible and tissue specific expression of the nucleic acid encoding soluble Jagged can be accomplished by placing the nucleic acid encoding soluble Jagged, with or without a tag polypeptide, under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In addition, promoters which are well known in the art which are induced in response to inducing agents such as metals, glucocorticoids, and the like, are also contemplated in the invention. Thus, it will be appreciated that the invention includes the use of any promoter/regulatory sequence, which is either known or unknown, and which is capable of driving expression of the desired protein encoded by a nucleic acid operably linked to the promoter/regulatory sequence.

Expressing soluble Jagged using a promoter/regulatory sequence allows the isolation of large amounts of recombinantly produced protein. Further, where the lack or decreased level of soluble Jagged expression causes a disease, disorder, or condition associated with such expression, the expression of the protein driven by a promoter/regulatory sequence can provide useful therapeutics including, but not limited to, gene therapy whereby the protein is provided.

Vectors

The invention also includes a vector comprising a nucleic acid encoding a soluble Jagged. Methods for incorporating a desired nucleic acid into a vector and the choice of vectors is well-known in the art as described in, for example, Sambrook et al.,.supra, and Ausubel et al., supra, and are disclosed elsewhere herein.

Further, the invention encompasses expression vectors and methods for the introduction of exogenous nucleic acid encoding soluble Jagged into a cell with concomitant expression of the exogenous nucleic acid in the cell using such methods as those described in, for example, Sambrook et al. (1989, supra), and Ausubel et al. (1997, supra), and as disclosed elsewhere herein.

Selection of any particular plasmid vector or other DNA vector is not a limiting factor in this invention and a wide plethora vectors are well-known in the art (see, e.g., Sambrook et al., supra, and Ausubel et al., supra.). Further, it is well within the skill of the artisan to choose particular promoter/regulatory sequences and operably link those promoter/regulatory sequences to a DNA sequence encoding a desired polypeptide. Such technology is well known in the art and is described, for example, in Sambrook, supra, and Ausubel, supra.

The invention also includes cells, viruses, proviruses, and the like, containing such vectors. Methods for producing cells comprising vectors and/or exogenous nucleic acids are well-known in the art. See, e.g., Sambrook et al., supra; Ausubel et al., supra.

The nucleic acids encoding soluble Jagged can be cloned into various plasmid vectors. However, the present invention should not be construed to be limited to plasmids or to any particular vector. Instead, the present invention should be construed to encompass a wide plethora of vectors which are readily available and/or well-known in the art.

Recombinant Cells

Additionally, the nucleic and amino acids of the invention can be used to produce recombinant cells which are useful tools for the study of soluble Jagged, the identification of novel soluble Jagged-based therapeutics, and for elucidating the cellular role(s) of soluble Jagged, among other things.

Further, the nucleic and amino acids of the invention can be used diagnostically, by assessing either the level of gene expression or protein expression and the biological activity of the protein, to assess severity and prognosis of a disease, disorder, or condition associated with altered level of soluble Jagged gene expression.

The invention also includes expression of soluble Jagged in a cell where it is not normally expressed or expression of soluble Jagged-tagged fusion protein in cells where this fusion protein is not normally expressed. In a preferred embodiment, nucleic acid encoding soluble Jagged was covalently linked with a nucleic acid expressing a tag polypeptide and used to transfect a mammalian cell. Plasmid constructs containing soluble Jagged, or mutants, variants, derivatives and fragments thereof, can be cloned into a wide variety of vectors including a vector comprising a nucleic acid encoding a tag polypeptide. The plasmids can be introduced into a cell using standard methods well-known in the art (e.g., calcium phosphate, electroporation, and the like). Methods for cloning and introducing an isolated nucleic acid of interest into a cell are exemplified herein and are described in, for example, Sambrook et al. (1989, Molecular Cloning: A Laboratory Manual, Cold Spring Harbor Laboratory Press, New York), Ausubel et al. (1997, Current Protocols in Molecular Biology, Green & Wiley, New York), and other standard treatises.

The present invention also encompasses expression of an isolated soluble Jagged of the invention in non-mammalian cells (e.g. yeast, insect, and avian cells) using methods well-known in the art such as those disclosed elsewhere herein. Thus, it is clear that the invention is not limited to any particular vector or to any particular method of introducing the exogenous nucleic acid encoding soluble Jagged into a cell.

Expression of proteins of interest (e.g., soluble Jagged) in a cell, especially when the protein comprises a tag polypeptide, allows localization of the nucleic acid and/or the protein expressed therefrom within the cell under selected conditions such that the function(s) of the protein in the cell can be studied and identified.

One skilled in the art would appreciate, based upon the disclosure provided herein, that the invention also includes expression of soluble Jagged, and the like, in prokaryotic cells (e.g., bacterial cells such as, for example, E. coli ). Accordingly, the invention includes expression of the proteins of the invention in such cells as well.

The invention should not be construed as being limited to these plasmid vectors, bacterial strains, or to these tag polypeptides. Further, the invention is not limited to calcium phosphate transfection or to NIH cells as exemplified herein. Instead, the invention encompasses other expression vectors and methods for the introduction of exogenous DNA into cells with concomitant expression of the exogenous DNA in the cells such as those described, for example, in Sambrook et al. (1989, supra), and Ausubel et al. (1997, supra).

In one embodiment, the cell line is mammalian cell comprising an expression vector comprising a nucleic acid encoding soluble Jagged constitutively expressed under the control of a high-level expression promoter/regulatory sequence. Further, the skilled artisan would appreciate based upon the disclosure provided herein that the cells can be transfected with constructs which comprise soluble Jagged in either a sense (i.e., sense cells) or an antisense orientation (i.e., antisense cells).

One skilled in the art would further appreciate that selected forms of nucleic acids encoding soluble Jagged can be introduced to a cell in order to study the effect of any mutant, derivative, and variant of soluble Jagged (e.g., fusion proteins comprising at least a portion of soluble Jagged and a tag polypeptide) in this system.

Further, the invention includes a recombinant cell comprising an antisense nucleic acid (e.g., γ-soluble Jagged) which cell is a useful model for the study of a disease, disorder, or condition associated with or mediated by inhibition of soluble Jagged biosynthesis and for elucidating the role(s) of soluble Jagged in such processes. That is, the lack of expression of soluble Jagged in patients may indicate, among other things, a disease, disorder or condition. Accordingly, a recombinant (i.e., transgenic) cell comprising an antisense nucleic acid complementary to a nucleic acid encoding soluble Jagged is a useful tool for the study of the mechanism(s) of action of soluble Jagged and its role(s) in the cell and for the identification of therapeutics that ameliorate the effect(s) of decreased levels of soluble Jagged expression.

The invention further includes a recombinant cell comprising an isolated nucleic acid encoding soluble Jagged. The cell can be transiently transfected with a plasmid encoding a portion of the nucleic acid encoding the protein of interest, e.g., soluble Jagged. The nucleic acid need not be integrated into the cell genome nor does it need to be expressed in the cell. Moreover, the cell may be a prokaryotic or a eukaryotic cell and the invention should not be construed to be limited to any particular cell line or cell type.

When the cell is a eukaryotic cell, the cell may be any eukaryotic cell which, when the isolated nucleic acid of the invention is introduced therein, and the protein encoded by the desired gene is no longer expressed therefrom, a benefit is obtained. Such a benefit may include the fact that there has been provided a system in which lack of expression of the desired gene can be studied in vitro in the laboratory or in a mammal in which the cell resides, a system wherein cells comprising the introduced gene deletion can be used as research, diagnostic and therapeutic tools, and a system wherein animal models are generated which are useful for the development of new diagnostic and therapeutic tools for selected disease, disorder, or condition states in a mammal.

Alternatively, the invention includes a eukaryotic cell which, when the isolated nucleic acid of the invention is introduced therein, and the protein encoded by the desired gene, i.e., soluble Jagged, is expressed therefrom where it was not previously present or expressed in the cell or where it is now expressed at a level or under circumstances different than that before the isolated nucleic acid was introduced, a benefit is obtained. Such a benefit may include the fact that there has been provided a system wherein the expression of the desired gene can be studied in vitro in the laboratory or in a mammal in which the cell resides, a system wherein cells comprising the introduced gene can be used as research, diagnostic and therapeutic tools, and a system wherein animal models are generated which are useful for the development of new diagnostic and therapeutic tools for selected disease states in a mammal (e.g., diseases, disorders or conditions of the pituitary mediated by altered expression or activity of soluble Jagged).

Isolated Polypeptides

The invention includes an isolated polypeptide encoded by a nucleic acid encoding a soluble Jagged where the amino acid sequence of the polypeptide is preferably, at least about 30% homologous to the amino acid sequence of soluble Jagged (SEQ ID NO:18). More preferably, the isolated nucleic acid encodes a soluble Jagged which is at least about 40%, more preferably, at least about 50%, even more preferably, at least about 60%, yet more preferably, at least about 70%, more preferably, at least about 80%, even more preferably, at least about 90%, yet more preferably, at least about 95%, and even more preferably, at least about 99% homologous to (SEQ ID NO:18). More preferably, the isolated nucleic acid encodes a soluble Jagged that is soluble Jagged. Most preferably, the isolated nucleic acid encodes a soluble Jagged having the amino acid sequence SEQ ID NO:18.

The invention also includes an isolated polypeptide comprising a soluble Jagged. Preferably, the isolated polypeptide comprising a mammalian soluble Jagged is at least about 30% homologous to SEQ ID NO:18. More preferably, the isolated polypeptide comprising a mammalian soluble Jagged is at least about 40%, more preferably, at least about 50%, even more preferably, at least about 60%, yet more preferably, at least about 70%, more preferably, at least about 80%, even more preferably, at least about 90%, yet more preferably, at least about 95%, and more preferably, at least about 99% homologous to soluble Jagged (SEQ ID NO:18). More preferably, the isolated polypeptide is soluble Jagged. Most preferably, the isolated polypeptide comprising a soluble Jagged is SEQ ID NO:18.

The invention also includes an isolated polypeptide comprising a portion of Jagged. Preferably, the isolated polypeptide comprising a portion of Jagged is at least about 30% homologous to SEQ ID NO:18. More preferably, the isolated polypeptide comprising a portion of soluble Jagged is at least about 40%, more preferably, at least about 50%, even more preferably, at least about 60%, yet more preferably, at least about 70%, more preferably, at least about 80%, even more preferably, at least about 90%, yet more preferably, at least about 95%, and more preferably, at least about 99% homologous to SEQ ID NO:18. More preferably, the isolated polypeptide comprising a portion of soluble Jagged is a portion of Jagged (SEQ ID NO:1) (e.g., from about amino acid 1 to about amino acid 1067). Most preferably, the isolated polypeptide comprising a portion of Jagged is SEQ ID NO:18.

The present invention also provides for analogs of proteins or peptides which comprise a soluble Jagged protein as disclosed herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine;

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention should also be construed to encompass "mutants," "derivatives," and "variants" of the peptides of the invention (or of the DNA encoding the same) which mutants, derivatives and variants are soluble Jagged polypeptides which are altered in one or more amino acids (or, when referring to the nucleotide sequence encoding the same, are altered in one or more base pairs) such that the resulting peptide (or DNA) is not identical to the sequences recited herein, but has the same biological property as the peptides disclosed herein, in that the peptide has biological/biochemical properties of the soluble Jagged protein of the present invention. A biological property of a soluble Jagged includes, but is not limited to include, the ability of the peptide to bind specifically with Notch as demonstrated using, for example, electrophoretic mobility shift assay (EMSA) as disclosed elsewhere herein. Further, another biological activity of soluble Jagged is the ability to affect the level of expression of various nucleic acids enhancing expression of certain genes (e.g., enhancer of split groucho, type IV collagenase, connexin 32, cathepsin D, and vimentin), while mediating reduced levels of expression of other genes (e.g., pro-α-2(I) collagen, FGFR-1, and IkB-β), as determined using serial analysis of gene expression (SAGE) analysis. Further, the activities of soluble Jagged include, but are not limited to, affecting endothelial sprout formation, affecting angiogenesis, the ability to induce development of angiogenic tissue masses in nude mice, and affecting the ability to induce angiogenesis in a CAM angiogenesis model. Additionally, the biological activity of soluble Jagged includes the ability to repress type I collagen expression, which is extremely important in the regulation of all fibrotic diseases.

Further, the invention should be construed to include naturally occurring variants or recombinantly derived mutants of soluble Jagged, which variants or mutants render the protein encoded thereby either more, less, or just as biologically active as the full-length proteins and/or the truncated soluble proteins of the invention.

In addition, the skilled artisan would appreciate that changes can be introduced by mutation of the nucleic acid encoding the protein thereby leading to changes in the amino acid sequence of the encoded protein, without altering the biological activity of the protein. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to polypeptides encoded by nucleic acid molecules of the invention, which polypeptides contain changes in amino acid residues that are not essential for activity. Such polypeptides differ in amino acid sequence from any of SEQ ID NOS:1, and SEQ ID NO:18, yet retain biological activity.

To generate variant proteins, an isolated nucleic acid molecule encoding a variant protein can be created by introducing one or more nucleotide substitutions, additions or deletions into the nucleotide sequence of any of SEQ ID NO:2 and/or SEQ ID NO:17, such that one or more amino acid residue substitutions, additions or deletions are introduced into the encoded soluble Jagged protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

One skilled in the art would appreciate, based upon the disclosure provided herein, that a mutant polypeptide that is a variant of a polypeptide of the invention can be assayed for: (1) the ability to induce expression of certain genes (e.g., enhancer of split groucho, type IV collagenase, connexin 32, cathepsin D, and vimentin); (2) the ability to reduce expression of various genes (e.g., pro-α-2(I) collagen, FGFR-1, and IkB-β); (3) the ability to induce sprout formation; (4) the ability to induce angiogenesis in a CMA model; (5) the ability to induce formation of angiogenic tissue masses in nude mice; and (6) the ability to repress type I collagen expression, which is extremely important in the regulation of all fibrotic diseases.

The nucleic acids, and peptides encoded thereby, are useful tools for elucidating the function(s) soluble Jagged in a cell. Further, they are useful for localizing the nucleic acid, protein, or both, in a cell and for assessing the level of expression of the nucleic acid and/or protein under selected conditions including in response to therapeutic treatment. Further, nucleic and amino acids comprising soluble Jagged are useful diagnostics which can be used, for example, to identify a compound that affects expression of the protein and is a candidate therapeutic for a disease, disorder, or condition associated with altered expression of soluble Jagged.

In addition, the nucleic acids, the proteins encoded thereby, or both, can be administered to a mammal to increase or decrease expression of soluble Jagged in the mammal. This can be therapeutic to the mammal if under or over-expression of soluble Jagged in the mammal mediates a disease or condition associated with altered expression of the protein compared with normal expression of soluble Jagged in a healthy mammal.

Antibodies

The invention also includes an antibody specific for a soluble Jagged, or a portion thereof.

In one embodiment, the antibody is a rabbit polyclonal antibody to soluble Jagged. The antibody can be specific for any portion of the protein and the full-length protein can be used to generate antibodies specific therefor. However, the present invention is not limited to using the full-length protein as an immunogen. Rather, the present invention includes using an immunogenic portion of the protein to produce an antibody that specifically binds with soluble Jagged. That is, the invention includes immunizing an animal using an immunogenic portion of the protein.

The antibodies can be produced by immunizing an animal such as, but not limited to, a rabbit or a mouse with a protein of the invention, or a portion thereof, or by immunizing an animal using a protein comprising at least a portion of soluble Jagged and a tag polypeptide portion comprising, for example; a maltose binding protein tag polypeptide portion and a portion comprising the appropriate soluble Jagged amino acid residues. One skilled in the art would appreciate, based upon the disclosure provided herein, that smaller fragments of these nucleic acids can also be used to produce antibodies that specifically bind soluble Jagged.

One skilled in the art would appreciate, based upon the disclosure provided herein, that various portions of an isolated soluble Jagged polypeptide can be used to generate antibodies to either highly conserved regions of soluble Jagged or to non-conserved regions. As disclosed elsewhere herein, Jagged protein (GenBank Acc. No. U77720, [SEQ ID NO:1]), the amino acid sequence of which is depicted in FIG. 8A, comprises various conserved domains including, but not limited to, a signal peptide (from about amino acid residue 1 to about amino acid residue 21); a DSL domain (from about amino acid residue 185 to about amino acid residue 229); EGF repeats (from about amino acid residue 234 to about amino acid residue 862); a cysteine-rich region (from about amino acid residue 863 to about amino acid residue 1002); a transmembrane domain (from about amino acid residue 1068 to about amino acid residue 1093); and a cytoplasmic region (from about amino acid residue 1094 to about amino acid residue 1218). Once armed with the sequence of Jagged and the detailed analysis localizing the various conserved and non-conserved domains of the protein, the skilled artisan would understand, based upon the disclosure provided herein, how to obtain antibodies specific for the various domains using methods well-known in the art.

Further, the skilled artisan, based upon the disclosure provided herein, would appreciate that the non-conserved regions of a protein of interest can be more immunogenic than the highly conserved regions which are conserved among various organisms. Immunization using a non-conserved immunogenic portion can produce antibodies specific for the non-conserved region thereby producing antibodies that do not cross-react with other proteins which can share one or more conserved portions.

One skilled in the art would appreciate, based upon the disclosure provided herein, which portions of soluble Jagged are less homologous with other proteins sharing conserved domains. However, the present invention is not limited to any particular domain; instead, the skilled artisan would understand that other non-conserved regions of the soluble Jagged proteins of the invention can be used to produce the antibodies of the invention as disclosed herein.

The invention should not be construed as being limited solely to the antibodies disclosed herein or to any particular immunogenic portion of the proteins of the invention. Rather, the invention should be construed to include other antibodies, as that term is defined elsewhere herein, to soluble Jagged, or portions thereof, or to proteins sharing at least about 65% homology with these proteins.

The invention encompasses polyclonal, monoclonal, synthetic antibodies, and the like. One skilled in the art would understand, based upon the disclosure provided herein, that the crucial feature of the antibody of the invention is that the antibody bind specifically with soluble Jagged. That is, the antibody of the invention recognizes soluble Jagged, or a fragment thereof, on Western blots, in immunostaining of cells, and immunoprecipitates soluble Jagged using standard methods well-known in the art.

One skilled in the art would appreciate, based upon the disclosure provided herein, that the antibodies can be used to localize the relevant protein in a cell and to study the role(s) of the antigen recognized thereby in cell processes. Moreover, the antibodies can be used to detect and or measure the amount of protein present in a biological sample using well-known methods such as, but not limited to, Western blotting and enzyme-linked immunosorbent assay (ELISA). Moreover, the antibodies can be used to immunoprecipitate and/or immuno-affinity purify their cognate antigen using methods well-known in the art.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.).

Monoclonal antibodies directed against full length or peptide fragments of a protein or peptide can be prepared using any well known monoclonal antibody preparation procedures, such as those described, for example, in Harlow et al., 1988, supra, and in Tuszynski et al. (1988, Blood, 72:109–115), and methods set forth elsewhere herein. Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

A nucleic acid encoding the monoclonal antibody obtained using the procedures described herein may be cloned and sequenced using technology which is available in the art, and is described, for example, in Wright et al. (1992, Critical Rev. Immunol. 12:125–168), and the references cited therein. Further, the antibody of the invention may be "humanized" using the technology described in Wright et al. (supra), and in the references cited therein, and in Gu et al. (1997, Thrombosis and Hematocyst 77:755–759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al., supra.

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al. (supra).

Processes such as those described above, have been developed for the production of human antibodies using M13 bacteriophage display (Burton et al., 1994, Adv. Immunol. 57:191–280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures presented herein describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J. Mol. Biol. 222:581–597). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837–839; de Kruif et al. 1995, J. Mol. Biol. 248:97–105).

Compositions

The invention includes a composition comprising an isolated purified soluble Jagged, or fragment thereof, and a composition comprising an isolated nucleic acid encoding soluble Jagged. The compositions can be used, for example, to assess the level of expression of soluble Jagged, to affect the level of soluble Jagged in a cell and/or in a mammal, as well as to affect angiogenesis, differentiation, or both, in a cell and/or in a mammal, to identify useful compounds, and the like.

The invention includes a composition comprising an isolated purified polypeptide comprising a soluble Jagged. Preferably, the composition comprises a pharmaceutically acceptable carrier. The composition can be administered to a mammal afflicted with a disease, disorder or condition associated with a reduced level of soluble Jagged compared with the level of soluble Jagged in an otherwise identical mammal not suffering from such disease, disorder or condition.

Additionally, a composition comprising an isolated purified polypeptide comprising a soluble Jagged, or an immunogenic portion thereof, can be administered to an animal to induce an immune response thereto. One skilled in the art would appreciate, based upon the disclosure provided herein, that the composition can be used to produce useful antibodies that specifically bind with soluble Jagged.

The invention further includes a composition comprising an isolated soluble Jagged, or a fragment thereof wherein the fragment comprises amino acid residues from about 1 to about 1067 (SEQ ID NO:18) (FIG. 13A) of the full-length Jagged-1 protein (SEQ ID NO:1) depicted in FIG. 8A.

Administering soluble Jagged is useful since previous studies demonstrate that soluble Jagged plays a crucial role in angiogenesis (see, e.g., studies demonstrating that soluble Jagged induces angiogenesis in a CAM assay). Thus, one skilled in the art would understand, based upon the disclosure provided herein, that administration of soluble Jagged is an important potential therapeutic for treatment of a disease, disorder or condition mediated by decreased soluble Jagged expression, function, or both.

The invention further includes administering soluble Jagged by administering a nucleic acid encoding soluble Jagged (e.g., a nucleic acid having at least about 20% homology with SEQ ID NO:17 which comprises from about nucleotide 1 to about nucleotide 3201 of SEQ ID NO:2). As more fully set forth elsewhere herein, one skilled in the art would appreciate, based upon the disclosure provided herein, that a protein can be administered to a cell and/or to a mammal, by administering a nucleic acid encoding the protein. Such methods of administering a protein of interest, i.e., a soluble Jagged or a fragment thereof, are encompassed in the present invention.

For administration of the above-mentioned compositions to a mammal, a polypeptide, or the nucleic acid encoding it, or both, can be suspended in any pharmaceutically acceptable carrier, for example, HEPES buffered saline at a pH of about 7.8. Other pharmaceutically acceptable carriers which are useful include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Pharmaceutical compositions that are useful in the methods of the invention may be administered, prepared, packaged, and/or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

The compositions of the invention may be administered via numerous routes, including, but not limited to, oral, rectal, vaginal, parenteral, topical, pulmonary, intranasal, buccal, or ophthalmic administration routes. The route(s) of administration will be readily apparent to the skilled artisan and will depend upon any number of factors including the type and severity of the disease being treated, the type and age of the veterinary or human patient being treated, and the like.

Pharmaceutical compositions that are useful in the methods of the invention may be administered systemically in oral solid formulations, ophthalmic, suppository, aerosol, topical or other similar formulations. In addition to the compound such as heparan sulfate, or a biological equivalent thereof, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer soluble Jagged, alone or in combination with a nucleic acid encoding the same.

The invention encompasses the preparation and use of pharmaceutical compositions comprising a compound useful for treatment of any disease, disorder or condition associated with altered expression of soluble Jagged in a mammal. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs. In addition, the administration of the compositions to birds is also contemplated.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulfate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxy propyl methyl cellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide a pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methyl cellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of a dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of an oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally, the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as 0.1% (w/w) to as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, comprise from about 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1–1.0% (w/w) solution or suspension of the active ingredient in an aqueous or oily liquid carrier. Such drops may further comprise buffering agents, salts, or one or more other of the additional ingredients described herein. Other ophthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Typically dosages of the compound of the invention which may be administered to an animal, preferably a human, range in amount from 1 microgram to about 100 grams per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 milligram to about 10 grams per kilogram of body weight of the animal. More preferably, the dosage will vary from about 10 milligrams to about 1 gram per kilogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

Methods

The present invention also includes a method of affecting angiogenesis in a system capable of angiogenesis. As more fully set forth elsewhere herein in discussing methods of using a Jagged protein or a functionally equivalent derivative or allelic or species variant thereof, a soluble Jagged protein can be used to affect angiogenesis due to the role of the Jagged-Notch signaling pathway in angiogenesis. That is, the data disclosed herein demonstrate that contacting certain cells with soluble Jagged mediates angiogenesis in "systems capable of angiogenesis," as exemplified by formation of tissue masses in nude mice, sprout formation by endothelial cells, cell migration, and angiogenesis detected in a CAM assay. One skilled in the art would appreciate, based upon the disclosure provided herein, that there are numerous systems capable of angiogenesis under the proper conditions where angiogenesis can be assessed such as those disclosed herein, as well as systems well-known in the art and those to be developed in the future, all of which are encompassed in the present invention.

More specifically, in one embodiment, transfected cells expressing soluble Jagged demonstrated altered growth in culture and/or formation of tissue masses in nude mice and/or angiogenic potential in CAM assay compared to a FGF-2 positive control. As stated previously elsewhere herein, one skilled in the art would appreciate, based upon the disclosure provided herein, that the ability of a soluble Jagged protein to affect angiogenesis can be measured not only by the aforementioned assays but by any similar assay now available or which is developed in the future to measure angiogenic potential.

Further, one skilled in the art would appreciate, based upon the instant disclosure, that angiogenesis can be affected not only by the addition of exogenous soluble Jagged protein, but can also be affected by the introduction of an exogenous nucleic acid encoding soluble Jagged into a cell where it is expressed, and/or by the introduction into a mammal of cells which express the protein which is encoded by a soluble Jagged nucleic acid. Thus, the method of the present invention is not limited to any particular manner in which the Jagged protein and/or soluble Jagged is provided to a cell or to a mammal; rather, the invention encompasses various methods whereby a Jagged protein, a soluble Jagged, and/or a portion thereof, is introduced to a cell or into a mammal.

As more fully set forth elsewhere herein, a soluble Jagged protein can be administered to a mammal via a variety of routes. Further, the dosage and amounts administered depend on numerous factors which are discussed more fully elsewhere herein in.

The amount of soluble Jagged administered, whether it is administered as protein or as nucleic acid or as a cell expressing soluble Jagged, is sufficient to elicit a Jagged/Notch signaling response. The pharmaceutical compositions useful for practicing the invention can be administered to deliver a dose of between about 1 nanogram per kilogram and about 100 milligrams per kilogram of soluble Jagged protein per patient body weight. Suitable amounts of the soluble Jagged protein for administration include doses which are high enough to have the desired effect without concomitant adverse effects. When the soluble Jagged is a protein or peptide, a preferred dosage range is from about 1 pg to about 100 mg of protein or peptide per kg of patient body weight.

When the soluble Jagged is administered in the form of DNA encoding the same contained within a recombinant virus vector, a dosage of between about $10^2$ and about $10^{11}$ plaque forming units of virus per kilogram of patient body weight can be used. When naked DNA encoding the soluble Jagged is to be administered as the pharmaceutical composition, a dosage of between about 1 pg to about 100 mg of DNA per kilogram of patient body weight can be used.

Further, when the soluble Jagged is administered in the form of a cell expressing a nucleic acid encoding the same, the dosage of cells per kilogram of patient body weight can be assessed depending on the amount of soluble Jagged protein expressed by the cells and the level desired as disclosed previously elsewhere herein.

When soluble Jagged is administered by administering a nucleic acid encoding the protein, the nucleic acid can be administered naked (e.g., substantially free of any other substance with which a nucleic acid is typically associated such as protein, and the like). Alternatively, the nucleic acid can be encapsulated or otherwise associated with another substance capable of facilitating the introduction of the nucleic acid into a cell. Such nucleic acid delivery techniques are described elsewhere herein and are well-known in the art and are described in, for example, Sambrook et al., supra, and Ausubel et al., supra.

An angiogenic effective amount, as that term is used and defined elsewhere herein, can be readily determined using any of the angiogenesis assays disclosed herein as well as methods well-known in the art. That is, the angiogenic effect of a soluble Jagged administered to a cell and/or to an organism or assay system, can be assessed by, for example, measuring the effect of soluble Jagged on expression of various genes (e.g., using differential display analyses such as SAGE analysis), migration of cells in culture, formation of chords by cells grown on plastic or on collagen matrices, assessing the level of repression of type I collagen expression, measuring the angiogenic potential using a CAM assay and/or measuring the in vivo growth of the cell using transplant studies in various murine models. However, the present invention is not limited to these assays to detect effects of soluble Jagged on angiogenesis; rather, similar assays which are now known or which are developed in the future may be used to determine the effect of soluble Jagged protein on angiogenesis.

The invention also includes a method of affecting differentiation of a cell. The method comprises contacting a cell with an effective amount of a substantially purified soluble Jagged protein. One skilled in the art would appreciate, based upon the disclosure provided herein, that contacting a cell with a soluble Jagged protein mediates signaling via the Jagged/Notch pathway such that cell differentiation, angiogenesis, and other cellular processes, are affected as demonstrated by the data disclosed herein.

One skilled in the art would further appreciate, based upon the disclosure provided herein, that a cell whose differentiation can be affected by contacting the cell with soluble Jagged should express a Jagged receptor, e.g., Notch, and comprise all necessary components of the Jagged/Notch signaling pathway such that Jagged/Notch interactions involved in differentiation can be affected by contacting the cell with soluble Jagged. Cells that express a Jagged receptor that can be used for such an assay include, but are not limited to, any mesodermal-derived cell, any endodermal-derived cell, any ectodermal-derived cell, and any neurodermal-derived cell, and the like. In addition to cells that naturally express an endogenous Jagged receptor, the present invention encompasses cells that have been manipulated such that they express a Jagged receptor and comprise the necessary Jagged/Notch signaling pathway so that the effect of soluble Jagged upon differentiation can be assessed in the cell.

A differentiation effective amount, as that term is defined elsewhere herein, of soluble Jagged protein can be readily determined by assessing the effect(s) of contacting a cell with soluble Jagged or a fragment thereof. Such methods include, but are not limited to, those disclosed herein which include measuring the effect of soluble Jagged on expression of various genes (e.g., using differential display analyses such as SAGE analysis) including repression of type I collagen expression, growth of cells on plastic or on collagen matrices, formation of chords and/or tubes by cells grown on plastic or on collagen matrices, measuring the angiogenic potential using a CAM assay and/or measuring the in vivo growth of the cell using transplant studies in various murine models. However, the present invention is not limited to these assays to detect effects of soluble Jagged on cell differentiation; rather, similar assays which are now known or which are developed in the future may be used to determine the effect of soluble Jagged protein on differentiation.

Further, the invention includes a method of identifying a compound capable of affecting differentiation in a cell. The method comprises contacting a soluble Jagged transfectant cell with a test compound and comparing the growth characteristics of the cell with the growth characteristics of an otherwise identical soluble Jagged transfectant cell not contacted with the compound. One skilled in the art would appreciate, based upon the disclosure provided herein, that comparing the growth characteristics of a soluble Jagged transfectant cell, which is/are an indicator of differentiation, allows the identification of a compound that affects cell differentiation.

By the term "growth characteristics," as the term is used herein, is meant any change in growth kinetics, size, morphology, and/or association with other cells exhibited by a cell transfected with nucleic acid encoding a soluble Jagged which is not exhibited by an identical cell which is not transfected or which is transfected with an empty, insert-less vector. As disclosed herein, such growth characteristics include, but are not limited to, the ability to form chord-like structures (shown in FIG. 10) when grown in vitro; the ability to form tissue masses when transplanted into nude mice (as shown in FIG. 12); and the ability to form angiogenic structures in CAM assays.

Further, the growth characteristics include the pattern of gene expression as assessed using, for example, a modified differential display method such as serial analysis of gene expression (SAGE) analysis as exemplified herein. This is because, as stated previously elsewhere herein, the pattern of gene expression is correlated to cell differentiation such that changes in the pattern are indicative of differentiation in the cell. Thus, the pattern of gene expression in the cell contacted with a test compound can be compared to the pattern in an otherwise identical cell not contacted with the compound and/or with the pattern in the cell prior to being contacted with the compound. The altered level of expression in certain genes can be assessed and used to detect differentiation in a cell since the data disclosed herein demonstrate that soluble Jagged-mediated differentiation causes the level of certain transcripts to decrease while causing the level of other transcripts to increase. Therefore, changes in the pattern of gene expression in a cell can be used to indicate differentiation in the cell mediated by soluble Jagged and the effect(s) of a test compound on such differentiation.

However, the present invention should not be construed to be limited to these or any other particular growth characteristics or assays to determine cell differentiation. Rather, any growth characteristic demonstrated by a cell transfected with a nucleic acid encoding a soluble Jagged which is not exhibited by an otherwise identical cell not transfected, or transfected with an empty vector, may be used in identifying a test compound capable of affecting cell differentiation. This is because, as will be appreciated by one skilled in the art based upon the disclosure provided herein, a growth characteristic exhibited by a soluble Jagged transfectant but not exhibited by an otherwise identical cell which is not transfected (or which is transfected by an empty, insert-less vector) is due, at least in part, by the altered Jagged/Notch signaling in the transfectant and the Jagged/Notch signaling pathway is known to be involved in cell differentiation, angiogenesis, and the like. Thus, a compound that affects a growth characteristic mediated by the Jagged/Notch signaling pathway affects cell differentiation since differentiation is also mediated by such pathway.

Similarly, the present invention includes a method of identifying a compound capable of affecting the binding of Jagged ligand to a Notch receptor. The method comprises contacting a soluble Jagged-transfected cell with a test compound and comparing the growth characteristics of the cell contacted with the compound with the growth characteristics of an otherwise identical cell not contacted with the compound. As discussed previously herein, a difference in the growth characteristic(s), including any change in the pattern of gene expression otherwise mediated by soluble Jagged, of the transfectant cell contacted with the compound compared with the growth characteristic(s) of the otherwise identical transfectant cell not contacted with the compound is an indication that the compound is capable of affecting the binding of Jagged ligand to a Notch receptor. This is because the growth characteristic(s) is the result of the altered Jagged/Notch signaling pathway present in the soluble Jagged transfectant cell which, if affected by a substance, indicates that the substance affects Jagged/Notch binding. Therefore, as will be appreciated by one skilled in the art based upon the disclosure provided herein, a change in a growth characteristic associated with or mediated by the altered Jagged/Notch signaling pathway upon contact with a test compound is an indication of the ability of the test compound to affect such pathway, and, therefore, to affect Jagged/Notch binding.

The invention also includes a method of identifying a compound capable of affecting angiogenesis. The method comprises contacting a soluble Jagged transfectant cell with a test compound and comparing the growth characteristics of the cell contacted with the compound with the growth characteristics of an otherwise identical cell not contacted with the compound. As discussed previously herein, a difference in the growth characteristic(s), including any change in the pattern of gene expression otherwise mediated by soluble Jagged, of the transfectant cell contacted with the compound compared with the growth characteristic(s) of the otherwise identical transfectant cell not contacted with the compound is an indication that the compound is capable of affecting angiogenesis. This is because the growth characteristic(s) present in the soluble Jagged transfectant cell, is the result of the altered Jagged/Notch signaling pathway and the Jagged/Notch signaling pathway mediates angiogenesis. Thus, the growth characteristic(s) in the transfected cell mediated by soluble Jagged are involved in angiogenesis such that if the growth characteristic(s) is/are affected by a substance, such response indicates that the substance affects angiogenesis.

Therefore, as will be appreciated by one skilled in the art based upon the disclosure provided herein, a change in a growth characteristic associated with or mediated by the altered Jagged/Notch signaling pathway upon contact with a test compound is an indication of the ability of the test compound to affect such pathway, and, therefore, to affect angiogenesis mediated by Jagged/Notch signaling.

The present invention further provides methods of regulating gene expression in a cell. For example, a cell can be altered such that it contains a DNA sequence operably linked to a RE. Additionally, the cell can be altered to control the expression of Jagged permitting one skilled in the art to generate a cell which expresses a given sequence in response to a particular agent.

The subjects treated in accordance with the present invention include any vertebrate organism; more preferably any mammal; most preferably a human. The only limiting factor is that the organism endogenously produces Notch and/or the toporythmic genes which modulate binding to Notch.

By providing methods of affecting angiogenesis by modulating the Notch-Jagged signal pathway, the present invention provides methods and compositions which affect a number of physiologic and pathologic conditions, including placental development, wound healing, rheumatoid arthritis, diabetic retinopathy and solid tumor growth and metastasis and motor neuron disorders. The referenced wound healing includes healing of any injury or lesion in the skin, tissue, vasculature, or nervous system of the subject, and includes cell migration and differentiation of cells comprising the mesoderm, endoderm, ectoderm and/or neuroderm. The wound or injury can be the result of surgery, trauma, and/or disease or condition. Such disease and/or conditions include ischemic lesions resulting from a lack of oxygen to the cell or tissue, e.g., cerebral or cardiac infarction or ischemia, malignant lesions, infectious lesions, e.g., abscess, degenerative lesions, lesions related to nutritional disorders, neurological lesions associated with systemic diseases, e.g., diabetic neuropathy and retinopathy, systemic lupus erythematosus, carcinoma or sarcoidosis, and lesions caused by toxins, e.g., alcohol, lead, etc. Motor neuron disorders may include, e.g., amylotrophic lateral sclerosis, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and hereditary Motorsensory Neuropathy (Charcot-Marie-Tooth disease).

The invention also includes a method of inhibiting expression of type I collagen in a cell. The method comprises administering an expression inhibiting amount of soluble Jagged to a cell, thereby inhibiting expression of type I collagen. One skilled in the art would understand that various type I collagens (e.g., pro-α-1(I) collagen, pro-α-2 (I) collagen, and the like) are encompassed by the invention which is not limited to any particular type I collagen.

One skilled in the art would also appreciate, based upon the disclosure provided herein, that soluble Jagged-1 can be administered to a cell via a variety of methods including, but not limited to, administering a nucleic acid encoding soluble Jagged, a vector encoding soluble Jagged, and an isolated soluble Jagged. The important feature is not how the soluble Jagged is delivered to the cell but, rather, that soluble Jagged be administered to the cell in sufficient quantity to affect Jagged/Notch interactions involved in Jagged/Notch signaling so as to repress expression of a type I collagen gene.

The level of soluble Jagged required to inhibit type I collagen expression can be readily determined using the assays disclosed herein or other assays well-known in the art and/or based from the assays disclosed elsewhere herein. For example, such assays include, but are not limited to, assessing the level of type I collage gene expression using SAGE analysis and/or other nucleic-acid based assays (e.g., Southern blotting, Northern blotting, slot-blots, PCR-based methods, and the like). In addition, type I collagen expression can be determined by assessing the production of a specific type I collagen domain, e.g., the amino-terminal peptide portion of pro-α-1(I), and the like, using antibody-based detection methods, which are well-known in the art and/or disclosed elsewhere herein (e.g., immunoblotting, ELISA, immunoprecipitation, and such).

Methods of inhibiting type I collagen expression are of crucial importance in the development of therapeutics for a plethora of fibrotic diseases associated with production of type I collagen for which there is currently no effective treatment.

Kits

The invention includes various kits which comprise a compound, such as an isolated nucleic acid encoding soluble Jagged in a sense or in an antisense orientation, or an isolated soluble Jagged polypeptide, or the antibodies of the invention, and instructional materials which describe use of the compound to perform the methods of the invention. Although exemplary kits are described below, the contents of other useful kits will be apparent to the skilled artisan in light of the present disclosure. Each of these kits is included within the invention.

In one aspect, the invention includes a kit for affecting angiogenesis in a mammal. The kit is used pursuant to the methods disclosed in the invention. Briefly, the kit may be used to introduce an isolated soluble Jagged polypeptide, an isolated nucleic acid encoding soluble Jagged, and/or a cell expressing soluble Jagged into a mammal in order to increase the level of soluble Jagged in the mammal. This affects angiogenesis in that, as disclosed previously elsewhere herein, soluble Jagged affects the Jagged/Notch signaling pathway which, in turn, affects angiogenesis. Thus, administering soluble Jagged to a mammal, either by administering soluble Jagged protein, a nucleic acid encoding soluble Jagged, and/or a cell expressing soluble Jagged, affects angiogenesis in the mammal.

Moreover, the kit comprises an instructional material for the use of the kit. These instructions simply embody the disclosure provided herein.

The invention further includes a kit for affecting differentiation in a cell. The kit comprises an effective amount of an isolated soluble Jagged polypeptide, an applicator, and an instructional material for the use of the kit. One skilled in the art would appreciate, based upon the disclosure provided herein, that the kit can be used to administer soluble Jagged to a cell, either by administering to such cell at least one of the following: isolated soluble Jagged protein, and/or a nucleic acid encoding soluble Jagged that is expressed in the cell. Soluble Jagged, in turn, mediates differentiation in the cell via the Jagged/Notch signaling pathway. Thus, by affecting the Jagged/Notch signaling pathway, soluble Jagged affects differentiation in a cell which is either contacted with soluble Jagged, or which expresses the protein.

Moreover, the kit comprises an instructional material for the use of the kit. These instructions simply embody the disclosure provided herein.

The invention includes a kit for inhibiting expression of type I collagen in a cell. The kit comprises an expression inhibiting amount of soluble Jagged, an applicator, and an instructional material for the use of said kit.

One skilled in the art would appreciate, based upon the disclosure provided herein, that the inhibiting amount of soluble Jagged can be readily determined using the assays disclosed herein to assess reduction of type I collagen expression (e.g., SAGE analysis, immunoblotting). Further, standard assays well-known in the art, and discussed elsewhere herein, can also be used to assess the level of soluble Jagged to be administered and the level of type I collagen expressed, correlated with the administration of soluble Jagged. That is, a wide plethora of assays can be used to assess the level of type I collagen nucleic acid and/or protein produced in a cell compared with an otherwise identical cell to which soluble Jagged is not administered. Thus, the expression inhibiting amount of soluble Jagged can be easily determined based upon the disclosure provided herein.

Additionally, the invention is not limited to any particular type I collagen; rather, the invention includes various type I collagens, e.g., pro-α-1(I) collagen, pro-α-2(I) collagen, and the like.

Moreover, the kit comprises an instructional material for the use of the kit. These instructions simply embody the disclosure provided herein.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

All essential publications mentioned herein are hereby incorporated by reference.

EXAMPLES

In the following examples and protocols, restriction enzymes, ligase, labels, and all commercially available reagents were utilized in accordance with the manufacturer's recommendations. The cell and molecular methods utilized in this application are established in the art and will not be described in detail. However, standard methods and techniques for cloning, isolation, purification, labeling, and the like, as well as the preparation of standard reagents were performed essentially in accordance with Sambrook et al. (1989, Molecular Cloning, Cold Spring Harbor Laboratory Press, Cold Spring Harbor, N.Y.), and the revised third edition thereof, Ausubel et al.(1997, Current Protocols in Molecular Biology, John Wiley & Sons, New York), or as set forth in the literature references cited and incorporated herein. Methodologic details may be readily derived from the cited publications.

Example 1

Isolation of Human Endothelial Cell cDNA Induced by Exposure to Fibrin

Endothelial cells plated on fibrin organize into three dimensional tubular structures in vitro (Olander et al., 1985, J. Cell. Physiol. 125:1–9), and this organizational behavior requires transcriptional responses (Zimrin et al., 1995). Using a modification of the differential display, cDNA clones were obtained that were differentially expressed by HUVECs in response to fibrin. Briefly, total RNA was isolated from HUVEC plated on fibrin in the presence of crude FGF-1 at 0, 2, 5 and 24 hours and subjected to the modified differential mRNA display. One of the clones (D9) isolated from HUVEC populations exposed to fibrin, which was found to have increased at the 2 hour time-point, was cloned and sequenced. A search of the GenBank database in 1994 demonstrated that the D9 sequence was novel.

The D9 clone was used as a probe to screen a lambda cDNA library prepared from mRNA obtained from HUVECs exposed to fibrin gels for 1, 3 and 5 hours. Ten isolates were recovered that contained the D9 sequence, two of which appeared, by restriction enzyme analysis, to be spliced variants of the remaining eight. Sequence analysis of the clones revealed that they overlapped to form a contiguous sequence of 5454 base pairs (bp) in length, set forth as SEQ ID NO:2.

Example 2

Figure 2:
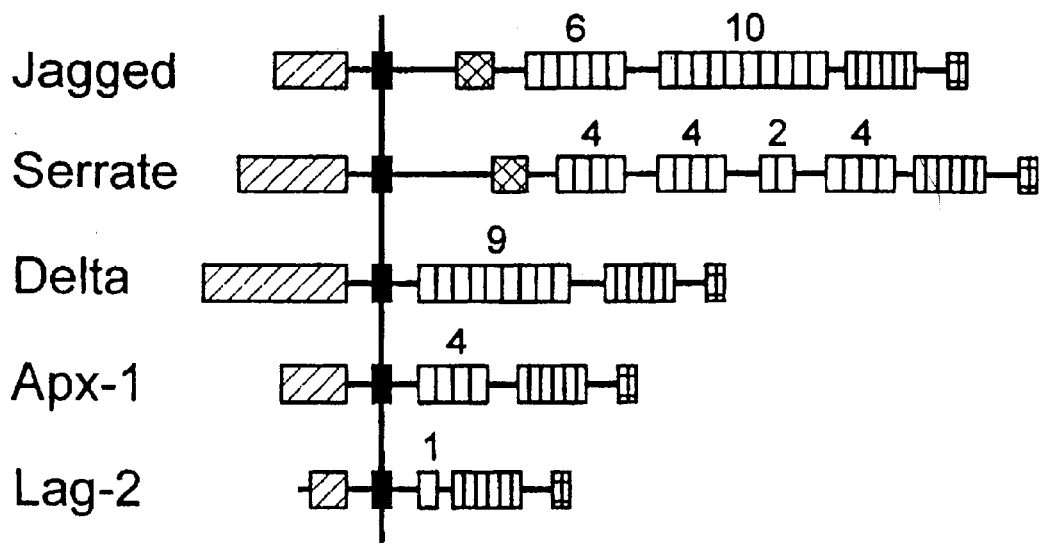
FIG. 2 is a diagram illustrating the domain structure of the Notch ligand family. (Numbers refer to the number of EGF repeats in the extracellular domain.) As indicated in this chart, although the intracellular domain of the Jagged gene contains a sequence with no known homology to intracellular regions of other transmembrane structures, the extracellular region of the gene contains a cys-rich region, 16 epidermal growth factor (EGF) repeats, and a Delta-Serrate-Lag (DSL) domain, typical of comparable regions found in other genes including the Drosophila ligands, Serrate and Delta, and the *C. elegans* genes, Apx-1 and Lag-2.
Figure 3:
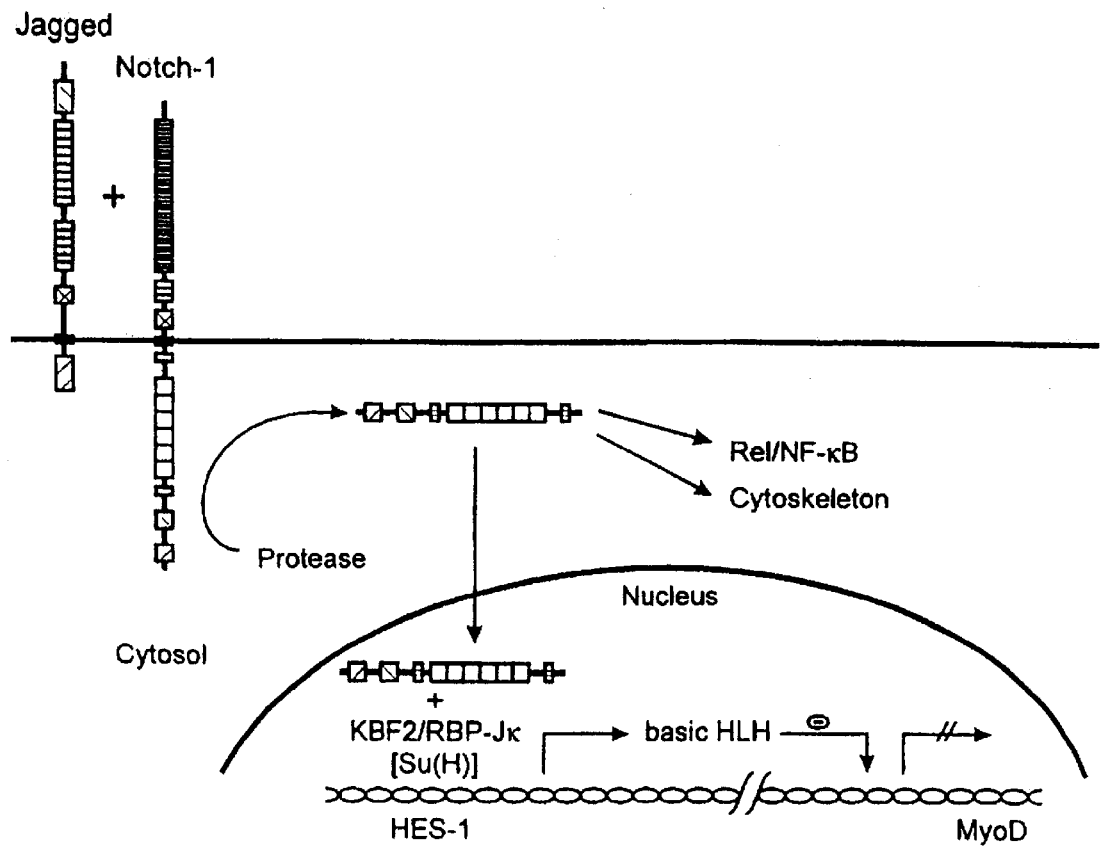
FIG. 3 is a diagram illustrating the Notch signaling pathway. The components of the Notch signaling pathway are illustrated, using the myoblast as an example. The Notch signaling pathway, when activated by Jagged in the endothelial cell, involves cleavage of the intracellular domain by a protease, nuclear trafficking of the Notch fragment and the interaction of this fragment with the $KBF_2$/RBP-Jk transcription factor, a homolog of the Drosophila Suppressor of Hairless (Su(H)) gene, which is a basic helix-loop-helix transcription factor involved in Notch signaling.
Figure 4:
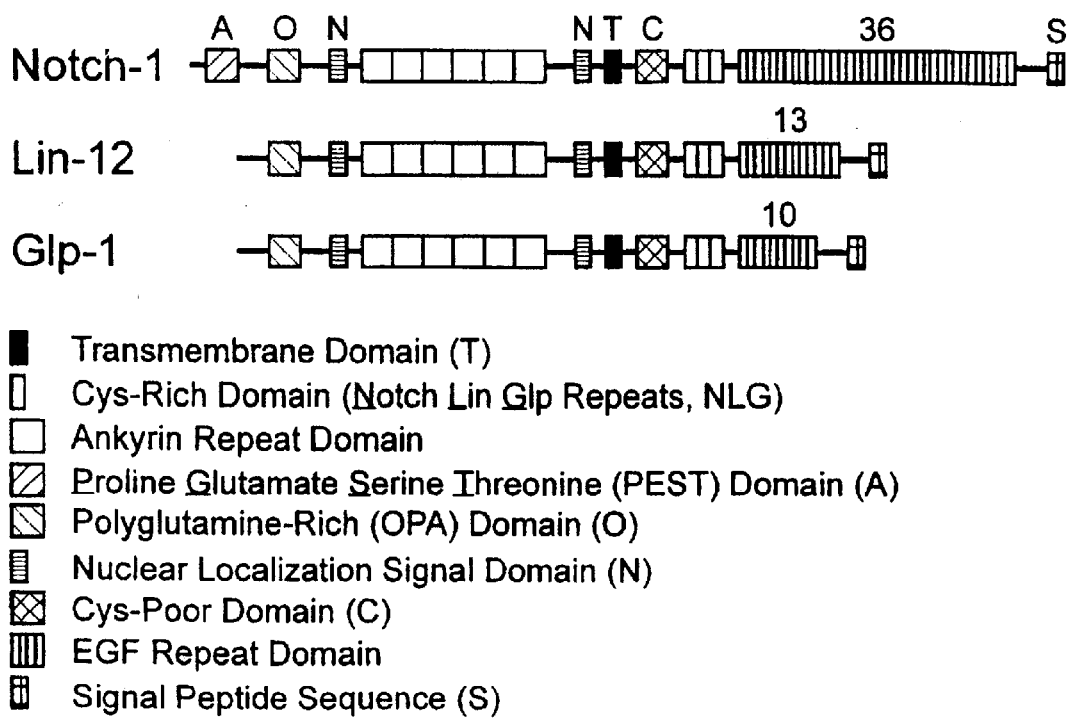
FIG. 4 is a diagram illustrating the domain structure of the Notch receptor family. (Numbers refer to the number of EGF repeats in the extracellular domain.) As indicated in this chart, in addition to the 36 EGF repeats within the extracellular domain of Notch 1, there is a cys-rich domain composed of three Notch-Lin-Glp (NLG) repeats, followed by a cys-poor region between the transmembrane and NLG domain. The intracellular domain of Notch 1 contains six ankyrin/Cdc10 repeats positioned between two nuclear localization sequences (NLS). In the carboxy-terminal direction from this region is a polyglutamine-rich domain (OPA) and a pro-glu-ser-thr (PEST) domain (SEQ ID NO:33): Comparable structures are shown for Lin-12 and Glp-1.

Analysis of the Sequence of HUVEC Clone D9 Demonstrates Homology With the Rat Jagged Gene A second search of the Genebank database in 1995 revealed that the D9 clone was very homologous to the cDNA sequence coding for the rat Jagged gene (Lindsell et al., 1995, Cell 80:909–917), a ligand for the Notch receptor. Computer analysis revealed an 87% identity at the nucleotide level and a 95% identity at the amino acid level. The Jagged protein (GenBank Acc. No. U77720, FIG. 8A [SEQ ID NO:1]) contains a putative signal sequence (from about amino acid residue 1 to about amino acid residue 21), a DSL domain which describes a consensus region present in other Notch ligands (Delta, Serrate, Lag-2 and Apx-1) (from about amino acid residue 185 to about amino acid residue 229), an EGF-like repeat domain containing sixteen EGF repeats (from about amino acid residue 234 to about amino acid residue 862), a cys-rich domain (from about amino acid residue 863 to about amino acid residue 1002), a transmembrane domain (from about amino acid residue 1068 to about amino acid residue 1093), and a cytosol domain (from about amino acid residue 1094 to about amino acid residue 1218) (see FIG. 8A). This structure is schematically represented in FIG. 2. Thus, it was determined that clone D9 represents the human homolog of the rat Jagged cDNA.

Two additional Jagged clones were also obtained each containing identical deletions. The first was 89 bp in length, and was located in the middle of the cys-rich region. The second clone occurred 366 bp downstream from the first clone, and was approximately 1307 bp in length. The first deletion predicts a frame-shift in the translation product, resulting in a unique 15 amino acid sequence followed by a premature termination of the protein, effectively deleting the transmembrane and cytosol domains from the Jagged structure. Nucleic acids encoding truncated Jagged-1 protein (termed "soluble Jagged", "sol-jag", or "sJ-1," which are used interchangeably herein) were used to produce transfected NIH 3T3 cells expressing soluble Jagged which cells demonstrated altered angiogenic potential in both in vivo transplantation studies using nude mice and in traditional CAM assays (see Examples 8 and 9, infra).

Example 3

Human Endothelial Cell Populations Express Both Jagged and Notch Transcripts

To ascertain that both the human Jagged gene and its putative receptor, Notch, were expressed in the HUVEC population, oligonucleotide primers were designed based upon the published sequence for the human Tan-1 transcript (Notch-1) and the human Notch group protein transcript (Notch-2), as well as for the human Jagged transcript.

Total RNA was obtained using standard protocols. The differential display was performed as previously described by Folkman and Haudenschild (1980, Nature 288:551–556).

Briefly, 1 µg of total RNA was reverse transcribed with 200U M-MLV reverse transcriptase (BRL) in the presence of 2 µM of the 3' primer (5'-GCGCAAGCT$_{12}$CG-3' [SEQ ID NO:3]) and 100 µM dNTP for 70 minutes at 37° C. The cDNA was amplified in the presence of ($^{32}$p) dATP (Amersham) using the same 3' primer and a 5' primer with the sequence 5'-GAGACCGTGAAGATACTT-3' (SEQ ID NO:4) and the following parameters: 94° C. 45 seconds, 41° C. 1 minute, 72° C. 1 minute for 4 cycles, followed by 94° C. 45 seconds, 60 ° C. 1 minute, 72° C. 1 minute for 18 cycles. The resulting cDNA species were separated using polyacrylamide gel electrophoresis, the gel was dried and exposed to radiographic film, and the band of interest was cut out of the gel and eluted.

The cDNA was amplified using the same primers and cloned into a TA vector (Invitrogen, Carlsbad, Calif.). The clone was used to screen a cDNA library made in the ZAP Express vector (Stratagene, La Jolla, Calif.) using RNA isolated from HUVEC plated on fibrin in the presence of crude FGF-1 for 1, 3, 5, 8 and 24 hours to analyze the steady-state levels of the transcripts for Jagged, Notch 1, Notch 2, and GAPDH. See Garfinkel et al., 1996, J. Cell Biol. 134:783–791. The overlapping cDNA clones obtained were sequenced using an ABI DNA synthesizer and assembled with the DNASTAR program. RT-PCR analysis was performed as described using the following primers:

jagged sense 5'-CCGACTGCAGAATAAACATC-3' (SEQ ID NO:5);

jagged antisense 5'-TTGGATCTGGTTCAGCTGCT-3' (SEQ ID NO:6);

notch 1 sense 5'-TTCAGTGACGGCCACTGTGA-3' (SEQ ID NO:7);

notch 1 antisense 5'-CACGTACATGAAGTGCAGCT-3' (SEQ ID NO:8);

notch 2 sense 5'-TGAGTAGGCTCCATCCAGTC-3' (SEQ ID NO:9);

notch 2 antisense 5'-TGGTGTCAGGTAGGGATGCT-3' (SEQ ID NO:10);

GAPDH sense 5'-CCACCCATGGCAAATT CCATGGCA-3' (SEQ ID NO:11);

GAPDH antisense 5'-TCTAGACGGCAGGTCA GGTCCACC-3' (SEQ ID NO:12).

As shown in FIG. 5, the steady state levels of the Notch-1 and Notch-2 transcripts were not altered in HUVEC populations exposed to fibrin. In contrast, however, the HUVEC Jagged transcript was induced after three hours exposure to fibrin after which time the steady state levels of the Jagged transcript decreased (FIG. 5).

Example 4

The Role of Jagged as a Mediator of Microvascular Sprout Formation In Vitro

Because (i) Delta/Serrate signaling through Notch is involved in the determination of cell fate in invertebrates (Fortini and Artavanis-Tsakonas, 1993, Cell 75:1245–1247), (ii) Jagged signaling through Notch attenuates the terminal differentiation of myoblasts to myotubes in vitro (Lindsell et al., 1995, Cell 80:909–917), (iii) the endothelial cell presents a non-terminal differentiated phenotype in vitro (FIG. 1), and (iv) the Jagged transcript was identified as an endothelial cell differentiation-induced gene, it was important to determine whether Jagged-Notch signaling in the endothelial cell was involved in the early phase of the differentiation pathway. It is well known that endothelial cell sprout formation is an early event in the microvasculature during angiogenesis (Montesano and Orci, 1985, Cell 42:469–477); and endothelial cell sprout formation assays are described in the art (Montesano et al., 1986, Proc. Natl. Acad. Sci. USA 83:7297–7301). However, to assess the role of Jagged-Notch signaling in this system, an antisense (γ) oligonucleotide was needed, based on the Jagged sequence to repress the translation of the Jagged transcript.

The γ-Jagged oligomer contained the Kozak sequence, the ATG translation start site and extended three codons into the open-reading frane. Similar γ-oligomers have proven useful in a wide variety of cellular systems to repress the translation of specific transcripts, including the human endothelial cell (Maier et al., 1990, J. Biol. Chem. 265:10805–10808; Garfinkel et al., 1992, J. Biol. Chem. 267:24375–24378). The controls for the γ-Jaggged oligomer included the sense counterpart, a 3'-antisense oligomer and a mutated 5' antisense oligomer.

Although the complete DNA sequence of the bovine Jagged transcript had not yet been fully defined, a high degree of homology at the 5' end was predicted between the bovine and the human Jagged nucleotide sequence, in view of the fact that the human and rat Jagged polypeptides are 95% identical.

Bovine microvascular endothelial cells (BMEC) were plated onto a collagen gel, grown to confluence in the presence or absence of varied concentrations of the γ-Jaggged oligomer. FGF-2 (10 ng/ml) was added at confluence (Montesano et al., 1986, Proc. Natl. Acad. Sci. USA 83:7297–7301), and the length of microvessels (sprouts formed as a result of cellular invasion into the collagen gel) was measured (Pepper et al., 1992, Biochem. Biophys. Res. Comm. 189:824–831). As shown in FIG. 6, exposure to the antisense γ-Jaggged oligomer (JAS; SEQ ID NO:29) resulted in an increase in BMEC sprout length in a concentration dependent manner above the level achieved by FGF-2. In contrast, the three control oligomers, a Jagged sense oligonucleotide (JS; SEQ ID NO:30), a 3' antisense Jagged oligomer (3' AS; SEQ ID NO:31), and a mutated 5' antisense Jagged oligomer (MUT5' AS; SEQ ID NO:32) did not affect the ability of FGF-2 (bFGF) to induce sprout formation in this assay (FIG. 6).

Prior to this experiment, with the possible exception of vascular endothelial cell growth factor (VEGF), no other growth factor/cytokine signal has been disclosed as able to potentiate the ability of FGF to modify BMEC sprout length. This result would not have been previously anticipated since the Jagged gene had been previously identified as a HUVEC-derived differentiation-induced transcript.

Example 5

The Disparate Effect of the Antisense (γ)-Jagged Oligomer on Small and Large Vessel Endothelial Cell Migration Based upon the surprising effect of the γ-Jaggged oligomers on the potentiation of FGF-2-induced BMBC sprout formation (Example 4), a simple assay was designed to assess the influence of the γ-Jaggged oligomer on BMEC migration, specifically to confirm that interrupting the Jagged-Notch signaling pathway would attenuate the ability of FGF to increase sprout length. Utilizing essentially the system of Sato and Rifkin (1988, supra), bovine microvascular endothelial cells (BMEC) were plated on a fibronectin matrix, and grown to confluence in the absence and presence of varied amounts of the γ-Jaggged oligomer.

Briefly, 4×10⁵ BMEC and BAEC were grown to confluence in serum-containing media containing 0, 1.25, 2.5, 5 and 6.25 μM Jagged antisense oligonucleotide. The monolayers were wounded by scraping them with a razor blade and cellular debris was removed by washing the plates twice with phosphate buffered saline. The cells were incubated for a further 22 hours at 37 ° C. to confluence, then fixed in 25% acetic acid, 75% methanol and stained with hematoxylin (Sigma Chemical Co., St. Louis, Mo.). The number of cells migrating from the wound origin were counted to determine the ability of the BMEC population to migrate into the denuded area. The count was made using a light microscope with a grid at 100×magnification. The data represent a mean of multiple experiments done in duplicate, with five microscopic fields counted for each point.

Figure 7A:
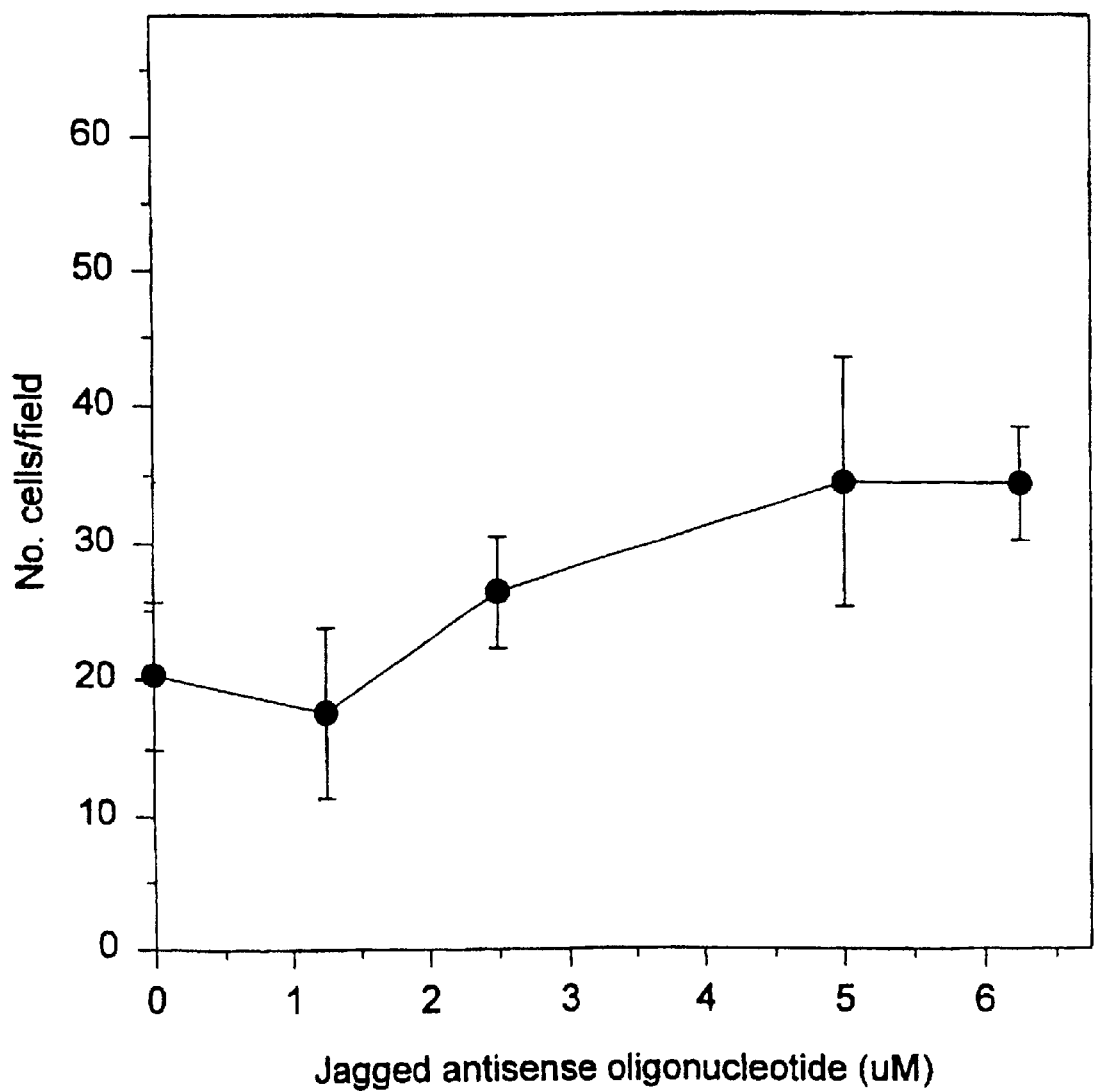
FIG. 7A is a graph depicting the effect of the antisense Jagged oligonucleotide on bovine microvascular endothelial cells (BMEC).
Figure 7B:
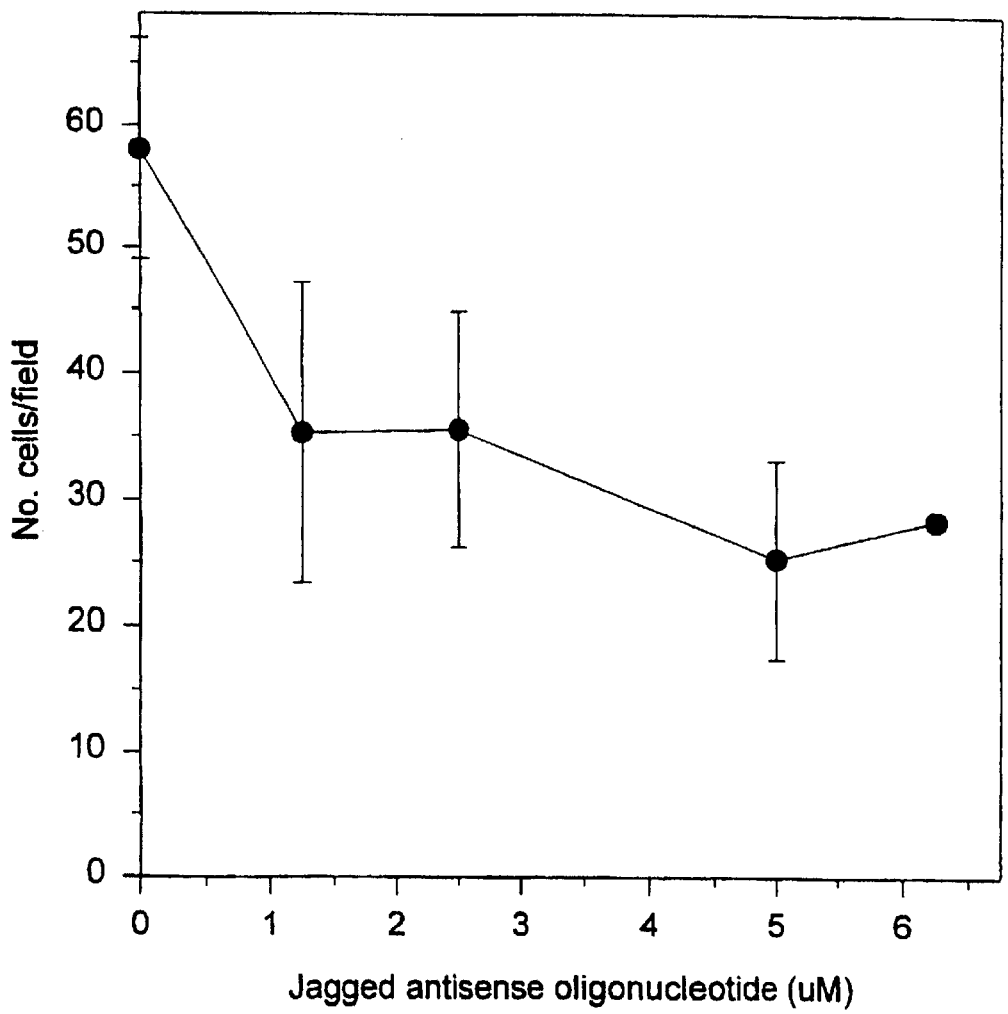
FIG. 7B is a graph depicting the effect of the antisense Jagged oligonucleotide on bovine aorta endothelial cells (BAEC).

As shown in FIG. 7A, the presence of the γ-Jaggged oligomer resulted in an increase in the number of cells migrating into the denuded area with an approximate 80% increase mediated by 5 μM γ-Jaggged oligomer. These data (FIG. 7A) agree with the BMEC data obtained from the sprout assay in which 2 μM γ-Jaggged oligomer yielded an approximate 100% increase in BMEC sprout length (FIG. 6). Thus, it was shown that an interruption in the Jagged-Notch signaling pathway resulted in an increase in BMEC migration, a major immediate-early component of sprout formation in vitro.

Consequently, an apparent discrepancy was noted between the results of the experiments showing (i) the isolation of the Jagged transcript from a HUVEC population preparing to migrate into a fibrin gel, and (ii) the enhancement of the BMEC by the presumed interruption of the Jagged signal. Noting that the HUVEC are obtained from a macro-vessel, and BMEC are from micro-vessels, the distinction was apparently directly related to the nature of the source of the endothelial cells.

To ascertain that the difference was based upon the type of the endothelial cell (macro- versus micro-vasculature), and not due to variations in the extracellular matrix or the function of growth factors/cytokines in the particular system, an experiment was designed in which the endothelial cells were obtained from the same species, but exclusively from a macrovascular source—bovine aorta endothelial cells (BAEC). BAEC were introduced onto a fibronectin matrix, grown to confluence in the absence and presence of various amounts of the γ-Jaggged oligomer, and their migration assessed in a manner identical to that used to assess BMEC migration. As shown in FIG. 7B, there was a concentration-dependent decrease in the migration of the BAEC population in response to the -Jagged oligomer with an approximate 50% reduction in BAEC migration at 5 μM γ-Jaggged oligomer.

When viewed together, these results indicated Jagged-Notch signaling as an anti-migratory event in the endothelium comprising the microvasculature, but as apromigratory event in the endothelium of large vessels. These experiments demonstrated for the first time that there apparently exists a major phenotype difference between small and large vessel endothelial cells in response to a ligand-receptor signaling pathway in the endothelial cell which is modulated during the migratory phase of angiogenesis.

Example 6

Further Characterization of the Disparate Effects Mediated by Jagged-induced Signaling in Vitro Using Human Endothelial Cells To better understand the mechanism utilized by human endothelial cells to regulate angiogenesis in man, it is important to study the effect of the γ-Jaggged oligomer on cell migration using human microvascular endothelial cells and human endothelial cells from large vessels. Although it would be preferable to obtain stable human endothelial cell γ-Jaggged transfectants/transductants using conventional gene transfer methods, none have proven useful with regard to human diploid endothelial cells in vitro. Therefore, the γ-Jaggged oligomer strategy is employed as a means to modify the translational efficiency of the human Jagged transcript.

Initially, however, two methods are used to confirm that the γ-Jaggged oligomer is able to reduce the efficiency of Jagged translation. Each utilizes rabbit anti-Jagged antibodies being prepared against individual synthetic peptides derived from the extracellular DSL domain, the extracellular cys-poor domain ($NH_2$-terminal to the transmembrane domain) and the intracellular (i.e., cytoplasmic) domain of the predicted Jagged protein sequence. Immunologic methods parallel those previously used for the production and purification of antibodies against synthetic peptides derived from sequence analysis of the FGF-1 receptor (Prudovsky et al., 1994, J. Biol. Chem. 269:31720–31724), cortactin (Zhan et al., 1994) and FGF-1 (Imamura et al., 1990, Science 249:1567–1570), and translation products are used. Synthetic peptides are prepared as multiple antigen peptides (MAP) using fmoc MAP resins from Applied Biosystems. Likewise, Notch-1 antibodies are also prepared using sequence from the extracellular LNG domain and intracellular ankyrin repeat domain for MAP synthesis.

The first method utilizes hybrid selection, using an immobilized Jagged oligomer to capture the Jagged transcript from HUVEC populations, followed by ($^{35}$S)-met/cys translation of the Jagged transcript in the rabbit reticulocyte system in the absence and presence of varied amounts of the γ-Jaggged oligomer. Immunoprecipitation of the Jagged protein followed by SDS-PAGE autoradiography establishes the ability of the γ-Jaggged oligomer to repress Jagged translation in vitro.

The second method utilizes HUVEC populations metabolically labeled with ($^{35}$S)-met/cys for Jagged immunoprecipitation from cells exposed to fibrin for 0, 1, 2 and 3 hours. Immunoprecipitation of the Jagged protein from the fibrin-induced HUVEC population followed by SDS-PAGE autoradiography permits a comparative assessment of whether pretreatment of the cells with the γ-Jaggged oligomer represses the level of the Jagged protein as a cell-associated polypeptide. The success of these strategies is based upon the fact that the Jagged protein sequence is rich in cys residues, and as a result is metabolically labeled to a high specific activity. Likewise, an accurate molecular weight is assigned to the Jagged protein since competition with synthetic peptide, pre-immune serum, as well as denatured γ-Jaggged antiserum, are used as controls to define the specificity of band assignment. Since the predicted Jagged translation product contains about 1054 amino acids, the molecular weight is in the 135 to 145 kDa range.

The disparate migratory behavior of the BMEC and BAEC populations is confirmed using stable γ-Jaggged transfectants. Since bovine cells are more amenable than HUVEC populations to gene transfer methods, the pMEX-neo vector (Martin-Zanca et al., 1989, Mol. Cell. Biol. 9:24–33) is used to select for stable BMEC and BAEC γ-Jaggged transfectants as previously described (Zhan et al., 1992). Stable clones are obtained using G418 resistance to quantify the migratory potential of these cells relative to insert-less vector control transfectants. The wound-induced migration assay (Example 6; FIG. 7A and 7B) is useful to demonstrate that the serum-induced migration potential of the BMEC γ-Jaggged transfectants is increased, and the serum-induced migration potential of the BAEC γ-Jaggged transfectants is decreased.

The analysis of the effect of the novel protein on human endothelial cells effectively employs the HUVEC population as a model, in comparison with HU artery (A) EC and human cells obtained from other anatomic sites, including, e.g., human adipose-derived microvascular endothelial cells (HMEC), human dermis-derived capillary endothelial cells (HCEC) and human saphenous vein (HSVEC) and artery (HSAEC), available from commercial and academic sources. The addition of the γ-Jaggged oligomer to these populations of human endothelial cells will be similar to that described in the protocols involving bovine endothelial cell populations. Thus, the ability of they-Jagged oligomer to modulate sprout formation of human capillary, artery and vein endothelial cells is assessed using the collagen invasion assay described in FIG. 6, and the migration wound assay described in FIG. 7 supplemented with a Boyden chamber chemotaxis assay as previously described (Terranova et al., 1985, J. Cell Biol. 101:2330–2334). The resulting data, similar to those obtained with the bovine endothelial cell populations, confirms the above-described conclusion (Examples 4 and 5) that reduction in the translational efficiency of the Jagged transcript (i) increases human microvascular endothelial cell sprout formation and migratory/chemotactic potential and (ii) reduces these activities in the human endothelial cell populations derived from arteries and veins.

Use of these transfectants permits a more rigorous quantification of the disparate modulation of migratory potential between small and large vessel endothelial cells using the conventional Boyden chamber assay previously used to establish the chemotactic activity of FGF-1 (Terranova et al., 1985, J. Cell Biol. 101:2330–2334). In addition, this approach also confirms the assessment of the ability of the BAEC γ-Jagged and insert-less vector control transfectants to respond to the FGF prototypes as inducers of sprout formation in vitro (FIG. 6). Lastly, this strategy permits an assessment of the migratory responsiveness of additional bovine endothelial cells obtained from alternative anatomic sites, including the portal vein, saphenous artery and vein, and adipose-derived microvascular endothelial cells. The ability of these cells to induce steady-state levels of Jagged and Notch receptor transcripts in response to fibrin is also evaluated by RT-PCR analysis as in Example 3 (FIG. 5).

A nuclear run-on analysis of BMEC and BAEC populations, as well as a kinetic analysis of the presence of the Jagged transcript in actinomycin D- and cycloheximide-treated cells in response to fibrin, is employed to determine whether the induction of the Jagged transcript is due to a transcriptional regulatory event and whether Jagged transcript stability is involved in the fibrin response. This analysis is analogous to a previous study on the post-transcriptional regulation of IL-1α in HUVEC populations by Garfinkel et al. (1994, Proc. Natl. Acad. Sci. USA 91:1559–1563). Nuclear run-on analysis is performed by incubating nuclei obtained from either BMEC or BAEC populations exposed to fibrin for 0, 1, 3 and 6 hours with 100 μCi of ($^-$P)-UTP for 30 minutes. This is followed by the isolation of nascent RNA transcripts, and slot blot analysis using 5 μg of the linearized, denatured and immobilized Jagged cDNA and hybridization at high stringency with the labeled RNA. Glyceraldehyde-3-phosphate dehydrogenase (GAPDH) is used as a positive control, and densitometric values are normalized to the GAPDH signal. Although the level of the Jagged transcript may be difficult to predict, a Jagged signal should be visible. Testing the γ-Jaggged oligomer at varied levels permits a determination of the ability, if any, of the γ-Jaggged oligomer to access the transcriptional machinery in this system.

To determine in those endothelial cell populations that are induced by the γ-Jagged oligomer to decrease tube formation, it is useful to evaluate whether there is a modification of the steady state transcript levels of the immediate-early endothelial differentiation genes (edg genes). This establishes whether the effect of the γ-Jaggged oligomer occurs during immediate-early or mid-to-late phase of the endothelial cell differentiation pathway and supplements the qualitative data with respect to the modification of lumen formation in vitro. While the end point for this assay will be a qualitative assessment of lumen formation as previously described (Jaye et al., 1985), cells will be harvested as described in Example 3 (FIG. 5) for Northern blot analysis of the presence or absence of the edi genes, such as the G-protein-coupled orphan receptor, edg-1 (Hla and Maciag, 1990), the transcription factor, edg-2 (Hla et al., 1995, Biochim. Biophys. Acta 1260:227–229), cyclooxygenase-2 (cox-2) (Hla and Neilson, 1992, Proc. Natl. Acad. Sci. USA 89:7384–7388), and tissue collagenase, among others (Hla and Maciag, 1990).

Because the data indicate that the γ-Jaggged oligomer accelerates capillary endothelial cell migration and sprout formation in vitro, the addition of the Jagged protein to these systems will have the opposite effect—inhibiting capillary endothelial cell migration and sprout formation and promoting large vessel-derived endothelial cell migration in vitro. However, two approaches may be used to evaluate this premise. The first involves the expression and purification of the Jagged polypeptide as a recombinant protein, and the second involves the expression of an extracellular and soluble Jagged construct (as disclosed in Example 9, infra). Although the predicted Jagged sequence does not contain any recognizable post-translational modification motif in the extracellular domain of the protein, such as N-glycosylation, it is possible that a subtle modification of the Jagged protein will affect the activity of Jagged as a Notch ligand.

Using the recombinant Jagged protein, it is possible to assess its ability to signal through the Notch-1 receptor using a rat myoblast system. Since it has been demonstrated that the rat myoblast cell line, C2C12, transfected with the Notch-1 cDNA will not form myotubes when co-cultured with a lethally irradiated population of murine fibroblast transfected with the rat Jagged cDNA (Lindsell et al., 1995, Cell 80:909–917), it is assumed that the parental C2C12 is a Notch-1-deficient cell line. Therefore, the C2C12 cell represents a model cell type to assess the biological function of recombinant Jagged.

The C2C12 cell Notch-1 transfectants, but not C2C12 insert-less vector transfectants, presumably are unable to form myotubes if the recombinant Jagged protein is functional as a ligand. Thus, this system also permits an assessment of the value of Notch-2 as a Jagged receptor.

C2C12 cells are transfected with the full length rat Notch-1 and Notch-2 cDNA containing tandem copies of the influenza virus hemagglutinin (HA) epitope and stable transfectants obtained as described (Zhan et al., 1992). The expression of the Notch-1 and Notch-2 receptor transcripts is monitored by RT-PCR and Northern blot analysis and the protein levels assessed by immunoprecipitation/Western blot analysis of the HA epitope. The addition of the recombinant Jagged ligand (1 ng to 10 μg titration) permits the Notch-1 and Notch-2 C2C12 cell transfectants to repress myotube formation, as assessed by morphologic criteria as well as by the repression of the steady-state levels of the myogenic transcript. These data also define the specific activity of the recombinant Jagged protein for stability studies (temperature, pH, ionic strength as a function of time). An appropriate positive control for these experiments is a population of lethally-irradiated NIH 3T3 cells transfected with the full-length Jagged cDNA to the Notch-1 and Notch-2 C2C12 cell transfectants, insuring the attenuation of myotube formation.

After the specific activity of the soluble Jagged protein is established, it will be possible to assess the ability of the Jagged ligand in a concentration dependent matter to inhibit microvessel endothelial cell migration, chemotaxis and sprout formation in vitro, as in FIGS. 5 and 6. Effective levels of Jagged protein, similar to those previously functional in the C2C12 cell Notch-1 transfectants, are expected to also be functional in the human and bovine microvascular endothelial cell systems. A comparable evaluation involves a determination of the function of the Jagged protein as an inducer of large vessel-derived human and bovine endothelial cell migration, chemotaxis, and sprout formation. A concentration-dependent response is indicated. As described above, the co-culture of the large and small vessel-derived endothelial cells with lethally irradiated NIH 3T3 cell Jagged transfectants and insert-less vector transfectants provides a suitable control to demonstrate the disparate role of Jagged-Notch signaling in the regulation of endothelial cell migration.

Example 7

The Relevance of Jagged-Induced Signaling in Vitro to Angiogenesis In Vivo

Because Jagged was cloned as a fibrin-responsive gene in vitro, an in vivo angiogenic system is needed which closely mimics the in vitro system. Traditional angiogenesis assays, such as the chicken chorioallantoic membrane (CAM) (Scher et al., 1976, Cell 8:373–382) assay or the rabbit cornea assay (Folkman et al., 1983, Science 221:719–725), are useful for an end-point analysis, and are readily available in the art. However, the complexity of the many individual steps in the angiogenic cascade (FIG. 1), and their control by gene regulation, demands a novel in vivo approach that addresses this complexity more specifically.

Plating HUVEC on fibrin has been selected to meet the need for such an in vivo system. It has proven to mimic in vivo, in a reproducible fashion, the in vitro system we used initially to induce and isolate the human Jagged cDNA. The in vivo system involves the subtotal occlusion of a large vessel, such as a carotid or iliac artery with a thrombus, producing an intimal injury. This is typically followed within two days, by migration of endothelial cells into the three-dimensional platelet/fibrin scaffold tube formation. After approximately 4 weeks the system characteristically displays tube perfusion, recruitment of pericytes, and selection of preferred channels with downsizing of minor vessels. Together with the vessels, stromal cells appear as well, contributing to the unique extracellular matrix of this tissue, and making this natural, in vivo system (involving revascularization of an experimental thrombus) ideal for demonstrating the role of Jagged and its receptor(s) in two of the early steps of angiogenesis.

Endothelial migration and tube formation can be separated in time (at 2, 4, 6, 8 days after thrombosis), as well as in space. The migrating cells are primarily located in the central region of the thrombus, whereas the peripheral cells have already formed tubes, as indicated by the appearance of junctions and, almost concomitantly, the arrival of circulating red blood cells.

The antibodies developed for use in this experimental system were designed for use with known immunoperoxidase or immunofluorescence techniques to localize endogenous Jagged and Notch (Nabel et al., 1993, Nature 362:844–846). However, an advantage of using this in vivo system is that the experimentally-induced thrombus can be seeded with genetically modified cells, γ-Jaggged oligomer, or soluble Jagged protein as described above for the in vitro approach, to influence two distinct phases of the angiogenic cascade in a controlled fashion.

The source of these endothelial cells is from large vessels, but they behave like capillaries when they migrate and form tubes, until some, but not all, will recruit pericytes and smooth muscle cells and assume the appearance and function of large vessels again. Clinically, both in the coronary and in the peripheral circulation, this revascularization process is critical, since successful recanalization of occluding thrombi is highly beneficial to the patient, but its regulation has been poorly understood.

Although an expert qualitative pathologic-anatomical evaluation of the vascular morphology is essential in these in vivo experiments, there are a number of time points that are amenable to quantitative morphometric analysis. This is especially relevant since these time points represent distinct stages in this process. At 4, 6, and 8 days, the number of invading cells are directly counted using a light microscope to evaluate cross-sections. Using immunohistochemical analysis with the CD34 antibody, the relative number of migrating endothelial cells is quantifiable; and using the leukocyte common antigen, the inflammatory cells can be assessed. Unfortunately, smooth muscle cell α-actin cannot be used as a reliable marker for myofibroblasts at this stage, since their phenotype is altered. However, by subtraction, the number of non-endothelial cells can be determined.

Thus, quantification of this early phase indicates whether, and in which direction, the interplay between Jagged and Notch influences the migratory component of the angiogenic process. Using serial sections of the same preparations, the proliferative cell nuclear antigen is useful to evaluate the relative contribution of proliferation to the total number of cells that populate the thrombus. When the thrombus is seeded with transfected cells expressing soluble Jagged, the myc reporter gene is used to recognize and count these components within the system.

Quantification of the functional vascular lumina in a cross-section after 2 and 4 weeks provides additional insight into the relationship between tube formation and the processes of endothelial migration and proliferation during angiogenesis. This comprises a statistical comparison of the number of individual lumina, grid point counts, and area measurements in perfused vessels. Mechanistically, the Jagged/Notch interaction which initiates tube formation from large vessel endothelial cells in vitro, may prove to be a stop signal for migration and proliferation of the microvasculature.

The endothelial cell site-specific effect of the Jagged-Notch system may also be responsible for the control and coordination of the migration/proliferation/tube formation sequence that ultimately leads to the formation of a new vessel. This can be shown in vivo in a revascularized thrombus murine model system, in which it is possible to deliberately exaggerate or compete with each of the components at the molecular level and at any time point within the process. Indeed, the kinetics of the Jagged/Notch interaction may also be assessable by seeding the thrombus at a later time point with soluble Jagged transfectants.

In the mouse, experimental intervention will involve a surgical exposure of previously treated, occluded carotid artery for an injection of a small volume of either lethally irradiated transfectants, recombinant protein or γ-Jaggged oligomer into the site. However, the occluded vessel cannot bleed due to incomplete revascularization. Appropriate controls for the repetitive minor surgical trauma are possible in the same mammal on the contralateral carotid, using cells transfected with an inactive, but minimally altered mutant, inactive recombinant protein, or sense or inactive mutant γ-Jaggged oligomers respectively.

While the model is useful to examine the formation of a new three-dimensional network of functioning vascular tubes, an additional model for the re-endothelialization of the intima of a large vessel is needed, since Jagged/Notch appears to regulate this process in the opposite direction. Since murine vessels are too small for precise, selective de-endothelialization, the gently ballooned rat thoracic aorta (access from the carotid with a French 2 Edwards balloon) is an appropriate test system since it offers unequivocal starting points, and reasonably accurate quantification (see Schwartz et al., 1978, Lab. Invest. 38:568–580).

To assess the ability of the Jagged ligand to modify the migration of endothelial cells, thus influencing their ability to form a capillary network and/or to cover a de-endothelialized surface, one of several methods is indicated. In a first method, a therapeutically-effective amount of soluble Jagged ligand is administered intravenously to mice and/or rats prior to and/or following thrombosis or balloon injury. In an alternative method, a thrombotic occlusion in a mouse is seeded with an effective amount of lethally irradiated NIH 3T3 cell soluble Jagged:myc transfectants. While in a third method, in both rats and mice, a distal site is seeded with an effective amount of lethally irradiated NIH 3T3 cell soluble Jagged:myc transfectants onto a subcutaneous fibrin matrix implant, which has been pretreated with lethally irradiated NIH 3T3 cells transfected with a hst-sp-FGF-1 construct using the nude mouse (Forough et al., 1993, J. Biol. Chem. 268:2960–2968).

It is known that the NIH 3T3 cells hst-sp-FGF-1 transfectants ($10^5$ cells) are able to secrete FGF-1 as an extracellular angiogenesis signal, and establish within 5 to 10 days an aggressive capillary network (Forough et al., 1993). This is a result of the ligation of the signal peptide (sp) sequence from the hst/KS5 (FGF-4) gene to FGF-1, which directs the traffic of the hst-sp-FGF-1 chimera into the ER-Golgi apparatus for proteolytic processing of the hst/KS5-sp-sequence and release of FGF-1 as a soluble, extracellular protein. The efficacy of this construct has been established in vivo (Nabel et al., 1993; Robinson et al., 1995, Development 121:505–514).

In the third method, following thrombotic occlusion, the NIH 3T3 cell soluble Jagged:myc transfectants ($10^6$–$10^7$ cells) are injected into the angiogenic site, enabling the cells to express and secrete the soluble Jagged protein into the vasculature. The levels of plasma-derived Jagged (tail vein samples) are monitored by ELISA using the myc-epitope and Jagged antibodies. The rats are then assessed over time (e.g., 1 to 10 days at 2 day intervals) for re-endothelialization of the denuded artery using Evan's blue staining. The degree of angiogenesis in the occlusion zone in the murine vessels is assessed using morphometric analysis of individual endothelial cells and of the fully developed capillary vessels in histological sections. Indeed, analysis by transmission electron microscopy will clearly demonstrate the involvement of endothelial cell migration and sprout formation in this system.

The assessment of the pharmacologic administration of intravenous soluble Jagged in the first method is based upon a similar end point, but utilizes a sufficient amount of recombinant Jagged to saturate both the Notch-1 and Notch-2 receptor Jagged-binding sites. The number and affinity of Jagged-binding sites on the surface of the murine endothelial cell are quantified in vitro by Scatchard analysis of murine aorta-derived endothelial cells and adipose-derived microvascular endothelial cells using competitive ($^{125}$I)-Jagged binding by the method described for FGF-1 (Schreiber et al., 1985, Proc. Natl. Acad. Sci. USA 82:6138–6142).

The apparent lack of regulation of the Notch-1 and Notch-2 transcripts in the HUVEC population (FIG. 5), predicts a high affinity Kd (pM) with approximately 5–20,000 Notch-binding sites per cell. The radiolabelling of the Jagged polypeptide utilizes the lactoperoxidase method, followed by removal of free ($^{125}$I) by Sephadex G-50 gel exclusion chromatography. This provides a pharmacologic range for the administration of the ligand. In addition, the availability of ($^{125}$I)-Jagged will demonstrate the expected pharmacokinetics of intravenous Jagged using methods previously successful for FGF-1 (Rosengart et al., 1989, Circ. Res. 64:227–234).

In sum, these models should provide an in vivo correlate and in vivo models for Jagged function, demonstrating a predicted increase (25%–35%) in lumen re-endothelialization, and a similar decrease in the formation of capillary structures. In comparisons between the in vivo revascularization and re-endothelialization experiments in normotensive animals, and in their spontaneously hypertensive rat counterparts (SHR, commercially available from Charles River with guaranteed hypertension), it has been shown that hypertension has a direct, albeit subtle, effect on the aortic endothelium of these model animals (Haudenschild et al., 1981, Hypertension 3:148–153). The aortic re-endothelialization experiments can be repeated in these rats without modification and with hypertension as the only added variable, however, the thrombus revascularization experiments must also be performed in these rats, since there is no comparable murine hypertension model available. The thrombi have been shown to be readily reproducible in mice, rats and rabbits. Thus, species differences do not pose a technical problem in the in vivo model systems.

Example 8

Expression of Soluble Jagged in the NIH 3T3 Cell Line

To determine the effects of a secreted, extracellular form of Jagged, a modified form of the nucleic acid encoding Jagged was synthesized, transfected into the NIH 3T3 cell line, and then cells were selected that produced the protein. To track and monitor the fate of this Jagged molecule, a myc tag (reviewed by Kolodziej and Young, 1991, Meth. Enzymol. 194:508–519) was also introduced at the 3' end of the gene. In order to do this, several modifications of the jagged gene were necessary, these are: (1) a Kozak sequence (Kozak, 1989, J. Cell Biol. 108:229–241) was engineered onto the 5' end of the gene to ensure efficient transcription, (2) a myc epitope tag was placed at the 3' end, and (3) cloning sites were engineered on both the 5' end (EcoRI, BamHI, SalI sites) and the 3' end (XhoI site).

The primer pairs used for this construction were as follows.

The primers used to construct the 5' end of the molecule were: forward primer 5'-GACTATGCG AATTCGGATCCGTCGACGCCACCATGG-3' (SEQ ID NO:13), and reverse primer: 5'-CAAGTTCCCCCGTTGAGACA-3' (SEQ ID NO:14).

The primers used for construction of the 3' end of the molecule encoding Jagged-myc tag were as follows: reverse primer 5'-GCATAGTCCTCGAGTTACAAGTCTTCTT CAGAAATAAGCTTTTGTTCTACGA TGTACTCCAT-TCG (SEQ ID NO:15), and forward primer 5'-ATGGACAAACACCAGCAGAA (SEQ ID NO:16). PCR cycling reactions were performed as described previously elsewhere herein.

The 5' reaction amplification product was digested with EcoRi and BglII. The 3' amplification product was digested with XhoI and AccI restriction endonucleases. The two amplicons were ligated into a similarly digested Jagged template construct using a standard protocol well-known in the art. The final gene product was then digested with EcoRI and XhoI and then ligated into the eukaryotic expression vector pMexNeo2. This expression construct was then transfected into the NIH 3T3 cell line and cells were grown in selection media containing G418 as described elsewhere herein and/or per standard protocols well-known in the art such as those described in Sambrook et al. (1989, Molecular Cloning: A Laboratory Manual, Cold Spring Harbor Laboratory, New York), and Ausubel et al. (1997, Current Protocols in Molecular Biology, John Wiley & Sons, New York).

Calcium mediated DNA transfer into NIH 3T3 cells was followed by growth in selective media and resulted in selection of clone MW38-1.1 (SEQ ID NO:17). The data disclosed herein demonstrate that clone MW38-1.1 synthesized a protein having the anticipated characteristics (e.g., molecular weight, amino acid sequence [SEQ ID NO:18], and the like) of Jagged-myc tag and that the protein was released into the surrounding medium, termed "conditioned media."

The data disclosed herein demonstrate that transfectant cells expressing clone MW38-1.1 exhibited a unique phenotype. The transfectants grossly formed chord-like structures in vitro correlating with the presence of pseudo-lumens by ultrastructure analysis (see Example 9, FIGS. 10B and 10D). In addition, the cells were able to induce wild type NIH cells to partially assume this phenotype. Therefore, the data disclosed herein demonstrate that MW38-1.1 transfectant cells are an outstanding resource both for the production and isolation of the soluble Jagged (also referred to as "sol-jag") protein (SEQ ID NO:18), and for their ability to modulate the differentiation pattern of adjacent cells.

Example 9

In vivo and in vitro Effects of Soluble Jagged Expression

The experiments presented in this example may be summarized as follows.

As discussed previously elsewhere herein, Jagged-Notch interactions regulate a transmembrane ligand-receptor signaling pathway involved in the regulation of cell fate determination as well as myoblast and endothelial cell differentiation. To further examine the role of the transmembrane ligand, Jagged-1, in the regulation of endothelial cell differentiation (Zimrin, et al., 1996, J. Biol. Chem. 271:32499–32505), NIH 3T3 cells were stably transfected using a nucleic acid encoding a truncated form of Jagged-1 (FIGS. 13B and 13C, [SEQ ID NO:17]), which results in the secretion of a soluble form of the protein, i.e., soluble Jagged (FIG. 13A, [SEQ ID NO:18]). Comparison of gene expression by serial analysis demonstrated that pro-α-2(I) collagen was repressed in soluble Jagged-1 transfectants. The data disclosed herein further demonstrate that when plated on extracellular matrices, soluble Jagged-1 transfectants formed prominent chord-like structures of Type I collagen but did not form such structures when plated on fibrin, fibronectin or vitronectin.

While the soluble Jagged-1 transfectants exhibited growth kinetics similar to control cells and were unable to grow in soft agar, the cells were less sensitive to contact inhibition of growth in vitro and soluble Jagged-1 allografts formed tissue masses in nude mice after a prolonged latency period. Because these tumor-like structures exhibited an abundance of host-derived microvascular endothelial cells, the angiogenic potential of the soluble Jagged-1 transfectants was assessed by implantation of lethally-irradiated transfectants in the chick chorioallantoic membrane assay. These irradiated transfectant cells were not only able to induce angiogenesis but were also able to direct the formation of large macrovessel-like structures.

These data disclosed herein indicate that Jagged-1 can initiate angiogenesis by the organization of matrix-sensitive cell-cell interactions including its ability to promote the development of chord-like structures.

The Materials and Methods used in the experiments presented herein are now described.

Soluble Jagged-1 Plasmid Construction

The soluble myc epitope-tagged Jagged expression vector was generated using two separate sequential polymerase chain reaction (PCR) protocols. Overhang PCR was used to place a consensus Kozak sequence (Kozak, 1989, J. Cell Biol. 108:229–241) 5' to the Jagged-1 open-reading frame (ORF), and to truncate Jagged-1 immediately 5' to the transmembrane domain. This construct was assembled by ligating the PCR-modified 5' and 3' amplicon into the shuttle plasmid, MW27, which consists of the full-length Jagged-1 cDNA in pBlue Script and was subcloned into the eukaryotic expression vector pMexNeo2 (Martin-Zanca et al., 1989, Mol. Cell. Biol. 9:24–33) using the newly engineered 5' EcoRI and 3' XhoI sites to produce the final product. The forward primer used for the 5' modifications was 5'-GACTATGCGAATTCGGATCCGTCGACGCCACCA TGGGTTCCCCACGGACAC GCG-3' (SEQ ID NO:19) and reverse primer was 5'-CAAGTT CCCCCGTTGAGACA-3' (SEQ ID NO:20), where the Kozak sequence is underlined. The forward primer used for the 3' modification was 5'-ATGGACAAA CACCAGCAGAA-3' (SEQ ID NO:21) and reverse primer was 5'-TAG TGCTCGAGCTATTACAAGTCTTCTTCA-GAAATAAGCTTTTGTTCATCTG TTCTGTTCTTCAG-3' (SEQ ID NO:22), where the myc epitope is underlined. The template used for PCR was the complete human Jagged-1 ORF originally obtained form Dr. G. Gray, Yale University.

PCR reactions were performed using Vent polymerase (New England Biolabs, Beverly, Mass.) in 1×vent buffer as recommended by the manufacturer. PCR thermal cycling parameters consisted of 94° C. (1 minute) followed by 35 cycles at 94° C. (30 seconds), 62° C. (30 seconds), 72° C. (30 seconds) followed by a 10 minute hold at 72° C. before termination at 4° C.

The 5' PCR-modified product was digested with EcoRI and BglIII, electrophoretically resolved on a 1% (w/v) agarose gel, electroeluted, and then ligated with a similarly digested MW27 to create MW13 using standard protocols (Sambrook et al., 1989, Molecular Cloning, Cold Spring Harbor Laboratory Press, Cold Spring Harbor, N.Y.). The modified 3' PCR-amplified product was processed similarly except that the restriction digestion step utilized XhoI and AccI. The ligation was performed with a similarly digested MW13 to yield MW32. This 5'-Kozak-truncated Jagged-1 3'-myc-tagged pBlueScript construct was digested with EcoRI and XhoI and ligated into pMexNeo. All restriction enzymes and buffers were obtained from New England Biolabs and two soluble Jagged-1 transfectant clones, 38-1 and 38–4, and one insert-less vector transfectant clone were used for experimentation.

Cell Transfection, Immunoprecipitation, Immunoblot Analysis, and Matrix Preparation NIH 3T3 cells were transfected with clone 38 (also referred to as "MW38") using a calcium-phosphate kit (Stratagene, La Jolla, Calif.) and resulting transfectants were selected using G418 (Gibco/BRL, Gaithersburg, Md.) selection. Stable soluble Jagged-1 transfectants were grown and maintained in DMEM (GIBCO/BRL, Gaithersburg, Md.) supplemented with 400 µg/ml G418 and 10% (v/v) fetal bovine serum (FBS) (HyClone, Logan, Utah). G418 resistant cells were grown to confluency in DMEM containing 10% (v/v) FBS, the cells were washed twice in phosphate-buffered saline (PBS), and the cells were then incubated with [35S] labeling media consisting of cys- and met-free DMEM supplemented with 1×Nutriderma (Gibco/BRL, Gaithersburg, Md.) and 0.4 µCi/ml of [$^{35}$S]-met/cys mixture (DuPont-New England Nuclear). After 4 hours, the labeling medium was removed, the cells were washed once with ice cold PBS, and the cells were scraped into 1.0 ml of PBS. The cells were pelleted and the cell pellets were resuspended in RIPA lysis buffer containing 1 mM PMSF, 10 µg/ml aprotinin and 1 µg/ml leupeptin (Sigma Chemical Co., St. Louis, Mo.). The samples were clarified by centrifugation (13,000×g for 10 minutes) and then incubated with 30 µl of Protein-A Sepharose (Pharmacia LKB Biotechnology, Inc., Piscataway, N.J.) which had been complexed with 9E10 anti-myc monoclonal antibodies (Oncogene, Boston, Mass.). The immunoprecipitates were washed four times with RIPA buffer, and the immunoprecipitates were then dissolved in 50 µl of 2×SDS sample buffer. The eluted proteins were resolved in 8% SDS-PAGE as described previously (Laemmli, 1970, Nature 227:680–685).

To assess the secretion of soluble Jagged-1, the conditioned medium (1 ml) from the [$^{35}$S]-met/cys-labeled cells was collected in 1 mM PMSF and 10 µg/ml aprotinin then incubated with 50 µl of Protein-A Sepharose and treated as outlined above for cell lysates except that the immunoprecipitates were washed six times prior to being dissolved in SDS sample buffer.

Confluent monolayers of soluble Jagged-1 NIH 3T3 and insert-less vector NIH 3T3 cell transfectants were lysed by scraping in 1 ml of SDS-PAGE sample buffer containing 2% (v/v) mercaptoethanol and the samples were boiled for 10 minutes. To equalize for protein load, cells were independently lysed by scraping into 20 mM Tris buffer, pH 7.5, containing 1% (v/v) Triton X100, the protein concentration was measured using the Coomassie Protein Assay Kit per the manufacturer's instructions (Pierce Chemical Co., Rockford, Ill.), equal protein loads were resolved using 6% acrylamide (w/v) SDS-PAGE. The proteins were transferred to Hybond C membranes (Amersham, Arlington Heights, Ill.) using standard methods. The blots were immunostained using the SP 1.D8 mouse monoclonal antibody specific for pro-α-1(I) collagen amino-terminal extension peptide (Developmental Studies Hybridoma Bank, University of Iowa). Pro-α-1(I) collagen was visualized using a horseradish peroxidase-conjugated goat anti-mouse IgG (Bio-Rad Laboratories, Richmond, Calif.) and an enhanced chemiluminescence (ECL) detection system (Amersham).

Cell culture dishes were coated with 10 µg/cm² of human fibronectin for 2 hours, the fibronectin was removed, and the plates were washed three times with sterile PBS. Collagen gels were formed in 6-well plates by mixing 8 volumes of type I collagen (Vitrogen 100, Collagen Corporation, Palo Alto, Calif.) with 1 volume of 10×DMEM (Gibco/BRL) and 1 volume of sodium bicarbonate (11.8 mg/ml) on ice and then quickly dispensing (1.5 ml) of the mixture into each well of the individual cell culture dishes. The collagen mixture was allowed to gel for 1 hour prior to use. Soft agar growth assays were performed as described previously (Forough et al., 1993, J. Biol. Chem. 268:2960–2968).

Serial Analysis of Gene Expression (SAGE)

The SAGE method was performed as previously described (Zimrin and Maciag, 1996, J. Clin. Invest. 97:1359). Briefly, polyA$^+$ RNA derived from insert-less vector control and from soluble Jagged-1 NIH 3T3 cell transfectants converted to double stranded (ds)-cDNA (cDNA Synthesis System, BRL) was purified by reversed phase HPLC using 5'-biotin-dT$_{18}$ (Integrated DNA Technologies, Inc., Coralville, Iowa). The cDNA was cleaved with NlaIII, and the 3'-biotinylated fragments were captured on streptavidin-coated magnetic beads (Dynal, Oslo, Norway). The bound cDNA was divided into two pools, and one of the following linkers containing recognition sites for BsmFI and a NlaIII complementary terminus was ligated to each pool: linker 1, 5'-TTTGGATTTGCTGGTGCAGTACAACTAGGCTTA ATAGGGACATG-3' (SEQ ID NO:23), 5' TCCCTAT-TAAGCCTAGTTGT ACTGCACCAGCAAATCC (amino-C7)-3' (SEQ ID NO:24) and linker 2, 5'-TTTCTGCTCGAA TTCAAGCTTCTAACGATGTACGGGGACATG-3' (SEQ ID NO:25), 5' TCCCCGTACATCGTTAGAAGCTTGAAT-TCGA GCAG (amino-C7)-3' (SEQ ID NO:26).

SAGE tags were released with BsmFI, the tag overhangs were filled in using T7 polymerase, and the tags were ligated using T4 DNA ligase (BRL) overnight at 25° C. The SAGE tags were diluted and amplified by PCR for 28 cycles (primers: 5'-GGATTTGCTGGTGCAGTACAACT-3' [SEQ ID NO:27] and 5'-CTGCTCGAATTCAAGCTTCTAAC-3' [SEQ ID NO:28]). The product was fractionated using polyacrylamide gel electrophoresis (PAGE), and the 104 bp product containing two tags ligated tail to tail (ditag) was excised and extracted from the gel. The product was cleaved with NlaIII, and the ditags were purified by gel electrophoresis, excised from the gel, and then self-ligated to produce ditag concatamers (Velculescu et al., 1995, Science 270:484–487; Velculescu, 1997, Cell 88:243–251). The concatenated products were separated by PAGE, and products ranging from about 300 bp to about 800 bp were excised from the gel and cloned into the SphI site of pZero (Invitrogen, Carlsbad, Calif.).

Colonies were screened for insert size by PCR using M13 forward and M13 reverse primers. Clones were introduced into 25 μl PCR reactions containing 0.5 μM M13 forward and reverse primers and the samples were then subjected to thermal cycling (25 cycles) consisting of 20 seconds at 95° C., 1 minute at 52° C. and 1 minute at 72° C. Clones selected on the basis of insert size were subjected to automated fluorescent DNA sequence analysis using rhodamine dideoxynucleotide terminator chemistry according to the instruction of the manufacturer (Applied Biosystems, Inc., Foster City, Calif.).

The sequence files were analyzed by means of the SAGE program group, which identifies the anchoring enzyme site with the proper spacing, extracts the two intervening tags, and records them in a database. The potential identities of the tags was established by their presence in GenBank or DbEST databses (release 109).

Assessment of Soluble Jagged-1 NIH 3T3 Cell Transfectant Behavior in Vivo

The soluble Jagged-1 NIH 3T3 cell transfectants were grown to confluence under G418 selection and, 24 hours prior to injection, the medium was changed to DMEM containing 10% (v/v) FBS. The transfectants were washed with PBS, harvested by trypsin digestion, and then resuspended in sterile/pyrogen-free PBS prior to injection. The cells were greater than about 95% viable as determined by Trypan Blue exclusion and were free of mycoplasma and indigenous murine viruses including mouse hepatitis, adenovirus, pneumonia, cytomegatovirus and Sendai (Anmed/Biosafe Inc., Rockville, Md.).

Female athymic nude mice (nu/nu) between 8–12 weeks of age (NCI-FCRDC) received 150 mg/kg of cyclophosphamide in pyrogen-free water by the intraperitoneal route 24 hours prior to injection. Injection of a 200 μl cell suspension ($10^6$) was administered intradermally into the right flank.

Following euthanasia, tissue growths were exposed by dissecting along the subcutaneous tissue plane and the tissue masses were removed, fixed in 10% (v/v) buffered formalin, and the tissue was processed for paraffin sectioning and hematoxylin and eosin staining. Representative portions of these masses were also embedded in O.C.T. compound (Miles Scientific, Elkhart, Ind.) and snap frozen in 2-methylbutane (E.M. Science, Gibbstown, N.J.) on dry ice. Frozen sections were placed onto glass slides, fixed in chilled acetone, and dried.

Immunohistochemistry was performed using the ABC system (Vector Laboratories, Burlingame, Calif.) and a 1:200 dilution of an antibody (PharMingen, San Diego, Calif.) to rat-derived endothelial cell-specific marker CD31/PECAM.

The chick chorioallantoic membrane (CAM) angiogenesis assay was performed as described previously (Brooks et al., 1994, Science 264:569–571; Jadhav et al., 1999, FASEB J. 13:4) and utilized 2.5×106 lethally irradiated soluble Jagged-1 NIH 3T3 cell transfectants per CAM. Recombinant human FGF-2 and insert-less vector NIH 3T3 cell transfectants served as positive and negative controls, respectively. The assay was harvested 4 days post-implantation and the angiogenic index was quantitated by computer-assisted morphometric analysis of vessel number.

The Results of the Experiments presented herein are now described.

Angiogenesis is an integral part of physiologic and pathologic processes such as embryonic development, wound repair, solid tumor growth and chronic inflammation and involves the ability of the endothelial cell to coordinate migration, proliferation, and differentiation pathways to form new vascular structures (Zimrin and Maciag, 1996, J. Clin. Invest. 97:1359; Folkman and D'Amore, 1996, Cell 87:1153–1155). While the ability of the angiogenic growth factors, vascular endothelial growth factor (VEGF) and fibroblast growth factor (FGF) to initiate endothelial cell migration and growth are well described (Maciag et al., 1979, Proc. Natl. Acad. Sci. USA 76:5674–5678; Chen and Chen, 1987, Exp. Cell Res. 169:287–295), the identification of factors involved in the regulation of the tubular, chord-like vascular phenotype has been difficult to access. Data disclosed elsewhere herein demonstrate that the transmembrane protein, Jagged-1, a ligand for its transmembrane receptor Notch (Lindsell et al., 1995, Cell 80:909–917), is involved in the regulation of human endothelial cell differentiation in vitro (see also Zimrin and Maciag, 1996, J. Clin. Invest. 97:1359). Jagged-Notch is an evolutionarily conserved intercellular signaling pathway responsible for the regulation of developmental cell fate decisions in vivo (Weinmaster, 1998, Current Opinion in Genetics & Development 8:436–442) and cellular differentiation in vitro (Carlesso et al., 1999, Blood 93:838–848; Milner et al., 1996, Proc. Natl. Acad. Sci. USA 93:13014–13019).

During the cloning of the human Jagged-1 gene, two cDNA clones were isolated which contained identical deletions resulting in the insertion of 15 novel amino acids followed by a premature termination of the Jagged-1 sequence prior to the domain encoding the transmembrane and intracellular sequences (Example 2; see also Zimrin and Maciag, 1996, J. Clin. Invest. 97:1359). Since this truncated Jagged-1 cDNA contained the Jagged-1 signal peptide sequence, cells transfected with this construct were prepared such that the cells would secrete the truncated ectodomain of Jagged-1 as a soluble and extracellular form of the Jagged-1 protein thereby eliminating the transmembrane constraints imposed upon the non-truncated Jagged-1 ligand to signal by an intercellular pathway. The data disclosed herein demonstrate that human soluble Jagged-1 is an angiogenesis factor in vivo which is able to influence the formation of a chord-like phenotype in vitro.

SAGE Analysis of Soluble Jagged-1 NIH 3T3 Transfectants

Figure 9:
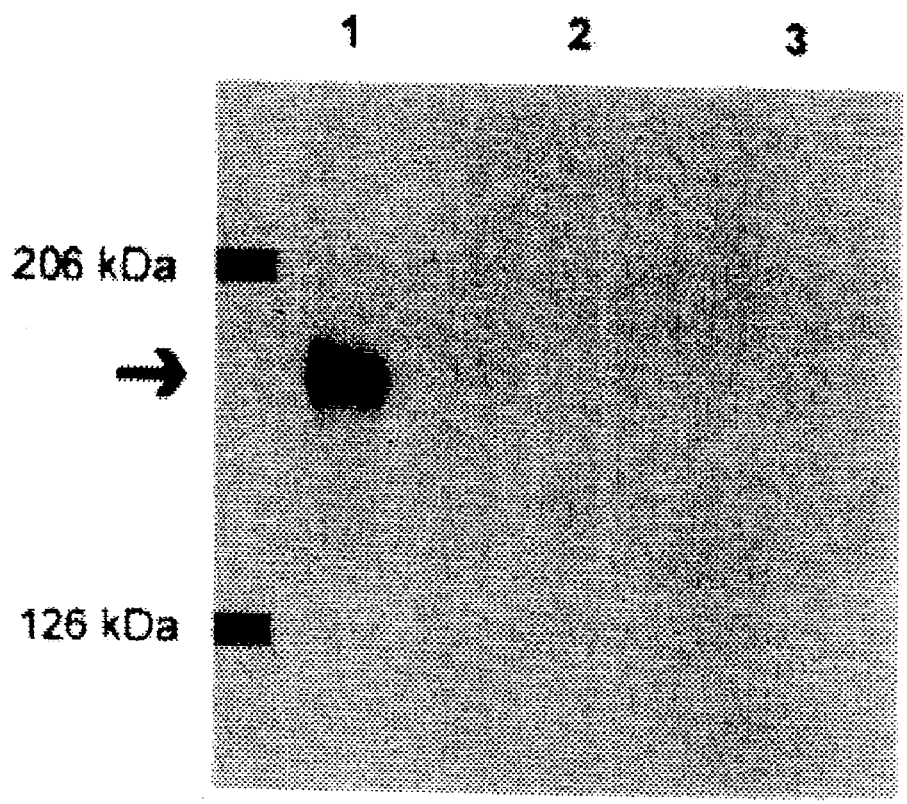
FIG. 9 is an image depicting an immunoblot analysis of murine pro-α-1(I) collagen expression in insert-less vector and soluble Jagged-1 NIH 3T3 cell transfectants. Cell lysates were prepared from pMexNeo insert-less vector control NIH 3T3 cell transfectants (lane 1), and soluble Jagged-1 NIH 3T3 transfectant clones 38-1 (lane 2) and 38-4 (lane 3). The proteins were transferred to Hybond C membranes and the blots were immunostained using SP1.D8 monoclonal antibody specific for the pro-α-1(I) collagen amino-terminal extension peptide as described elsewhere herein.

The soluble Jagged-1 transfectants were analyzed for Jagged-1 expression by immunoprecipitation of [$^{35}$S]-cys/met-labeled cells. As shown in FIG. 9, SDS-PAGE analysis of the myc epitope immunoprecipitants resolved a band of approximately 130 kDA in both cell lysate and conditioned medium which band corresponds to the size predicted by the mass of the soluble Jagged-1 myc epitope translation product.

Analysis of differential gene expression by SAGE also demonstrated that the soluble Jagged-1 transfectants were able to differentially express 227 transcripts of comprising either known or novel sequences. These results were posted at the web site for the Maine Medical Center Research Institute, and a selected number are listed in Table 1.

TABLE 1

Most Frequently Observed SAGE Tags

| RNA Source | Tags Sequenced | Discrete Tags | mRNA Species |
|---|---|---|---|
| Insert-less Vector | 1428 | 982 | 197 |
| Soluble Jagged-1 | 3150 | 1647 | 336 |
| Totals | 4578 | 2629 | 533 |

| Tag | Count | SEQ ID NO: | Acc. No. | Description |
|---|---|---|---|---|
| Tags Predominant in Soluble Jagged-1 NIH 3T3 Cell Transfectants | | | | |
| TGGATCAGTC | 14 | 34 | M62952 | *Mus musculus* ribosomal protein L19 |
| TAAAGAGGCC | 9 | 35 | U67770 | *Mus musculus* ribosomal protein S26 (RPS26) mRNA |
| CCTGATCTTT | 8 | 36 | X06406 | Mouse mRNA for translational controlled 40 kDa protein |
| TGTAACAGGA | 8 | 37 | X04648 | Mouse mRNA for IgG1/IgG2b Fc receptor (FcR) |
| TCTGTGCACC | 6 | 38 | U93864 | *Mus musculus* ribosomal protein S11 mRNA |
| CCAAATAAAA | 6 | 39 | U13687 | *Mus musculus* DBA/2J lactate dehydrogenase-A |
| CTAATAAAAG | 6 | 40 | X54691 | Mouse COX4 mRNA for cytochrome c oxidase subunit |
| GCCAAGGGTC | 6 | 41 | L08651 | *Mus musculus* large ribosomal subunit protein mRNA |
| GTCTGCTGAT | 5 | 42 | X75313 | *M. musculus* (C57BL/6) GB-like mRNA |
| AAGGAAGAGA | 4 | 43 | X51438 | Mouse mRNA for vimentin |
| TGAAATAAAC | 4 | 44 | M33212 | Mouse nucleolar protein N038 mRNA |
| CACCACCACA | 4 | 45 | X05021 | Murine mRNA with homology to yeast L29 ribosomal prot. |
| CCTCAGCCTG | 4 | 46 | X52886 | *Mus musculus* mRNA for cathepsin D. |
| CTCTGACTTA | 4 | 47 | Y16256 | *Mus musculus* mRNA for basigin |
| GTGGGCGTGT | 4 | 48 | M33330 | Mouse insuloma (rig)mRNA |
| TCCTTGGGGG | 4 | 49 | U60001 | *Mus musculus* protein kinase C inhibitor (mPKCI) mRNA |
| Tags Predominant in Control Insert-less Vector NIH 3T3 Cell Tranfectants | | | | |
| CGCCTGCTAG | 3 | 50 | X58251 | Mouse COL1A2 mRNA for pro-alpha-2(I) collagen |
| AAAAAAAAAA | 2 | 51 | AF0253 | *Mus musculus* tssk-1 and tssk-2 kinase substrate mRNA |
| AAGCAGAAGG | 2 | 52 | M16465 | Mouse calpactin I light chain (p11) mRNA complete |
| CAGGACTCCG | 2 | 53 | M26270 | Mouse stearoyl-CoA desaturase (SCD2) mRNA |
| GAAGCAGGAC | 2 | 54 | D00472 | Mouse mRNA for cofilin |
| GGATATGTGG | 2 | 55 | M20157 | Mouse Egr-1 mRNA |
| GTTCTGATTG | 2 | 56 | U88588 | *Mus musculus* cdr2 mRNA |

Note. Tags correspond to the 10 base pairs of DNA sequence data immediately following the NlaII cleavage site. The count refers to the number of instances the tag appears in the SAGE database. Accession numbers (Acc. No.) are the GenBank designations referring to the mRNA identified in the description column. SAGE was conducted using cDNA derived from NIH3T3 cells that had been stably transfected with the pMexNeo insert-less parent vector or the sJ-1 construct. A total of 4578 Tags were sequenced consisting of 1428 from pMexneo and 3150 pMexNeo sJ-1 transfected cell derived cDNA. Analysis of the data revealed a total of 2629 discrete tags comprised of 982 separate mRNA species from pMexNeo and 1647 separate mRNA species from the sJ-1-transfected cell-derived cDNA. Linkage to GenBank database version 109 yielded a total of 533 matches with documented mouse mRNA species composed of 197 mRNA species from the pMexNeo-derived tags and 336 mRNA species from the sJ-1-derived tags. A p-value of 0.05 or less was chosen as the cutoff for statistically relevant alterations and only the most predominant tags are shown.

The 163 known transcripts expressed at an enhanced level by the soluble Jagged-1 NIH 3T3 transfectants in the SAGE analysis include, but are not limited to, cathepsin D (Acc. No. Z53337), and vimentin (Acc. No. X51438).

Moreover, the 64 known transcripts with apparent reduced levels of expression in the soluble Jagged-1 NIH 3T3 transfectants include, but are not limited to, pro-α-2(I) collagen (Acc. No. X58251).

Because SAGE analysis can provide insight into the presence of known metabolic or signaling pathways, it is important to note that the data disclosed herein demonstrate that the following transcripts: sps1/ste20 related kinase, YSK2 (Acc. No. U49949), enhancer of split-Groucho, ESG (Acc. No. X73360), *Mus musculus* protein kinase C inhibitor, mPKCI (Acc. No. 6001), type IV collagenase (Acc. No. X83424), and connexin 32 (Acc. No. M63802), were present in the soluble-Jagged-1 NIH 3T3 transfectants whereas the fibroblast growth factor receptor 1, FGFR-1 (Acc. No. M33760) and the IκB-β (Acc. No. U 19799) transcripts were not present in the transfectants.

Since pro-α-2(I) collagen expression appeared to be prominent among the repressed transcripts, the expression of the translation product was examined further using insert-less vector and soluble-Jagged-1 NIH 3T3 transfectants. Because antibodies specific for pro-α-2(I) collagen are not available, the expression of the type I collagen translation product was assessed using immunoblotting to detect the pro-α-1(I) amino-terminal extension peptide using the SP 1.D8 monoclonal antibody specific for the extension peptide as described elsewhere herein. The data disclosed herein demonstrate that immunoblot analysis detected expression of pro-α-1(I) collagen translation product in insert-less vector NIH 3T3 transfectant cells (FIG. 9, lane 1), but the expression of this type I collagen was not detected in soluble Jagged-1 NIH 3T3 transfectant cells transfected with either soluble Jagged-1 clone 38-1 (FIG. 9, lane 2) or clone 38-4 (FIG. 9, lane 3).

Figure 10A:
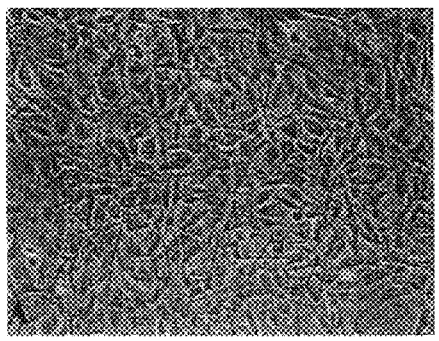
FIG. 10A is an image depicting the growth of control empty vector-transfected NIH 3T3 cells on plastic. Empty vector-transfected control NIH 3T3 cells were plated at $2\times10^4$ cells per $cm^2$ on cell culture plastic. Two days after plating, the empty vector-transfected NIH 3T3 cells on plastic did not form multicellular chords. (Phase contrast at a magnification of 100×).
Figure 10C:
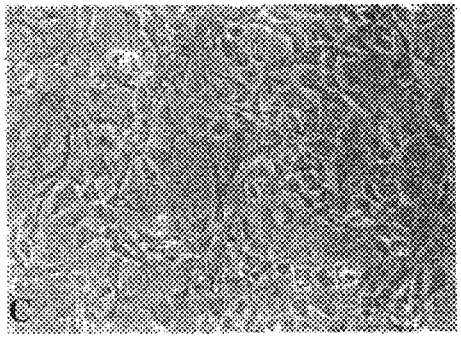
FIG. 10C is an image depicting growth of control empty vector-transfected NIH 3T3 cells on collagen. Empty vector-transfected control NIH 3T3 cells were plated at 2×10⁴ cells per cm² on collagen. Two days after plating, the empty vector-transfected control NIH 3T3 cells did not form multicellular chords on collagen. (Phase contrast at a magnification of 100×).
Figure 10B:
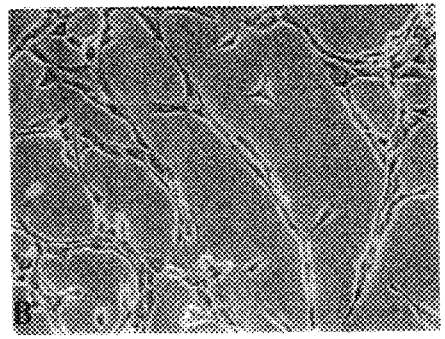
FIG. 10B is an image depicting formation of multicellular chords of soluble Jagged-1 transfected NIH 3T3 cells on plastic. Soluble Jagged-1 transfected NIH 3T3 cells were plated at $2\times10^4$ cells per $cm^2$ on cell culture plastic. Two days after plating, the soluble Jagged-1 transfectants formed multicellular chords on plastic. (Phase contrast at a magnification of 100×).
Figure 10D:
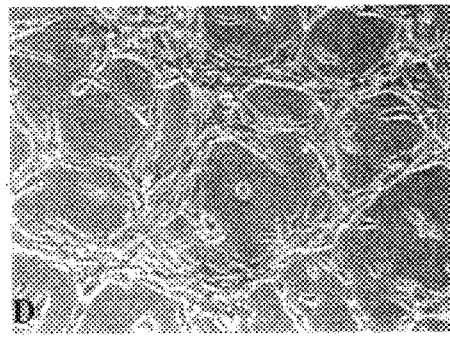
FIG. 10D is an image depicting formation of chords by soluble Jagged-1 transfected NIH 3T3 cells grown on collagen. Soluble Jagged-1 transfected NIH 3T3 cells were plated at 2×10⁴ cells per cm² on collagen. Two days after plating, the soluble Jagged-1 transfectants formed multicellular chords on both plastic (FIG. 10B, supra) and on collagen. (Phase contrast at a magnification of 100×).

NIH 3T3 cell Soluble Jagged-1 Transfectants Exhibit the Formation of a Matrix-dependent Chord-like Phenotype Since pro-α-2 (I) collagen expression appeared to be prominent among the repressed transcripts and since collagen matrices are known modifiers of cellular phenotype in vitro (Michalopoulos and Pitot, 1975, Exp. Cell Res. 94:70–78), the soluble Jagged-1 transfectant cells were plated on type I collagen. As shown in FIG. 10D, the soluble Jagged-1 transfectants plated on collagen exhibited a chord-like phenotype with the formation of an interlacing arborizing pattern. This chord-like phenotype was also observed when the soluble Jagged-1 transfectants were plated on plastic at low seed density (FIG. 10B) in which groups of cells organize into chord-like arrays one to two cells in width. While these structures progressed through the arboring phase, the monolayer assumed a normal NIH 3T3 cell phenotype as the population density neared confluence. On occasion, these structures were readily visible in the confluent monolayer and extended several millimeters in length. In contrast, soluble Jagged-1 transfectants did not exhibit a chord-like phenotype on either fibrin, fibronectin or vitronectin-coated surfaces. Likewise, neither wild type NIH 3T3 cells nor insert-less vector NIH 3T3 cell transfectants exhibited this chord-like phenotype either on plastic (FIG. 10A) or on a collagen type-1 matrix (FIG. 10C).

NIH 3T3 Cell Soluble Jagged-1 Transfectants Modify Angiogenesis

Figure 11:
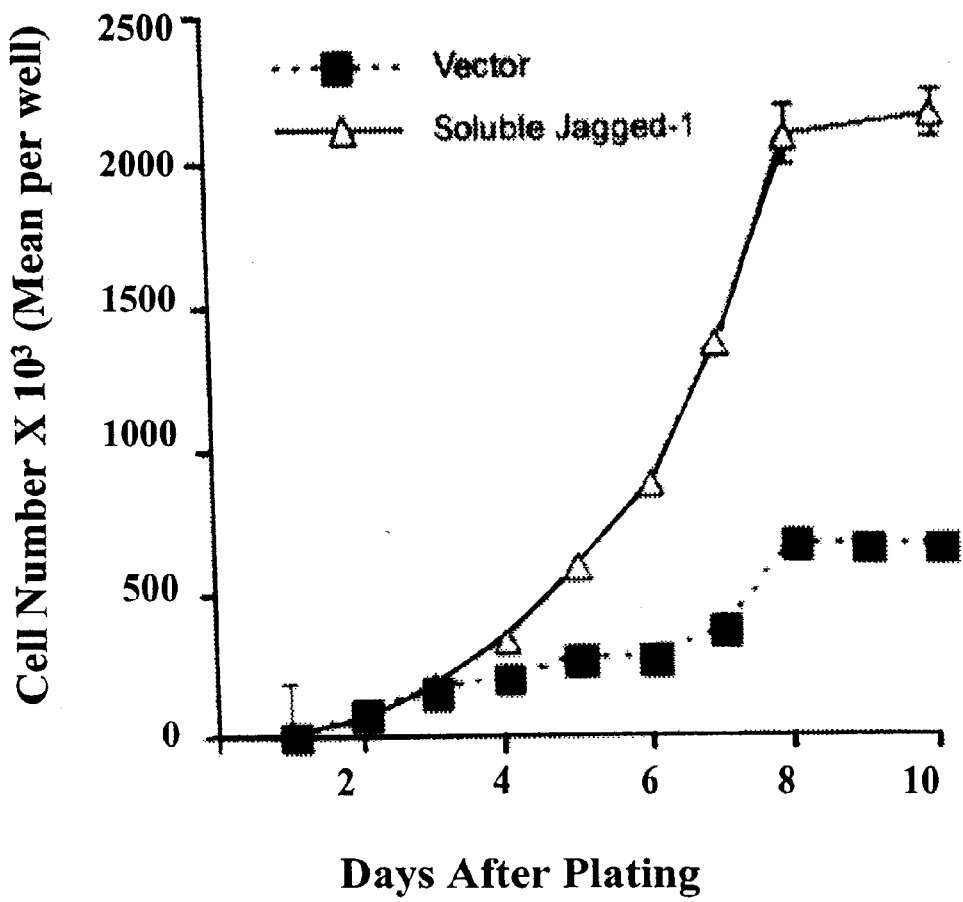
FIG. 11 is a graph depicting the growth kinetics of soluble Jagged-1 and control insert-less vector NIH 3T3 cell transfectants. The cells were plated at a seed density of 1×10⁴ cells per cm² and the cell numbers were assessed daily in quadruplicate via hemocytometer count. Both insert-less vector and soluble Jagged-1 cell populations reached confluence at approximately 4 days after plating. The data disclosed are the mean±standard error of the mean.

A comparative assessment of the proliferative potential of the soluble Jagged-1 transfectants with insert-less vector transfectants revealed that the population doubling time was not altered when cells were subconfluent and this was consistent with the absence of a transformed in vitro phenotype including the failure of the Jagged-1 transfectants to grow in soft agar. However, the soluble Jagged-1 transfectants were not sensitive to contact inhibition of growth (FIG. 11). The data disclosed herein demonstrate that the soluble Jagged-1 NIH 3T3 cell transfectants exhibited the ability to grow to significantly higher cell densities than the control insert-less vector NIH 3T3 cell transfectants.

Figure 12A:
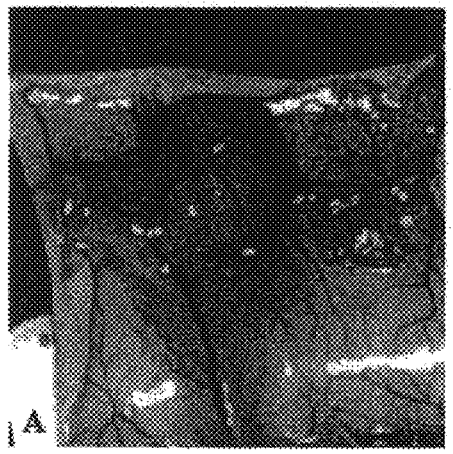
FIG. 12A is an image depicting the angiogenesis present in tissues of nude mice injected with soluble Jagged-1 transfected NIH 3T3 cells. The image depicts soluble Jagged-1 tissue mass formation in nude mice. The image depicts a deep dermal view of a soluble Jagged-1 NIH 3T3 cell tissue mass 10 weeks after intradermal injection of the cell transfectants into the flank of a nude mouse. The data disclosed demonstrate prominent angiogenesis and arborizing microvessels over the deep surface.
Figure 12B:
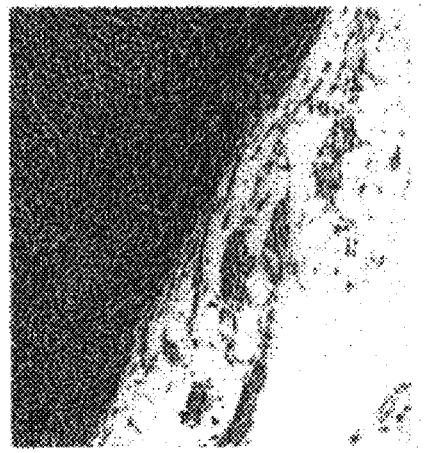
FIG. 12B is an image depicting the angiogenesis present in tissues of nude mice injected with soluble Jagged-1 transfected NIH 3T3 cells. The image depicts hematoxylin and eosin staining of a paraffin section of the soluble Jagged-1 tissue mass depicted in FIG. 12A. The image depicts prominent surface blood-filled capillaries, penetrating vessels, and intra-tumor blood islands. Magnification is 100×.
Figure 12C:
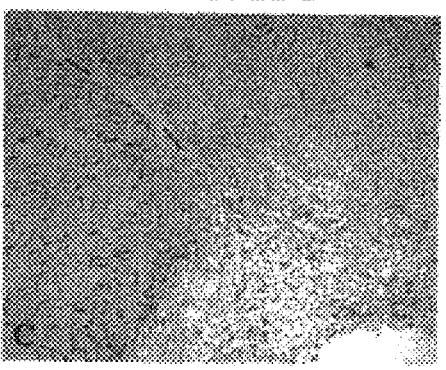
FIG. 12C is an image depicting the immunohistochemical analysis of tissues of nude mice injected with soluble Jagged-1 transfected NIH 3T3 cells using anti-CD31 (PECAM) antibody. The image depicts a low magnification (100×) view of a frozen section of the tissue mass depicted in FIG. 12A demonstrating the immunohistochemical localization of CD31 (PECAM). The image depicts two cross sections of a microvessel along with a high density of CD31 positivity.
Figure 12D:
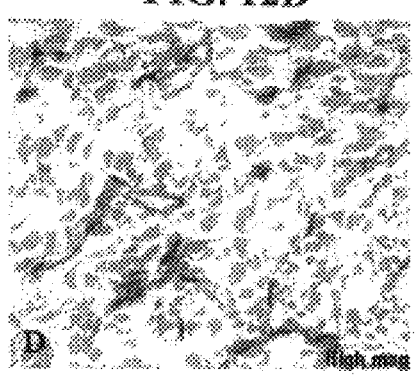
FIG. 12D is an image depicting the immunohistochemical analysis of tissues of nude mice injected with soluble Jagged-1 transfected NIH 3T3 cells using anti-CD31 (PECAM) antibody. The image depicts a higher magnification (500×) of the view of a frozen section of the tissue mass which is depicted at a magnification of 100× in FIG. 12C. The data disclosed herein demonstrate that immunohistochemical localization of CD31 is comprised of groups of single cells or angulated collection of CD31-positive cells.

Because of this difference in growth kinetics, the potential of soluble Jagged-1 NIH 3T3 cell transfectants to form tumors in nude athymic mice was assessed. Data disclosed herein demonstrate that in transplantation studies using nude mice, the soluble Jagged-1 transfectants were able to form tissue masses (FIG. 12A) but only after an extended latency period of approximately 8 weeks. Full necropsy of these animals did not reveal any evidence of local or distant metastases and gross dissection of these tissue masses revealed prominent angiogenesis characterized by 1–2 large feeder vessels, each giving rise to a rich percolating network of smaller vessels visible on the surface of the tissue mass (FIG. 12A). Histologic examination further revealed large numbers of capillaries on the surface that penetrated into the body of the tissue (FIG. 12B). Immunohistochemical analysis of the endothelial cell-specific marker, CD31 (PECAM), demonstrated not only the presence of microvessels but also a plethora of CD31-positive cells organized as a collection of either noncontiguous single cells or sharply angulated short linear arrays (FIGS. 12C and 12D). Interestingly, unlike the well-formed intratissue mass microvessels, very few of these groups of CD31-positive cells contained blood, nor were they associated with intratissue mass blood spaces (FIGS. 12C and 12D).

Since primary in vitro cell isolates of the soluble Jagged-1 transfectants obtained from these tissue masses by G418 selection demonstrated their ability to form chord-like structures and re-implantation into nude mice demonstrated their ability to develop angiogenic tissue masses with a similar latency period, the angiogenic potential of the soluble Jagged-1 transfectants was determined using the conventional chorioallantoic membrane (CAM) angiogenesis assay (Brooks et al., 1994, Science 264:569–571; Jadhav et al., 1999, FASEB J. 13:4), which is an art-recognized model of angiogenesis. Implantation of lethally irradiated soluble Jagged-1 transfectants yielded a prominent angiogenic response similar to the positive control, fibroblast growth factor 2 (FGF-2), while the insert-less vector transfectants did not. Unexpectedly, the soluble Jagged-1 CAM also exhibited the formation of prominent macrovessels, a novel and unusual feature which has not been previously observed with other angiogenic factors such as fibroblast growth factor (FGF) and vascular endothelial growth factor (VEGF) (Oh et al., 1997, Dev. Biol. 188:96–109).

Although the human Jagged-1 transcript as a gene is modified during the early stage of in vitro angiogenesis (Zimrin et al., 1995, Biochem. Biophys. Res. Commun. 213:630–638), the data disclosed herein establish a role for the soluble form of Jagged-1 as a modifier of chord formation. Interestingly, SAGE analysis disclosed herein suggests alterations in gene expression that may be relevant to the function of Jagged-1 during cell differentiation in vitro. In addition to the repression of type I collagen gene expression, the steady state levels of the transcripts for FGFR-1 and IκB are also reduced. Since Jagged-1 is apparently involved in cell differentiation, FGFR-1 signaling is antagonized by effectors which promote differentiation such as γ-interferon, PMA, interleukin-1, and tumor necrosis factor (Friesel et al., 1987, J. Cell Biol. 104:689–696; Hla et al., 1990, Biochem. Biophys. kes. Commun. 167:637–643), and since many of these modifiers of differentiation are involved in NFκβ-mediated signaling (Collins, 1993, Lab. Invest. 68:499–508), it is possible, without wishing to be bound by any particular theory, that Jagged-1-mediated Notch signaling is involved in regulating these events. This suggestion is consistent with the up-regulation of enhancer of split-Groucho, a known component of Notch signaling (Sun et al., 1996, Development 122:2465–2474). Likewise, connexin, which plays an important role in the formation of tight cell to cell contacts (Pepper and Meda, 1992, J. Cell Physiol. 153:196–205), can be modified during Jagged-1 dependent chord development. Without wishing to be bound by theory, it is also interesting that, like connexin, the increase in the expression of the type IV collagenase transcript may be relevant to the differentiation process since it is well established that proteolytic modification of collagen matrices is a component of the migratory phenotype (Lochter et al., 1999, Mol. Biol. Cell 10:271–282) during the process of chord development.

In addition, these alterations in gene expression mediated by Jagged-1 may also be involved in directing the formation of a chord-like phenotype during the organization component of the non-terminal endothelial cell differentiation pathway (Xue et al., 1999, Hum. Mol. Genet. 8:723–730). While transmission electron microscopic analysis of the chord-like structures revealed prominent interdigitations between cells with close membrane-membrane apposition, a distinct lumen with interdigitation of the plasma membrane was not readily observed despite their resemblance to the tubular phenotype observed with in vitro populations of the endothelial cells (see, e.g., Zimrin et al., 1996, J. Biol. Chem. 271:32499–32502). Without wishing to be bound by any particular theory, the data disclosed herein suggest that the absence of readily visible lumen in the soluble Jagged-1 NIH 3T3 cell transfectants may be either a consequence of another gene product, the absence of appropriate rheologic conditions, or the absence of another genomic requisite not present in the NIH 3T3 cell. Without wishing to be bound by any particular theory, the data disclosed herein further suggest that it is likely that another gene product may be responsible for lumen formations since the majority of the CD31-positive chord-like structures established in the soluble Jagged-1 tissue masses in vivo, also do not exhibit evidence of blood flow.

These data are consistent with the recent genetic observation that the Jagged-1 null mouse exhibits normal vasculogenesis but an abnormal and early lethal embryonic angiogenic phenotype including defects in the remodeling of the yolk sac and embryonic vasculature (Xue et al., 1999, Hum. Mol. Genet. 8:723–730). Indeed, the vascular pathology apparent in the Jagged-1 null mouse (id.) may be related to the inability to modulate the chord development component of the endothelial cell differentiation pathway (Zimrin et al., 1996, J. Biol. Chem. 271:32499–32502).

Likewise, the observation that mutations in the human Notch-4 gene are responsible for the formation of CADASIL, a systemic vascular disease (Joutel et al., 1996, Nature 383:707–710) is also consistent with the concept that Notch signaling is an important component of vascular physiology in humans. It is also noteworthy that observation relating the repression of Jagged-1 function in human endothelial cells to an exaggeration of the ability of FGF but not VEGF to induce sprout formation also correlates well with the role of VEGF but not FGF as a mediator of vasculogenesis since the Jagged-1 null mice exhibit hemorrhage as a result of the failure to form the large vitelline blood vessels, a process mediated by angiogenesis (Xue et al., 1999, Hum. Mol. Genet. 8:723–730). Thus, this defect may ultimately involve enhanced endothelial cell sprout formation and a failure of the mutant vasculature to form chords.

The function of the ectodomain of Jagged-1 as a biological response modifier is also consistent with the recent observation (Qi et al., 1999, Science 283:91) that the enzymatic function of kuzbanian, an ADAM metalloprotease gene family member (Rooke et al., 1996, Science 273:1227), is required for the activity of the Drosophila Notch ligand, Delta. Although it is not known whether a proteolytic modification of the Drosophila Jagged-1 homolog, Serrate (Baker et al., 1990, Science 250:1370–1377), requires a similar proteolytic modification, the data disclosed herein suggest that the ectodomain of Jagged-1 may function in the absence of its transmembrane domain as an extracellular protein.

The data disclosed herein indicate that Notch-Jagged signaling plays an important role in neoplasia. For instance, recent data demonstrated that Notch receptor expression is up-regulated in cervical cancer, Notch mutants can induce neoplastic transformation in the mammary and salivary glands, and that Notch translocation is associated with human T cell lymphoblastic neoplasms (Pear et al., 1996, J. Exp. Med. 183:2283–2291). Further, studies with human cervical carcinoma specimens demonstrate that Jagged-1 is absent in normal cervix, and is overexpressed, along with Notch, in malignant cervical adenocarcinoma. The observation that the Jagged-1 transcript is present in metaplastic lesions suggests that it may be involved in early premalignant lesion development. Therefore, without wishing to be bound by any particular theory, the data disclosed herein suggest that Jagged-1 may possess a multifaceted role in carcinogenesis by directly influencing cell-fate decisions in the neoplastic cells and by regulating endothelial cell chord development during angiogenesis.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated nucleic acid encoding a soluble Jagged protein consisting of the sequence from nucleotide number 1 to nucleotide number 3201 of SEQ ID NO:2.

2. A vector comprising the isolated nucleic acid of claim 1.

3. An isolated nucleic acid encoding a soluble Jagged protein, said soluble Jagged protein consisting of the amino acid sequence SEQ ID NO:18.

4. A vector comprising the isolated nucleic acid of claim 3.

5. An isolated chimeric nucleic acid encoding a tag polypeptide covalently linked to a soluble jagged protein, wherein said soluble jagged protein is encoded by a nucleic acid sequence consisting of nucleotide number 1 to nucleotide number 3201 of SEQ ID NO:2.

6. The isolated nucleic acid of claim 5, wherein said tag polypeptide is selected from the group consisting of a myc tag polypeptide, a myc-pyruvate kinase tag polypeptide, a glutathione-S-transferase tag polypeptide, a maltose binding tag polypeptide, green fluorescence protein tag polypeptide, an alkaline phosphatase tag polypeptide, a His6 tag polypeptide, an influenza virus hemagglutinin tag polypeptide, and a maltose binding protein tag polypeptide.

7. The isolated nucleic acid of claim 6, wherein said tag polypeptide is a myc tag polypeptide.

8. An isolated nucleic acid comprising a promoter/regulatory sequence operably linked to a nucleic acid encoding a soluble jagged protein, wherein said soluble jagged protein is encoded by a nucleic acid sequence consisting of the sequence from nucleotide number 1 to nucleotide number 3201 of SEQ ID NO:2.

9. A recombinant cell comprising the isolated nucleic acid of claim 1.

10. A recombinant cell comprising the isolated nucleic acid of claim 3.

11. A pharmaceutical composition comprising a therapeutically effective amount of an isolated nucleic acid encoding a soluble Jagged polypeptide, wherein said isolated nucleic acid consists of the sequence of SEQ ID NO:17, in a pharmaceutically acceptable carrier.

* * * * *